(12) United States Patent
Brivanlou et al.

(10) Patent No.: US 8,592,211 B2
(45) Date of Patent: Nov. 26, 2013

(54) ENHANCED PIGGYBAC TRANSPOSON AND METHODS FOR TRANSPOSON MUTAGENESIS

(75) Inventors: Ali Brivanlou, New York, NY (US); Arnaud Lacoste, Cambridge, MA (US)

(73) Assignee: The Rockefeller University, New York, NY (US)

( * ) Notice: Subject to any disclaimer, the term of this patent is extended or adjusted under 35 U.S.C. 154(b) by 574 days.

(21) Appl. No.: 12/728,943

(22) Filed: Mar. 22, 2010

(65) Prior Publication Data

US 2010/0240133 A1    Sep. 23, 2010

Related U.S. Application Data

(60) Provisional application No. 61/161,872, filed on Mar. 20, 2009.

(51) Int. Cl.
*C12N 15/09* (2006.01)
*C12N 15/63* (2006.01)
*C12N 15/87* (2006.01)
*C12N 15/00* (2006.01)

(52) U.S. Cl.
USPC ........ 435/465; 435/455; 435/440; 435/320.1; 435/377

(58) Field of Classification Search
None
See application file for complete search history.

(56) References Cited

U.S. PATENT DOCUMENTS

| | | | |
|---|---|---|---|
| 5,500,365 | A | 3/1996 | Fischhoff et al. |
| 5,689,052 | A | 11/1997 | Brown et al. |
| 6,962,810 | B2 | 11/2005 | Fraser et al. |
| 7,105,343 | B1 | 9/2006 | Fraser, Jr. et al. |
| 7,129,083 | B1 | 10/2006 | Handler |
| 2007/0204356 | A1 | 8/2007 | Fraser |

OTHER PUBLICATIONS

Cadinanos et al., "Generation of an Inducible and Optimized PiggyBac Transposon System", Nucleic Acids Research, 2007, pp. 1-8, vol. 35, No. 12, e87.
Ding et al., "Efficient Transposition of the PiggyBac (PB) Transposon in Mammalian Cells and Mice", Cell, Aug. 12, 2005, pp. 473-483, vol. 122, Elsevier Inc.
Lacoste et al., "An Efficient and Reversible Transposable System for Gene Delivery and Lineage-Specific Differentiation in Human Embryonic Stem Cells", Cell Stem Cell, Nov. 6, 2009, p. 568, vol. 5(5), Elsevier Inc.
Lacoste et al., "An Efficient and Reversible Transposable System for Gene Delivery and Lineage-Specific Differentiation in Human Embryonic Stem Cells", Cell Stem Cell, Sep. 4, 2009, pp. 332-342, vol. 5(3).
Maragathavally et al., "Chimeric Most and PiggyBac Transposases Result in Site-Directed Integration", The FASEB Journal, Sep. 2006, pp. E1188-E1195, vol. 20(11).
Shi et al., "Construction and Characterization of new PiggyBac Vectors for Constitutive or Inducible Expression of Heterologous Gene Pairs and the Identification of a Previously Unrecognized Activator Sequence in PiggyBac", BMC Biotechnology, Jan. 18, 2007, pp. 1-17, vol. 7:5.
Wilson et al., "PiggyBac Transposon-Mediated Gene Transfer in Human Cells", Molecular Therapy, Jan. 2007, pp. 139-145, vol. 15.
Wu et al., "PiggyBac is a Flexible and Highly Active Transposon as Compared to Sleeping Beauty, Tol2, and Mos1 in Mammalian Cells", Pnas, Oct. 10, 2006, pp. 15008-15013, vol. 103, No. 41.
Lacoste et al., "An Efficient and Reversible Transposable System for Gene Delivery and Lineage-Specific Differentiation in Human Embryonic Stem Cells", Cell Stem Cell, Nov. 6, 2009, p. 568, vol. 5(5), Supplemental Data, Elsevier Inc.

*Primary Examiner* — Jennifer Dunston
(74) *Attorney, Agent, or Firm* — Thompson Coburn LLP; Charles P. Romano

(57) ABSTRACT

PiggyBac transposons and transposases with enhanced transposition activity in cells are provided. Also provided are associated methods and kits for both introducing exogenous DNA inserts into the genomes of host cells as well as for the removal of the inserts from the host cell genomes. Cells obtained by use of the compositions, methods and kits are also provided.

17 Claims, 30 Drawing Sheets

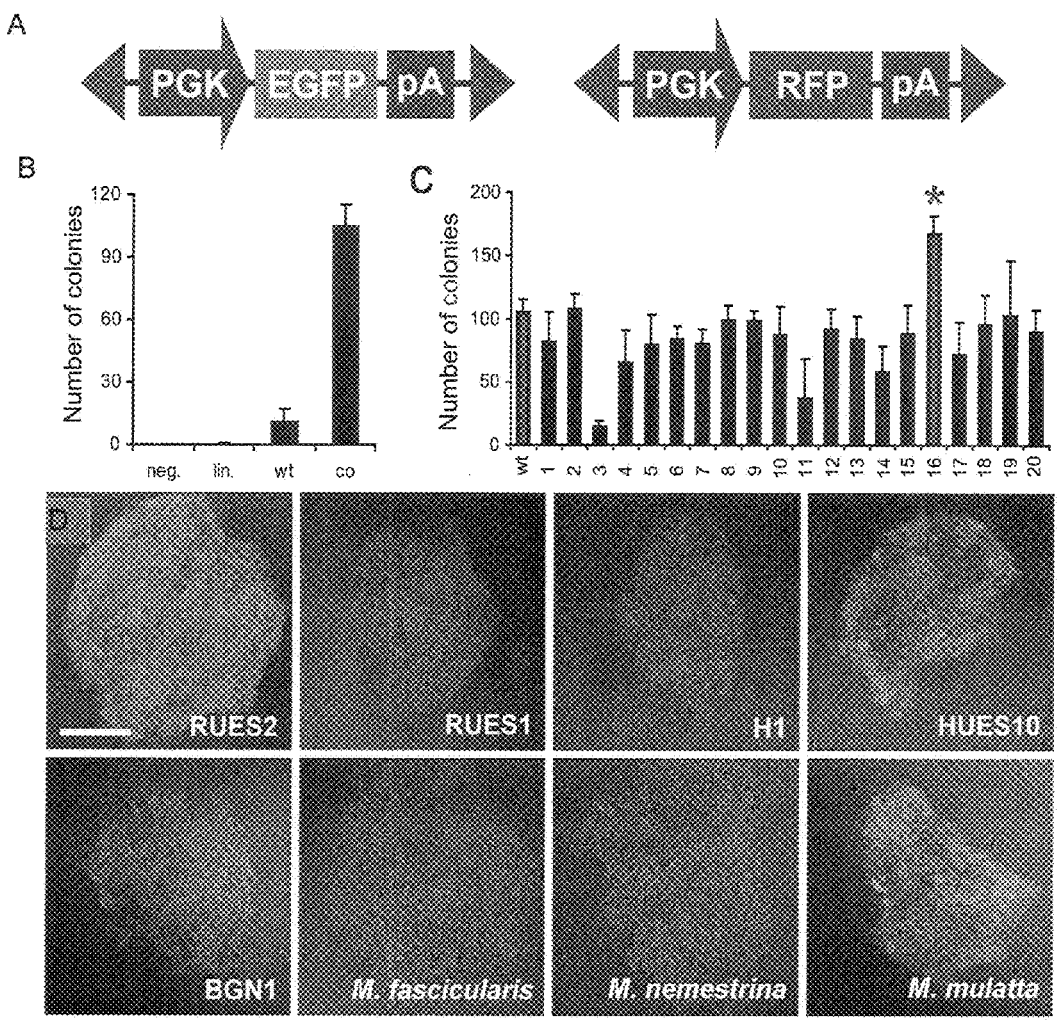
FIGURE 1 A,B,C,D

E
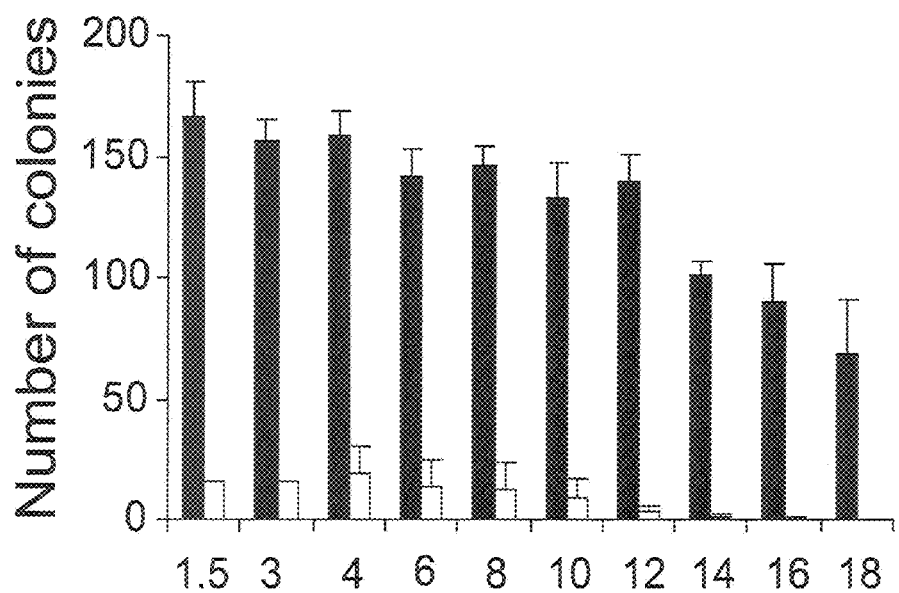
F
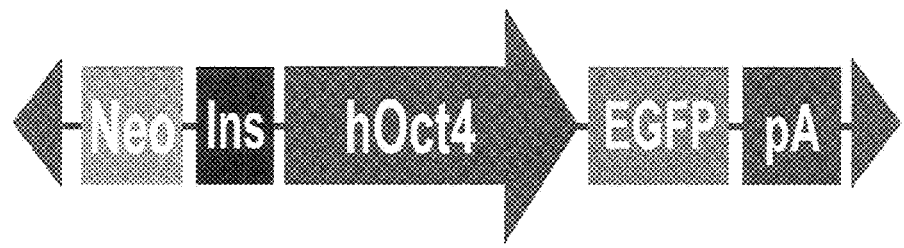
FIGURE 1 E,F

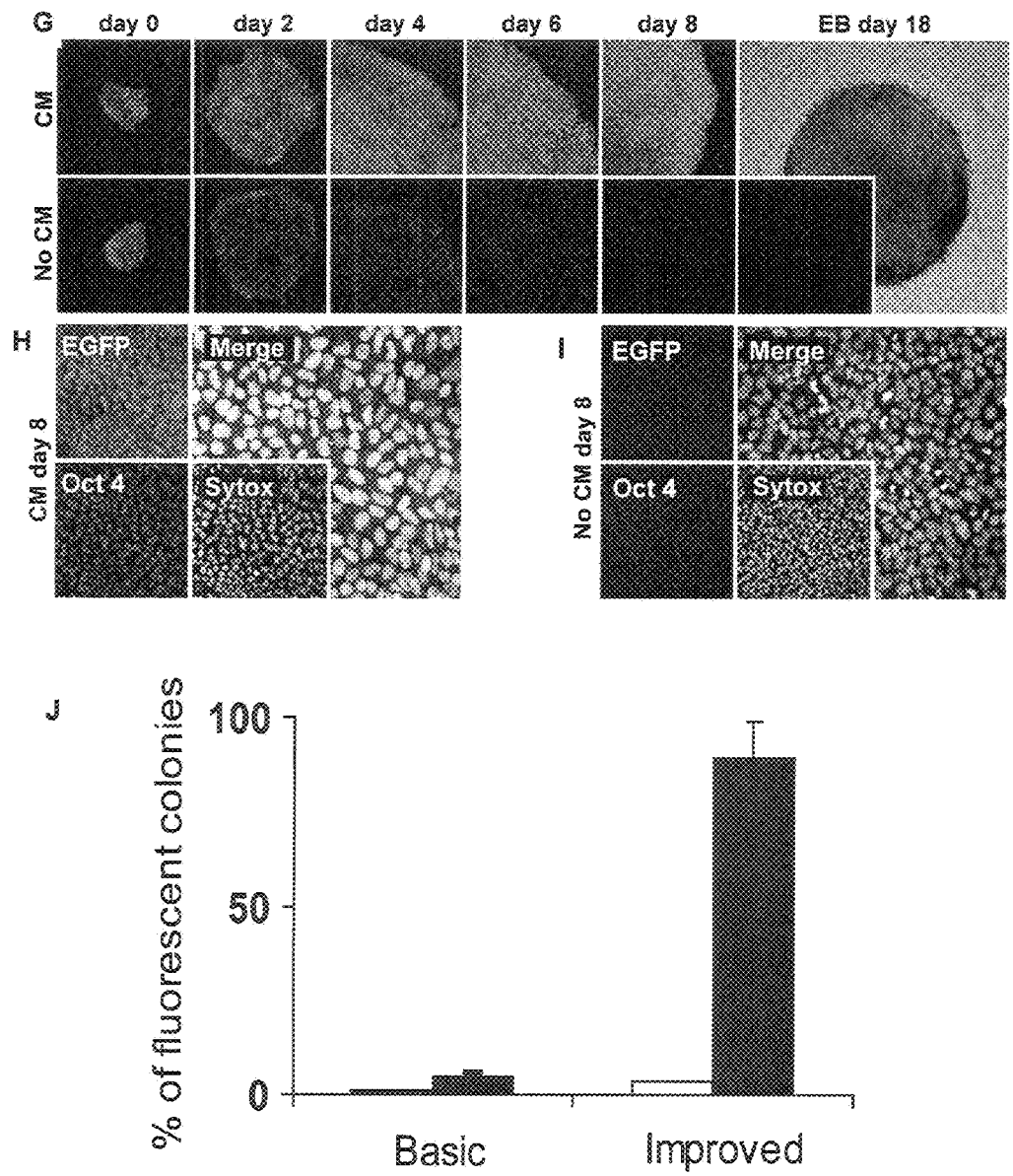
FIGURE 1 G,H,I,J

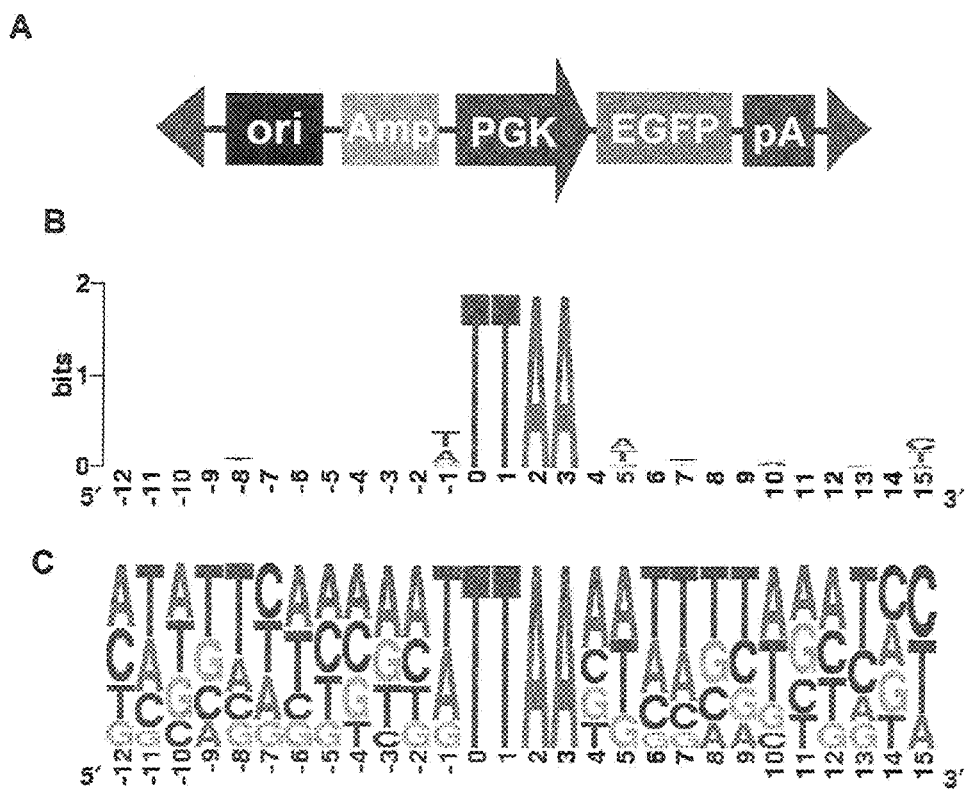
FIGURE 2 A,B,C

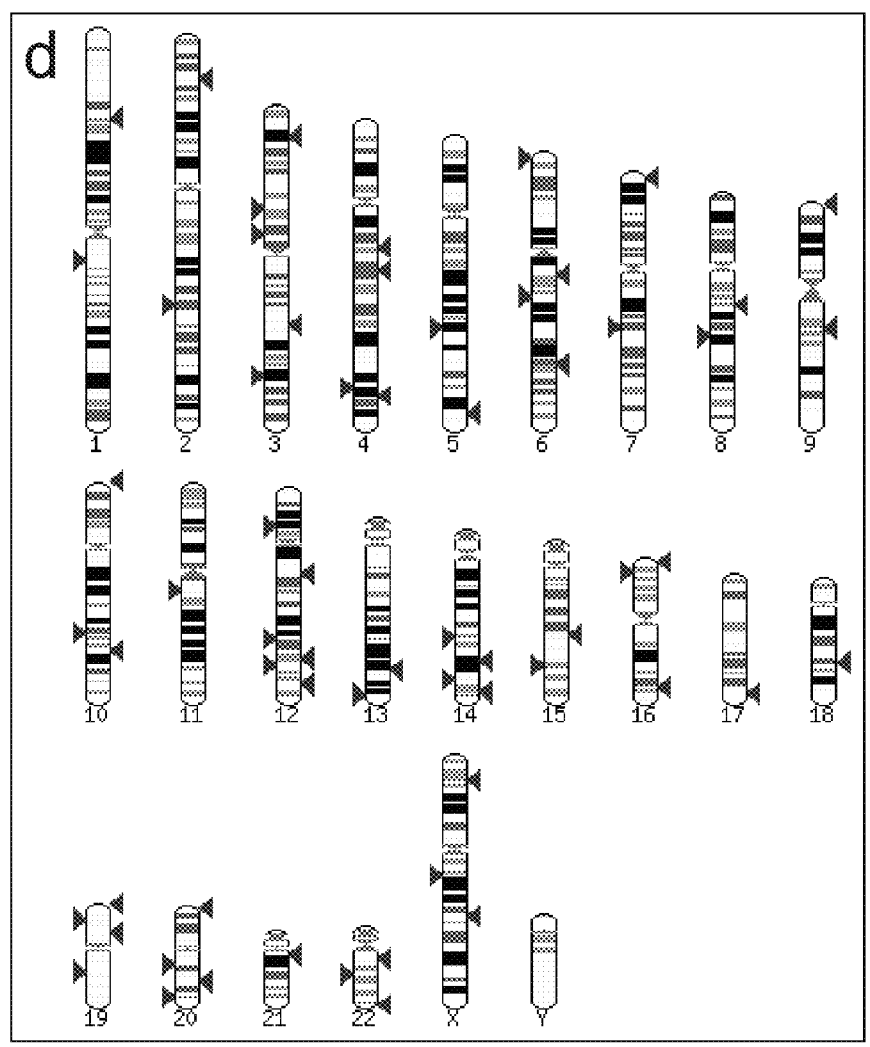
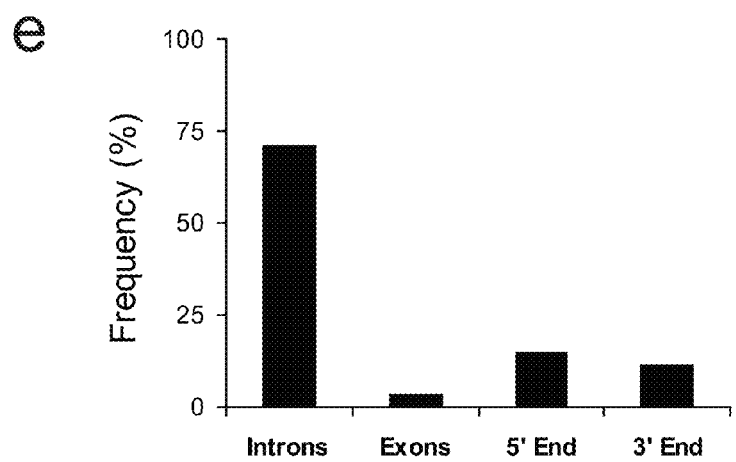
FIGURE 2 d,e

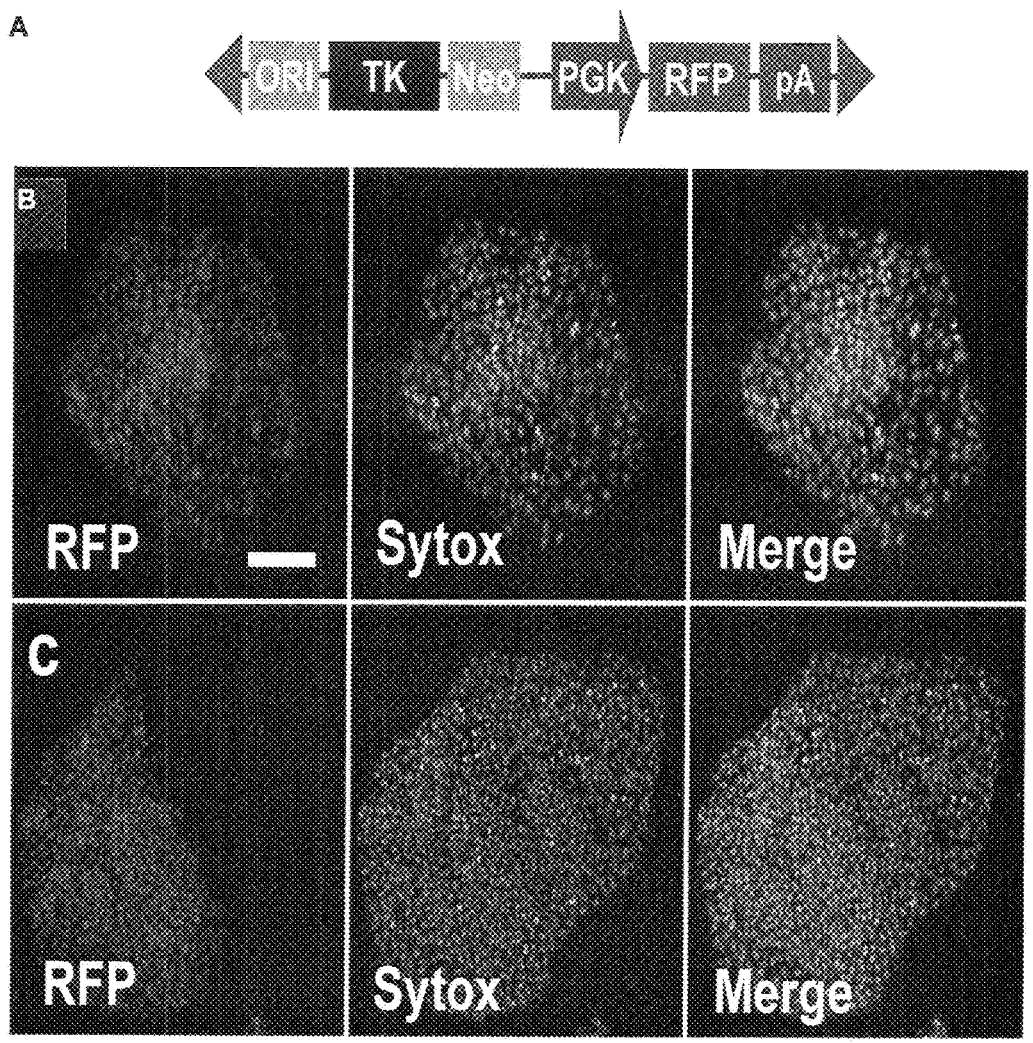
FIGURE 3 A,B,C

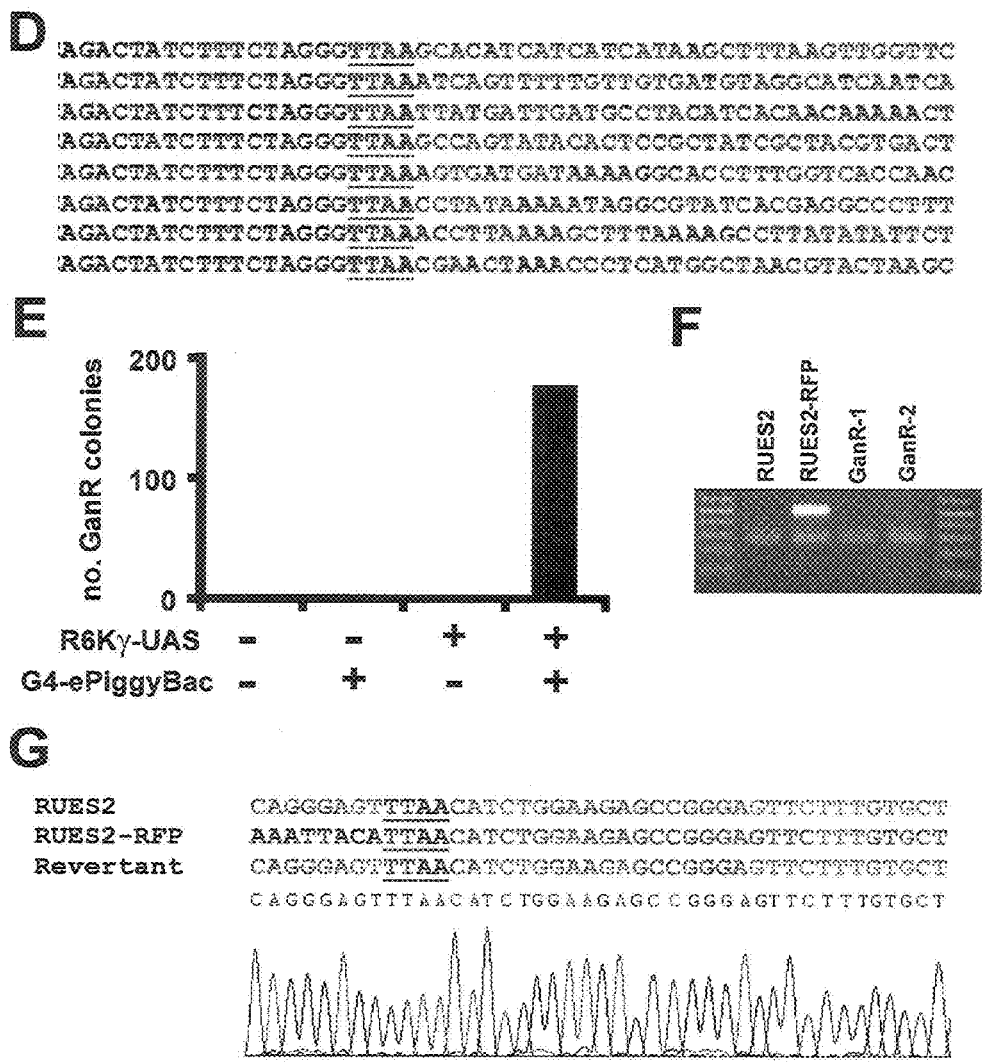
FIGURE 3 D, E, F, G

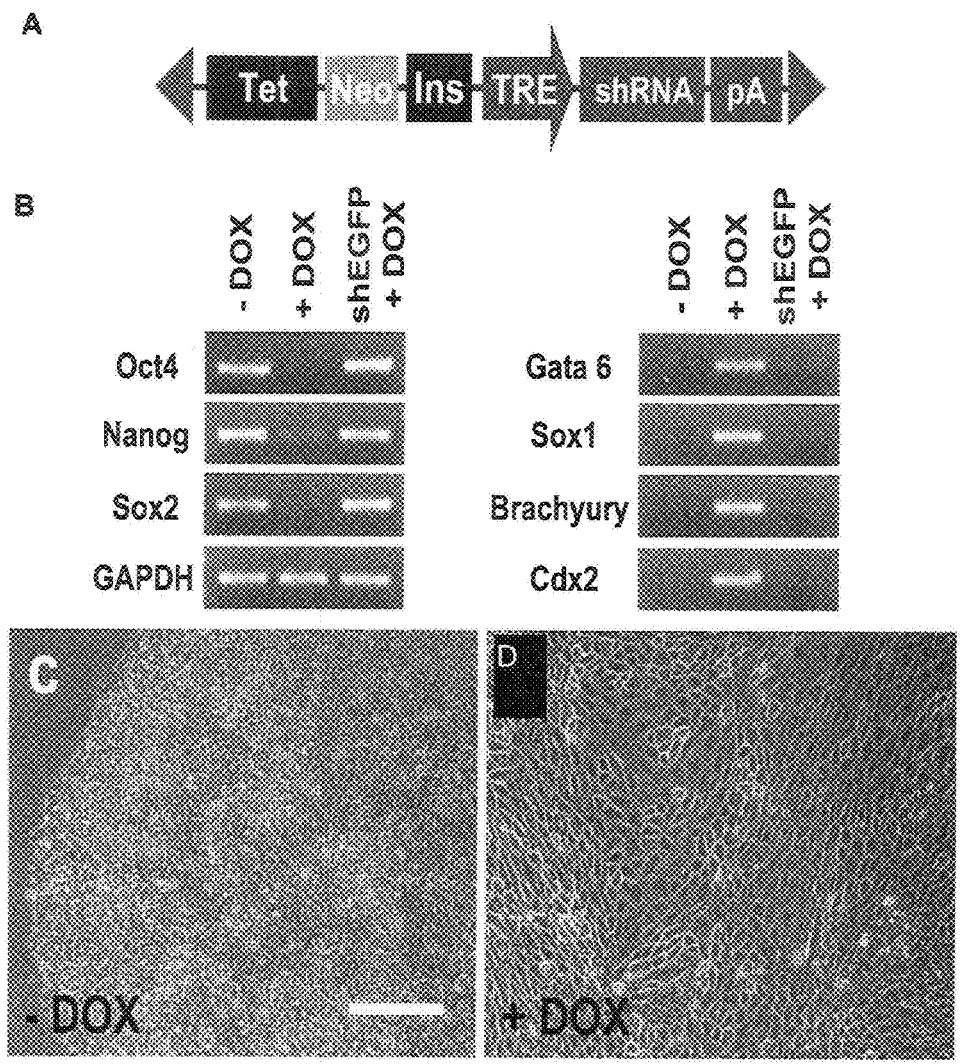
FIGURE 4 A,B,C,D

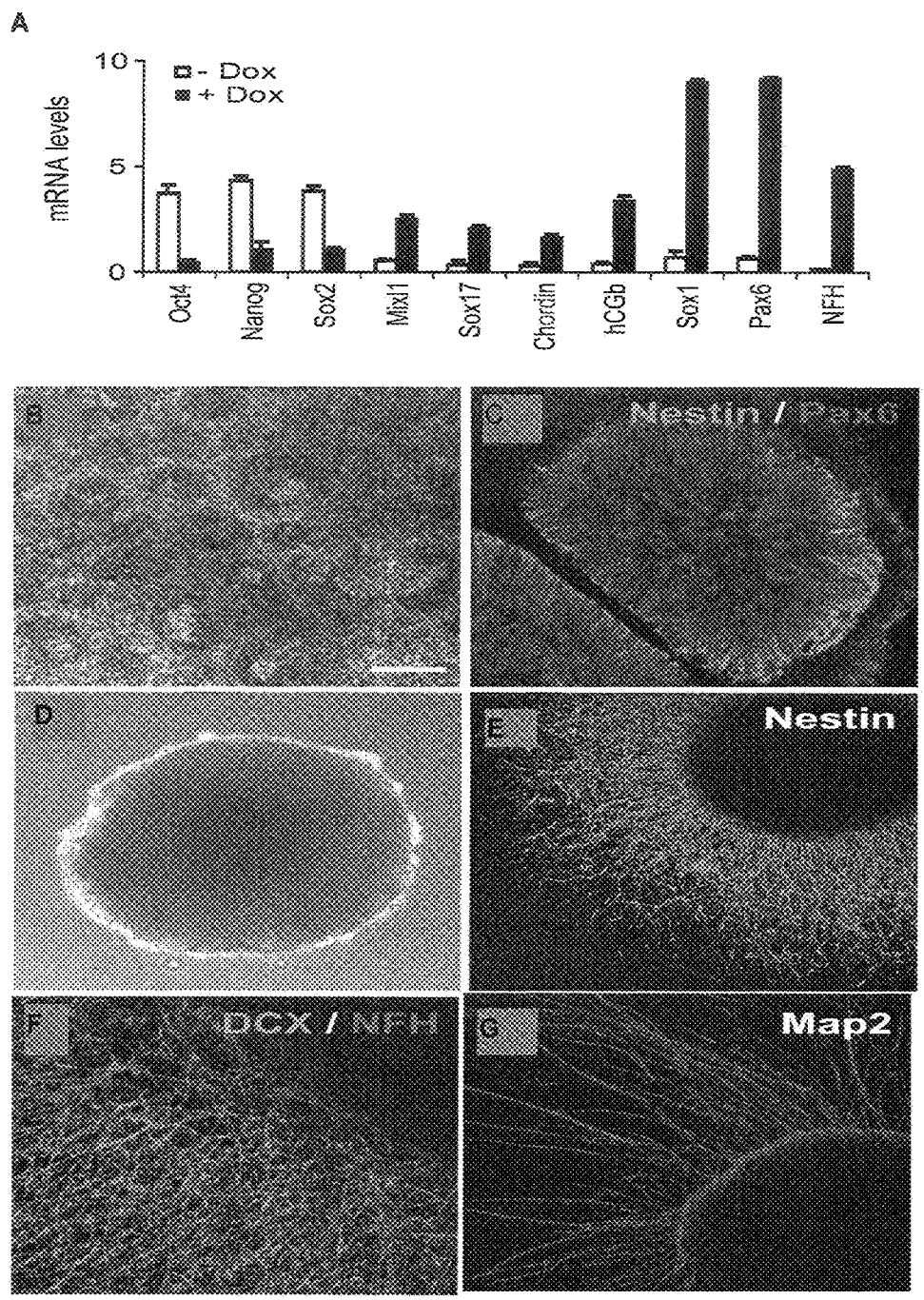
FIGURE 5 A,B,C,D,E,F,G

```
>ePiggyBac
ATGGGCAGCAGCCTGGACGACGAGCACATCCTGAGCGCCCTGCTCCAGAGCGACGACGAGCTGGTGGGCGAGGACAGCGACAGCGAGA
TCAGCGACCACGTGAGCGAGGACGACGTGCAGAGCGACACCGAGGAAGCCTTCATCGACGAGGTGCACGAGGTGCAGCCCACCAGCAG
CGGCAGCGAGATCCTGGACGAGCAGAACGTGATCGAGCAGCCCGGCAGCAGCCTGGCCAGCAACAAGATCCTGACCCTGCCCCAGCGC
ACCATCCGGGGCAAGAACAAGCACTGCTGGAGCACCAGCAAGAGCACCCGCCGCAGCCGCGTGAGCGCCCTGAACCACGTGCGCAGCC
AGCGCGGCCCCACCCGCATGTGCCGCAACATCTACGACCCCCTGCTGTGCTTCAAGCTGTTCTTCACCGACGAGATCATCAGCGAGAT
CGTGAAGTGGACCAACGCCGAGATCAGCCTGAAGCGCCGCGAGAGCATGACCGGCGCCACCTTCCGCGACACCAACGAGGACGAAATC
TACCCCTTCTTCGGCATCCTGGTGATGACCGCCGTGCGCAAGGACAACCACATGAGCACCGACGACCTGTTCGACCGCAGCCTGAGCA
TGGTGTACGTGAGCGTGATGAGCCGCGACCGCTTCGACTTCCTGATCCGGTGCCTGCGCATGGACGACAAGAGCATCCGCCCCACCCT
GCGCGAGAACGACGTGTTCACCCCCGTGCGCAAGATCTGGGACCTGTTCATCCACCAGTGCATCCAGAACTACACCCCCGGCGCCCAT
CTGACCATCGACGAGCAGCTGCTGGGCTTCCGCGGGCGCTGCCCCTTCCGCATGTACATCCCCAACAAGCCCAGCAAGTACGGCATCA
AGATCCTGATGATGTGCGACAGCGGCACCAAGTACATGATCAACGGCATGCCCTACCTGGGCCGCGGCACCCAGACCAACGGCGTGCC
CCTGGGCGAGTACTACGTGAAGGAGCTGAGCAAGCCCGTGCACGGCAGCTGCCGCAACATCACCTGCGACAACTGGTTCACCAGCATC
CCCCTGGCCAAGAACCTGCTCCAGGAGCCCTACAAGCTGACCATCGTGGGCACCGTGCGCAGCAACAAGCGCGAGATCCCCGAGGTGC
TGAAGAACAGCCGCAGCCGCCCCGTGGGCACCAGCATGTTCTGCTTCGACGGCCCCCTGACCCTGGTGAGCTACAAGCCCAAGCCCGC
CAAGATGGTGTACCTGCTGAGCAGCTGCGACGAGGACGCCCAGCATCAACGAGAGCACCGGCAAGCCCCAGATGGTGATGTACTACAAC
CAGACCAAGGGCGGCGTGGACACCCTGGACCAGATGTGCAGCGTGATGACCTGCTCCCGCAAGACCAACCGCTGGCCGATGGCCCTGC
TGTACGGCATGATTAACATCGCCTGCATCAACAGCTTCATCATCTACAGCCACAACGTGAGCAGCAAGGGCGAGAAGGTGCAGAGCCG
CAAGAAGTTCATGCGCAACCTGTACATGAGCCTGACCAGCAGCTTCATGCGCAAGCGCCTGGAGGCCCCCACCCTGAAGCGCTACCTG
CGCGACAACATCAGCAACATCCTGCCCAACGAGGTGCCCGGCACCAGCGACGACAGCACCGAGGAGCCCGTGACCAAGAAGCGCACCT
ACTGCACCTACTGCCCCAGCAAGATCCGCCGCAAGGCCAACGCCAGCTGCAAGAAGTGCAAGAAGGTGATCTGCCGCGAGCACAACAT
CGACATGCAGAGCTGCTTCTAA
```

|  | 1 | | | | | | 70 |
|---|---|---|---|---|---|---|---|
| wtPiggyBac | MGSSLDDEHI | LSALLQSDDE | LVGEDSDSEI | SDHVSEDDVQ | SDTEEAFIDE | VHEVQPTSSG | SEILDEQNVI |
| ePiggyBac | MGSSLDDEHI | LSALLQSDDE | LVGEDSDSEI | SDHVSEDDVQ | SDTEEAFIDE | VHEVQPTSSG | SEILDEQNVI |

|  | 71 | | | | | | 140 |
|---|---|---|---|---|---|---|---|
| wtPiggyBac | EQPGSSLASN | KILTLPQRTI | RGKNKHCWST | SKSTRRSRVS | ALNHVRSQRG | PTRMCRNIYD | PLLCFKLFFT |
| ePiggyBac | EQPGSSLASN | KILTLPQRTI | RGKNKHCWST | SKSTRRSRVS | ALNHVRSQRG | PTRMCRNIYD | PLLCFKLFFT |

|  | 141 | | | | | | 210 |
|---|---|---|---|---|---|---|---|
| wtPiggyBac | DEIISEIVKW | TNAEISLKRR | ESMTGATFRD | TNEDEIYAFF | GILVMTAVRK | DNHMSTDDLF | DRSLSMVYVS |
| ePiggyBac | DEIISEIVKW | TNAEISLKRR | ESMTGATFRD | TNEDEIYAFF | GILVMTAVRK | DNHMSTDDLF | DRSLSMVYVS |

|  | 211 | | | | | | 280 |
|---|---|---|---|---|---|---|---|
| wtPiggyBac | VMSRDRFDFL | IRCLRMDDKS | IRPTLRENDV | FTPVRKIWDL | FIHQCIQNYT | PGAHLTIDEQ | LLGFRGRCPF |
| ePiggyBac | VMSRDRFDFL | IRCLRMDDKS | IRPTLRENDV | FTPVRKIWDL | FIHQCIQNYT | PGAHLTIDEQ | LLGFRGRCPF |

|  | 281 | | | | | | 350 |
|---|---|---|---|---|---|---|---|
| wtPiggyBac | RMYIPNKPSK | YGIKILMMCD | SGTKYMINGM | PYLGRGTQTN | GVPLGEYYVK | ELSKPVHGSC | RNITCDNWFT |
| ePiggyBac | RMYIPNKPSK | YGIKILMMCD | SGTKYMINGM | PYLGRGTQTN | GVPLGEYYVK | ELSKPVHGSC | RNITCDNWFT |

|  | 351 | | | | | | 420 |
|---|---|---|---|---|---|---|---|
| wtPiggyBac | SIPLAKNLLQ | EPYKLTIVGT | VRSNKREIPE | VLKNSRSRPV | GTSMFCFDGP | LTLVSYKPKP | AKMVYLLSSC |
| ePiggyBac | SIPLAKNLLQ | EPYKLTIVGT | VRSNKREIPE | VLKNSRSRPV | GTSMFCFDGP | LTLVSYKPKP | AKMVYLLSSC |

|  | 421 | | | | | | 490 |
|---|---|---|---|---|---|---|---|
| wtPiggyBac | DEDASINEST | GKPQMVMYYN | QTKGGVDTLD | QMCSVMTCSR | KTNRWPMALL | YGMINIACIN | SFIIYSHNVS |
| ePiggyBac | DEDASINEST | GKPQMVMYYN | QTKGGVDTLD | QMCSVMTCSR | KTNRWPMALL | YGMINIACIN | SFIIYSHNVS |

|  | 491 | | | | | | 560 |
|---|---|---|---|---|---|---|---|
| wtPiggyBac | SKGEKVQSRK | KFMRNLYMSL | TSSFMRKRLE | APTLKRYLRD | NISNILPNEV | PGTSDDSTEE | PVTKKRTYCT |
| ePiggyBac | SKGEKVQSRK | KFMRNLYMSL | TSSFMRKRLE | APTLKRYLRD | NISNILPNEV | PGTSDDSTEE | PVTKKRTYCT |

|  | 561 | | 594 | | |
|---|---|---|---|---|---|
| wtPiggyBac | YCPSKIRRKA | NASCKKCKKV | ICREHNIDMC | QSCF |
| ePiggyBac | YCPSKIRRKA | NASCKKCKKV | ICREHNIDMC | QSCF |

Figure 6

```
>5'TR-mutant16
GATATCTATAACAAGAAAATATATATATAATAAGTTATCACGTAAGTAGAACACGAAATAACAATATAATTATCGTA
TGAGTTAAATCTTAAAAGTCACGTAAAAGATAATCATGCGTCATTTTGACTCACGCGGTTGTTATAGTTCAAAATCA
GTGACACTTACCGCATTGACAAGCACGCCTCACGGGAGCTCCAAGCGGCGACTGAGATGTCCTAAATGCACAGCGAC
GGATTCGCGCTATTTAGAAAGAGAGAGCAATATTTCAAGAATGCATGCGTCAATTTTACGCAGACTATCTTTCTAGG
GTTAA
```

```
              1                                                    T54C      60
          wt  GATATCTATA ACAAGAAAAT ATATATATAA TAAGTTATCA CGTAAGTAGA ACATGAAATA
    mutant16  GATATCTATA ACAAGAAAAT ATATATATAA TAAGTTATCA CGTAAGTAGA ACACGAAATA 61                                                             120
          wt  ACAATATAAT TATCGTATGA GTTAAATCTT AAAAGTCACG TAAAAGATAA TCATGCGTCA
    mutant16  ACAATATAAT TATCGTATGA GTTAAATCTT AAAAGTCACG TAAAAGATAA TCATGCGTCA 121           C137T                                              180
          wt  TTTTGACTCA CGCGGTCGTT ATAGTTCAAA ATCAGTGACA CTTACCGCAT TGACAAGCAC
    mutant16  TTTTGACTCA CGCGGTTGTT ATAGTTCAAA ATCAGTGACA CTTACCGCAT TGACAAGCAC 181                                                              240
          wt  GCCTCACGGG AGCTCCAAGC GGCGACTGAG ATGTCCTAAA TGCACAGCGA CGGATTCGCG
    mutant16  GCCTCACGGG AGCTCCAAGC GGCGACTGAG ATGTCCTAAA TGCACAGCCA CGGATTCGCG 241                                                              300
          wt  CTATTTAGAA AGAGAGAGCA ATATTTCAAG AATGCATGCG TCAATTTTAC GCAGACTATC
    mutant16  CTATTTAGAA AGAGAGAGCA ATATTTCAAG AATGCATGCG TCAATTTTAC GCAGACTATC 301        313
          wt  TTTCTAGGGT TAA
    mutant16  TTTCTAGGGT TAA
```

```
GCAGCTAGATTAACCCTAGAAAGATAGTCTGCGTAAAATTGACGCATGC
ATTCTTGAAATATTGCTCTCTCTTTCTAAATAGCGCGAATCCGTCGCTG
TGCATTTAGGACATCTCAGTCGCCGCTTGGAGCTCCCGTGAGGCGTGCT
TGTCAATGCGGTAAGTGCTACTGATTTGAACTATAACAACCGCGTGAG
TCAAAATGACGCATGATTATCTTTTACGTGACTTTAAGATTTAACTCA
TACGATAATTATATTGTTATTTCGTGTTCTACTTACGTGATAACTTATT
ATATATATATTTTTCTTGTTATAGATATCCTTCTCGAGGGATCCAAGCTT
ATCGATGCGGCCGCGACTCTAGATCATAATCAGCCATACCACATTTGTAGAGGTTTTA
CTTGCTTTAAAAAACCTCCCACACCTCCCCCTGAACCTGAAACATAAAATGAATGCAATTG
TTGTTGTTAACTTGTGTTATTGCAGCTTATAATGGTTACAAATAAAGCAATAGCATCACAAA
TTTCACAAATAAAGCATTTTTTTCACTGCATTCTAGTTGTGGTTTGTCCAAACTCATCAAT
GTATCTTAAGGAATTCGATAAAGTTTGTTACTTTATAGAAGAAATTTTG
AGTTTTTGTTTTTTTTTAATAAATAAGTAATGATGAACATAAAATTGTTTGT
TGAATTTATTATTAGTATGTAAATAAAATCGATATAAACCTCTAATATCT
ATTCAAATTAATAAATAAACCTCGATATCTTTAACGTCGATAAAACACATGC
GTCAATTTTACGCATGATTATCTTTAACGTACGTCACAATATGATTATC
TTTCTAGGGTTAATCTAGCTGC
```

FIG. 20

|          | 1                                                                                                          | 70 |
|----------|------------------------------------------------------------------------------------------------------------|----|
| wt       | GATATCTATA ACAAGAAAAT ATATATATAA TAAGTTATCA CGTAAGTAGA ACATGAAATA ACAATATAAT |
| mutant1  | GATATCTATA ACAAGAAAAT ATATATATAA TAAGTTATCA CGTAAGTAGA TCATGAAATA ACAATATAAT |
| mutant20 | GATATCTATA ACAAGAAAAT ATATATATAA TAAGTTATCA CGTAAGTAGA TCATGAAATA ACAATATAAT |
| mutant5  | GATATCTATA ACAAGAAAAT ATATATATAA TAAGTTATCA CGTAAGTAGA ACATGAAATA ACAATATAAT |
| mutant14 | GATATCTATA ACAAGAAAAT ATATATATAA TAAGTTATCA CGTAAGTAGA ACATGAAATA ACAATATAAT |
| mutant6  | GATATCTATA ACAAGAAAAT ATATATATAA TAAGTTATCA CGTAAGTAGA ACATGAAATA ACAATATAAT |
| mutant7  | GATATCTATA ACAAGAAAAT ATATATATAA TAAGTTATCA CGTAAGTAGA ACATGAAATA ACAATATAAT |
| mutant10 | GATATCTATA ACAAGAAAAT ATATATATAA TAAGTTATCA CGTAAGTAGA ACATGAAATA ACAATATAAT |
| mutant17 | GATATCTATA ACAAGAAAAT ATATATATAA TAAGTTATCA CGTAAGTAGA ACATGAAATA ACAATATAAT |
| mutant15 | GATATCTATA ACAAGAAAAT ATATATATAA TAAGTTATCA CGTAAGTAGA ACATGAAATA ACAATATAAT |
| mutant12 | GATATCTATA ACAAGAAAAT ATATATATAA TAAGTTATCA CGTAAGTAGA ACATGAAATA ACAATATAAT |
| mutant2  | GATATCTATA ACAAGAAAAT ATATATATAA TAAGTTATCA CGTAAGTAGA ACATGAAATA ACAATATAAT |
| mutant4  | GATATCTATA ACAAGAAAAT ATATATATAA TAAGTTATCA CGTAAGTAGA ACATGAAATA ACAATATAAT |
| mutant11 | GATATCTATA ACAAGAAAAT ATATATATAA TAAGTTATCA CGTAAGTAGA ACATGAAATA ACAATATAAT |
| mutant19 | GATATCTATA ACAAGAAAAT ATATATATAA TAAGTTATCA CGTAAGTAGA ACATGAAATA ACAATATAAT |
| mutant8  | GATATCTATA ACAAGAAAAT ATATATATAA TAAGTTATCA CGTAAGTAGA ACATGAAATA ACAATATAAT |
| mutant13 | GATATCTATA ACAAGAAAAT ATATATATAA TAAGTTATCA CGTAAGTAGA ACATGAAATA ACAATATAAT |
| mutant9  | GATATCTATA ACAAGAAAAT ATATATATAA TAAGTTATCA CGTAAGTAGA ACATGAAATA ACAATATAAT |
| mutant3  | GATATCTATA ACAAGAAAAT ATATATATAA TAAGTTATCA CGTAAGTAGA ACATGAAATA ACAATATAAT |
| mutant16 | GATATCTATA ACAAGAAAAT ATATATATAA TAAGTTATCA CGTAAGTAGA ACACGAAATA ACAATATAAT |
| mutant18 | GATATCTATA ACAAGAAAAT ATATATATAA TAAGTTATCA CGTAAGTAGA ACATGAAATA ACAATATAAT |

FIG. 21A

|          | 71                                                                                       | 140 |
|----------|------------------------------------------------------------------------------------------|-----|
| wt       | TATCGTATGA GTTAAATCTT AAAAGTCACG TAAAAGATAA TCATGCGTCA TTTTGACTCA CGCGGTCGTT |     |
| mutant1  | TATCGTATGA GTTAAATCTT AAAAGTCACG TAAAAGATAA TCATGCGTCA TTTTGACTCA CGCGGTCGTT |     |
| mutant20 | TATCGTATGA GTTAAATCTT AAAAGTCACG TAAAAGATAA TCATGCGTCA TTTTGACTCA CGCGGTCGTT |     |
| mutant5  | TATCGTATGA GTTAAATCTT AAAAGTCACG TAAAAGATAA TCATGCGTCA TTTTGCCTCA CGCGGTCGTT |     |
| mutant14 | TATCGTATGA GTTAAATCTT AAAAGTCACG TAAAAGATAA TCATGCGTCT TTTTGACTCA CGCGGTCGTT |     |
| mutant6  | TATCGTATGA GTTAAATCTT AAAAGTCACG TAAAAGATAA ACATGCGTCA TTTTGACTCA CGCGGTCGTT |     |
| mutant7  | TATCGTATGA GTTAAATCTT AAAAGTCACG TAAAAGATAA TCATGCGTCA TTTTGACTCA CGCGGTCGTT |     |
| mutant10 | TATCGTATGA GTTAAATCTT AAAAGTCACG AAAAAGATAA TCATGCGTCA TTTTGACTCA CGCGGTCGTT |     |
| mutant17 | TATCGTATGA GTTAAATCTT AAAAGTCACG TATCAGATAA TCATGCGTCA TTTTGACTCA CGCGGTCTTT |     |
| mutant15 | TATCGTATGA GTTAAATCTT AAAAGTCACG TAAAAGATAA TCATGCGTCA TTTTGACTCA CGCGGTCGTT |     |
| mutant12 | TATCGTATGA GTTAAATCTT AAAAGTCACG TAAAAGATAA TCATGCGTCA TTTTGACTCA CGCGGTCGTT |     |
| mutant2  | TATCGTATGA GTTAAATCTT AAAAGTCACG TAAAAGATAA TCATGCGTCA TTTTGACTCA CGCGGTCGTT |     |
| mutant4  | TATCGTATGA GTTAAATCTT AAAAGTCACG TAAAAGATAA TCATGCGTCA TTTTGACTCA CGCGGTCGTT |     |
| mutant11 | TATCGTATGA GTTAAATCTT AAAAGTCACG TAAAAGATAA TCATGCGTCA TTTTGACTCA CGCGGTCGTT |     |
| mutant19 | TATTGTATGA GTTAAATCTT AAAAGTCACG TAAAAGATAA TCATGCGTCA TTTTGACTCA CGCGGTCGTT |     |
| mutant8  | TATCGTATGA GTTAAATCTT AAAAGTCACG TAAAAGATAA TCATGCGTCA TTTTGACTCA CGCGGTCGTC |     |
| mutant13 | TATCGTATGA GTTAAATCTT AAAAGTCACG TAAAAGATAA TCATGCGTCA TTATGACTCA CGCGGTCGTT |     |
| mutant9  | TATCGTATGA GTTAAATCTT AAAAGTCACG TAAAAGATAA TCATGCGTCA TTCGGACTCA CGCGGTCGTT |     |
| mutant3  | TATCGTATGA GTTAAATCTT AAAAGTCACG TAAAAGATAA TCATGCGTCA TTTTGACTCA CGCGGTTGTT |     |
| mutant16 | TATCGTATGA GTTAAATCTT AAAAGTCACG TAAAAGATAA TCATGCGTCA TTTTGACTCA CGCGGTCGTT |     |
| mutant18 | TATCGTATGA GTTAAATCTT AAAAGTCACG TAAAAGATAA TCATGCGACA TTTTGACTCA CGCGGTCGTT |     |

FIG. 21B

|          | 141        |            |            |            |            |            | 210        |
|----------|------------|------------|------------|------------|------------|------------|------------|
| wt       | ATAGTTCAAA | ATCAGTGACA | CTTACCGCAT | TGACAAGCAC | GCCTCACGGG | AGCTCCAAGC | GGCGACTGAG |
| mutant1  | ATAGTTCAAA | ATCAGTGACA | CTTACCGCAT | TGACAAGCAC | GCCTCACGGG | AGCTCCAAGC | GGCGACTGAG |
| mutant20 | ATAGTTCAAA | ATCAGTGACA | CTTACCGCAT | TGACAAGCCC | GCCTCACGGG | AGCTCCAAGC | GGCGACTGAG |
| mutant5  | ATAGTTCAAA | ATCAGTGACA | CTTACCGCAT | TGACAAGCAC | GCCTCACGGG | AGCTCCAAGC | GGCGACTGAG |
| mutant14 | ATAGTTCAAA | ATCAGTGACA | CTTACCGCAT | TGACAAGCAC | GCCTCACGGG | AGCTCCAAGC | GGCGACTGAG |
| mutant6  | AAAGTTCAAA | ATCAGTGACA | CTTACCGCAT | TGACAAGCAC | GCCTCACGGG | AGCTCCAAGC | GGCGACTGAG |
| mutant7  | ATAGTTCAAA | ATCAGTGACA | CTTACCGCAT | TGACAAGCAC | GCCTCACGGG | AGCTCCAAGC | GGCGACTGAG |
| mutant10 | ATAGTTCAAA | ATCAGTGACA | CTTACCGCAT | TGACAAGCAC | GCCTCACGGG | AGCTCCAAGC | GGCGACTGAG |
| mutant17 | ATAGTTCAAA | ATCAGTGACA | CTTACCGCAT | TGACAAGCAC | GCCTCACGGG | AGCTCCAAGC | GGCGACTGAG |
| mutant15 | ATAGTTCAAA | ATCAGTGACA | CTTACCGCAT | TGACAAGCAC | GCCTCACGGG | AGCTCCAAGC | GGCGACTGAG |
| mutant12 | ATAGTTCAAA | ATAAGTGACA | CTTACCGCAT | TGACAAGCAC | GCCTCACGGG | AGCTCCAAGC | GGCGACTGAG |
| mutant2  | ATAGTTCAAA | ATCAGTGACA | CTTACCGCAT | TGACAAGCAC | GCCTCACGGG | AGCTCCAAGC | GGCGACTGAG |
| mutant4  | ATAGTTCAAA | ATCAGTGACA | CTTACCGCAT | TGACAAGCAC | GCCTCACGGG | AGCTCCAAGC | GGCGACTGAG |
| mutant11 | ATAGTTCAAA | ATCAGTGACA | CTTACCGCAT | TGACAAGCAC | GCCTCACGGG | AGCTCCAAGC | GGCGACTGAC |
| mutant19 | ATAGTTCAAA | ATCAGTGACA | CTTACCGCAT | TGACAAGCAC | GCCTCACGGG | AGCTCCAAGC | GGCGACTGAG |
| mutant8  | ATAGTTCAAA | ATCAGTGACA | CTTACCGCAT | TGACAAGCAC | GCCTCACGGG | AGCTCCAAGC | GGCGACTGAG |
| mutant13 | ATAGTTCAAA | ATCAGTGACA | CTTACCGCAT | TGACAAGCAC | GCCTCACGGG | AGCTCCAAGC | GGCGACTGAG |
| mutant9  | ATAGTTCAAA | ATCAGTGACA | CTTACCGCAT | TGACAAGCAC | GCCTCACGGG | AGCTCCAAGC | AACGACTGAG |
| mutant3  | ATAGTTCAAA | ATCAGTGACA | CTTACCGCAT | TGACAAGCAC | GCCTCACGGG | AGCTCCAAGC | GGCGACTGAG |
| mutant16 | ATAGTTCAAA | ATCAGTGACA | CTTACCGCAT | TGACAAGCAC | GCCTCACGGG | AGCTCCAAGC | GGCGACTGAG |
| mutant18 | ATAGTTCAAA | ATCAGTGACA | CTTACGGCAT | TGACAAGCAC | GCCTCACGGG | AGCTCCAAGC | GGCGACTGAG |

FIG. 21C

|          | 211        |            |            |            |            |            | 280        |
|----------|------------|------------|------------|------------|------------|------------|------------|
| wt       | ATGTCCTAAA | TGCACAGCGA | CGGATTCGCG | CTATTTAGAA | AGAGAGAGCA | ATATTTCAAG | AATGCATGCG |
| mutant1  | ATGTCCTAAA | TGCACAGCGA | CGGATTCGCG | CTATTTAGAA | AGAGAGAGCA | ATATTTCAAG | AATGCATGCG |
| mutant20 | ATGTCCTAAA | TGCACAGCGA | CGGATTCGCG | CTATTTAGAA | AGAGAGAGCA | ATATTTCAAG | AATGCATGCG |
| mutant5  | ATGTCCTAAA | TGCACAGCGA | CGGATTCGCG | CTATTTAGAA | AGAGAGAGCA | ATATTTCAAG | AATGCATGCG |
| mutant14 | ATGTCCTAAA | TGCACAGCGA | CGGATTCGCG | CTATTTAGAA | AGAGAGAGCA | ATATTTCAAG | AATGCATGCG |
| mutant6  | ATGTCCTAAA | TGCACAGCGA | CGGATTCGCG | CTATTTAGAA | AGAGAGAGCA | ATATTTCAAG | AATGCATGCG |
| mutant7  | ATGTCCTAAA | TGCACAGCGA | CGGATTCGCG | CTATTTAGAA | AGAGAGAGCA | ATATTTCAAG | AATGCATGCG |
| mutant10 | ATGTCCTAAA | TGCACAGCGA | CGGATACGCG | CTATTTAGAA | AGAGAGAGCA | ATATTTCAAG | AATGCATGCG |
| mutant17 | ATGTCCTAAA | TGCACAGCGA | CGGATTCGCG | CTATTTAGAA | AGAGAGAGCA | ATATTTCAAG | AATGCATGCG |
| mutant15 | ATGTCCTAAA | TGCACAGCGA | CGGATTCGCG | CTATTTAGAA | AGAGAGAGCA | ATATTTCAAG | AATGCATGCG |
| mutant12 | ATGTCCTAAA | TGCACAGCGA | CGGATTCGCG | CTATTTAGAA | AGAGAGAGCA | ATATTTCAAG | AATGCATGCG |
| mutant2  | ATGTCCTAAA | TGCACAGCGA | CGGATTCGCG | CTATTTAGAA | AGAGAGAGCA | ATATTTCAAG | AATGCATGCG |
| mutant4  | ATGTCCTAAA | TGCACAGCGA | CGGATTCGCG | ATATTTAGAA | AGAGAGAGCA | ATATTTCAAG | AATGCATGCG |
| mutant11 | ATGTCCTAAA | TGCACAGCGA | CGGATTCGCG | CTATTTAGAA | AGAGAGAGCA | ATATTTCAAG | AATGCATGCG |
| mutant19 | ATGTCCTAAA | TGCACAGCGA | CGGATTCGCG | CTATTTAGAA | AGAGAGAGCA | ATATTTCAAG | AATGCATGCG |
| mutant8  | ATGTCCTAAA | TGCACAGCGA | CGGATTTGCG | CTATTTAGAA | AGAGAGAGCA | ATATTTCAAG | AATGCATGCG |
| mutant13 | ATGTCCTAAA | TGCACAGCGA | CGGATTCGCG | CTATTTAGAA | AGAGAGAGCA | ATATTTCAAG | AATGCATGCG |
| mutant9  | ATGTCCTAAA | TGCACAGCGA | CGGATTCGCG | CTATTTAGAA | AGAGAGAGCA | ATATTTCAAG | AATGCATGCG |
| mutant3  | ATGTCCTAAA | TGCACAGCGA | CGGATTCGCG | CTATTTAGAA | AGAGAGAGCA | ATATTTCAAG | AATGCATGCG |
| mutant16 | ATGTCCTAAA | TGCACAGCGA | CGGATTCGCG | CTATTTAGAA | AGAGAGAGCA | ATATTTCAAG | AATGCATGCG |
| mutant18 | ATGTCCTAAA | TGCACAGCGA | CGGATTCGCG | CTATTTAGAA | AGAGAGAGCA | ATATTTCAAG | AATGCATGCG |

FIG. 21D

|  | 281 | | 313 |
|---|---|---|---|
| wt | TCAATTTTAC | GCAGACTATC | TTTCTAGGGT TAA |
| mutant1 | TCAATTTTAC | GCAGACTATC | TTTCTAGGGT TAA |
| mutant20 | TCAATTTTAC | GCAGACTATC | TTTCTAGGGT TAA |
| mutant5 | TCAATTTTAC | GCAGACTATC | TTTCTAGGGT TAA |
| mutant14 | TCAATTTTAC | GCAGACTATC | TTTCTAGGGT TAA |
| mutant6 | TCAATTTTAC | GCAGACTATC | TTTCTAGGGT TAA |
| mutant7 | TCAATTTTAC | GCAGACTATC | TTTCTAGGGT TAA |
| mutant10 | TCAATTTTAC | GCAGACTATC | TTTCTAGGGT TAA |
| mutant17 | TCAATTTTAC | GCAGACTATC | TTTCTAGGGT TAA |
| mutant15 | TCAATTTTAC | GCAGACTATC | TTTCTAGGGT TAA |
| mutant12 | TCAATTTTAC | GCAGACTATC | TTTCTAGGGT TAA |
| mutant2 | TCAATTTTAC | GCAGACTATC | TTTCTAGGGT TAA |
| mutant4 | TCAATTTTAC | GCAGACTATC | TTTCTAGGGT TAA |
| mutant11 | TCAATTTTAC | GCAGACTATC | TTTCTAGGGT TAA |
| mutant19 | TCAATTTTAC | GCAGACTATC | TTTCTAGGGT TAA |
| mutant8 | TCAATTTTAC | GCAGACTATC | TTTCTAGGGT TAA |
| mutant13 | TCAATTTTAC | GCAGACTATC | TTTCTAGGGT TAA |
| mutant9 | TCAATTTTAC | GCAGACTATC | TTTCTAGGGT TAA |
| mutant3 | TCAATTTTAC | GCAGACTATC | TTTCTAGGGT TAA |
| mutant16 | TCAATTTTAC | GCAGACTATC | TTTCTAGGGT TAA |
| mutant18 | TCAATTTTAC | GCAGACTATC | TTTCTAGGGT TAA |

FIG. 21E

SEQUENCE LISTING

```
<160> NUMBER OF SEQ ID NOS: 75

<210> SEQ ID NO 1
<211> LENGTH: 313
<212> TYPE: DNA
<213> ORGANISM: Trichoplusia ni
<220> FEATURE:
<221> NAME/KEY: mutation
<222> LOCATION: (54)..(54)
<223> OTHER INFORMATION: adenine, cytosine, or guanine
<220> FEATURE:
<221> NAME/KEY: mutation
<222> LOCATION: (137)..(137)
<223> OTHER INFORMATION: adenine, guanine, or thymine

<400> SEQUENCE: 1
gatatctata acaagaaaat atatatataa taagttatca cgtaagtaga acavgaaata        60
```

-continued

| | |
|---|---|
| acaatataat tatcgtatga gttaaatctt aaaagtcacg taaaagataa tcatgcgtca | 120 |
| ttttgactca cgcggtdgtt atagttcaaa atcagtgaca cttaccgcat tgacaagcac | 180 |
| gcctcacggg agctccaagc ggcgactgag atgtcctaaa tgcacagcga cggattcgcg | 240 |
| ctatttagaa agagagagca atatttcaag aatgcatgcg tcaattttac gcagactatc | 300 |
| tttctagggt taa | 313 |

<210> SEQ ID NO 2
<211> LENGTH: 313
<212> TYPE: DNA
<213> ORGANISM: Trichoplusia ni

<400> SEQUENCE: 2

| | |
|---|---|
| gatatctata acaagaaaat atatatataa taagttatca cgtaagtaga acatgaaata | 60 |
| acaatataat tatcgtatga gttaaatctt aaaagtcacg taaaagataa tcatgcgtca | 120 |
| ttttgactca cgcggtcgtt atagttcaaa atcagtgaca cttaccgcat tgacaagcac | 180 |
| gcctcacggg agctccaagc ggcgactgag atgtcctaaa tgcacagcga cggattcgcg | 240 |
| ctatttagaa agagagagca atatttcaag aatgcatgcg tcaattttac gcagactatc | 300 |
| tttctagggt taa | 313 |

<210> SEQ ID NO 3
<211> LENGTH: 244
<212> TYPE: DNA
<213> ORGANISM: Trichoplusia ni

<400> SEQUENCE: 3

| | |
|---|---|
| gataaaagtt ttgttacttt atagaagaaa ttttgagttt ttgttttttt ttaataaata | 60 |
| aataaacata aataaattgt tgttgaatt tattattagt atgtaagtgt aaatataata | 120 |
| aaacttaata tctattcaaa ttaataaata aacctcgata tacagaccga taaaacacat | 180 |
| gcgtcaattt tacgcatgat tatctttaac gtacgtcaca atatgattat ctttctaggg | 240 |
| ttaa | 244 |

<210> SEQ ID NO 4
<211> LENGTH: 1785
<212> TYPE: DNA
<213> ORGANISM: Artificial Sequence
<220> FEATURE:
<223> OTHER INFORMATION: synthetic

<400> SEQUENCE: 4

| | |
|---|---|
| atgggcagca gcctggacga cgagcacatc ctgagcgccc tgctccagag cgacgacgag | 60 |
| ctggtgggcg aggacagcga cagcgagatc agcgaccacg tgagcgagga cgacgtgcag | 120 |
| agcgacaccg aggaagcctt catcgacgag gtgcacgagg tgcagcccac cagcagcggc | 180 |
| agcgagatcc tggacgagca gaacgtgatc gagcagcccg gcagcagcct ggccagcaac | 240 |
| aagatcctga ccctgcccca gcgcaccatc cggggcaaga caagcactg ctggagcacc | 300 |
| agcaagagca cccgccgcag ccgcgtgagc gccctgaacc acgtgcgcag ccagcgcggc | 360 |
| cccacccgca tgtgccgcaa catctacgac cccctgctgt gcttcaagct gttcttcacc | 420 |
| gacgagatca tcagcgagat cgtgaagtgg accaacgccg atcagcct gaagcgccgc | 480 |
| gagagcatga ccggcgccac cttccgcgac accaacgagg acgaaatcta cgccttcttc | 540 |
| ggcatcctgg tgatgaccgc cgtgcgcaag gacaaccaca tgagcaccga cgacctgttc | 600 |
| gaccgcagcc tgagcatggt gtacgtgagc gtgatgagcc gcgaccgctt cgacttcctg | 660 |

```
atccggtgcc tgcgcatgga cgacaagagc atccgcccca ccctgcgcga gaacgacgtg    720
ttcacccccg tgcgcaagat ctgggacctg ttcatccacc agtgcatcca gaactacacc    780
cccggcgccc atctgaccat cgacgagcag ctgctgggct tccgcgggcg ctgcccttc     840
cgcatgtaca tccccaacaa gcccagcaag tacggcatca agatcctgat gatgtgcgac    900
agcggcacca agtacatgat caacggcatg ccctacctgg ccgcggcac ccagaccaac     960
ggcgtgcccc tggcgagta ctacgtgaag gagctgagca gcccgtgca cggcagctgc     1020
cgcaacatca cctgcgacaa ctggttcacc agcatccccc tggccaagaa cctgctccag    1080
gagccctaca gctgaccat cgtgggcacc gtgcgcagca caagcgcga gatccccgag     1140
gtgctgaaga cagccgcag ccgccccgtg ggcaccagca tgttctgctt cgacggcccc     1200
ctgaccctgg tgagctacaa gcccaagccc gccaagatgg tgtacctgct gagcagctgc    1260
gacgaggacg ccagcatcaa cgagagcacc ggcaagcccc agatggtgat gtactacaac    1320
cagaccaagg gcgcgtgga cacctggac cagatgtgca gcgtgatgac ctgctcccgc     1380
aagaccaacc gctggccgat ggccctgctg tacggcatga ttaacatcgc ctgcatcaac    1440
agcttcatca tctacagcca caacgtgagc agcaagggcg agaaggtgca gagccgcaag    1500
aagttcatgc gcaacctgta catgagcctg accagcagct tcatgcgcaa cgcctggag    1560
gcccccaccc tgaagcgcta cctgcgcgac aacatcagca catcctgcc caacgaggtg     1620
cccggcacca gcgacgacag caccgaggag cccgtgacca gaagcgcac ctactgcacc     1680
tactgccca gcaagatccg ccgcaaggcc aacgccagct gcaagaagtg caagaaggtg    1740
atctgccgcg agcacaacat cgacatgtgc cagagctgct tctaa                   1785

<210> SEQ ID NO 5
<211> LENGTH: 594
<212> TYPE: PRT
<213> ORGANISM: Trichoplusia ni

<400> SEQUENCE: 5

Met Gly Ser Ser Leu Asp Asp Glu His Ile Leu Ser Ala Leu Leu Gln
1               5                   10                  15

Ser Asp Asp Glu Leu Val Gly Glu Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn His Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
```

-continued

```
                180                 185                 190
His Met Ser Thr Asp Asp Leu Phe Asp Arg Ser Leu Ser Met Val Tyr
            195                 200                 205
Val Ser Val Met Ser Arg Asp Arg Phe Asp Phe Leu Ile Arg Cys Leu
210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
                260                 265                 270
Gly Phe Arg Gly Arg Cys Pro Phe Arg Met Tyr Ile Pro Asn Lys Pro
                275                 280                 285
Ser Lys Tyr Gly Ile Lys Ile Leu Met Met Cys Asp Ser Gly Thr Lys
                290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
                340                 345                 350
Pro Leu Ala Lys Asn Leu Leu Gln Glu Pro Tyr Lys Leu Thr Ile Val
                355                 360                 365
Gly Thr Val Arg Ser Asn Lys Arg Glu Ile Pro Glu Val Leu Lys Asn
                370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
                420                 425                 430
Pro Gln Met Val Met Tyr Tyr Asn Gln Thr Lys Gly Gly Val Asp Thr
                435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Lys Gly Glu Lys Val
                485                 490                 495
Gln Ser Arg Lys Lys Phe Met Arg Asn Leu Tyr Met Ser Leu Thr Ser
                500                 505                 510
Ser Phe Met Arg Lys Arg Leu Glu Ala Pro Thr Leu Lys Arg Tyr Leu
                515                 520                 525
Arg Asp Asn Ile Ser Asn Ile Leu Pro Asn Glu Val Pro Gly Thr Ser
                530                 535                 540
Asp Asp Ser Thr Glu Glu Pro Val Thr Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
                580                 585                 590
Cys Phe
```

```
<210> SEQ ID NO 6
<211> LENGTH: 2316
<212> TYPE: DNA
<213> ORGANISM: Artificial Sequence
<220> FEATURE:
<223> OTHER INFORMATION: synthetic

<400> SEQUENCE: 6
atgccgaaga gaaacggaa agtcgacccg aagaagaaac ggaaagtcga ctccaattta      60
ctgaccgtac acctgaagct actgtcttct atcgaacaag catgcgatat ttgccgactt    120
aaaaagctca agtgctccaa agaaaaaccg aagtgcgcca agtgtctgaa gaacaactgg    180
gagtgtcgct actctcccaa aaccaaaagg tctccgctga ctagggcaca tctgacagaa    240
gtggaatcaa ggctagaaag actggaacag ctatttctac tgattttcc tcgagaagac    300 cttgacatga ttttgaaaat ggattcttta caggatataa aagcattgtt aacaggatta    360
tttgtacaag ataatgtgaa taaagatgcc gtcacagata gattggcttc agtggagact    420
gatatgcctc taacattgag acagcataga ataagtgcga catcatcatc ggaagagagt    480
agtaacaaag gtcaaagaca gttgactgta tcgatcgggg gctccggggg atccggcagc    540
agcctggacg acgagcacat cctgagcgcc ctgctccaga gcgacgacga gctggtgggc    600
gaggacagcg acagcgagat cagcgaccac gtgagcgagg acgacgtgca gagcgacacc    660
gaggaagcct tcatcgacga ggtgcacgag gtgcagccca ccagcagcgg cagcgagatc    720
ctggacgagc agaacgtgat cgagcagccc ggcagcagcc tggccagcaa caagatcctg    780
accctgcccc agcgcaccat ccggggcaag aacaagcact gctggagcac cagcaagagc    840
acccgccgca gccgcgtgag cgccctgaac acgtgcgca gccagcgcgg ccccacccgc    900
atgtgccgca catctacga ccccctgctg tgcttcaagc tgttcttcac cgacgagatc    960
atcagcgaga tcgtgaagtg gaccaacgcc gagatcagcc tgaagcgccg cgagagcatg   1020 accgcgcca ccttccgcga caccaacgag gacgaaatct acgccttctt cggcatcctg   1080
gtgatgaccg ccgtgcgcaa ggacaaccac atgagcaccg acgcctgtt cgaccgcagc   1140 ctgagcatgg tgtacgtgag cgtgatgagc gcgaccgct tcgacttcct gatccggtgc   1200
ctgcgcatgg acgacaagag catccgcccc accctgcgcg agaacgacgt gttcacccc   1260 gtgcgcaaga tctgggacct gttcatccac cagtgcatcc agaactacac ccccggcgcc   1320
catctgacca tcgacgagca gctgctgggc ttccgcgggc gctgcccctt ccgcatgtac   1380
atccccaaca agcccagcaa gtacggcatc aagatcctga tgatgtgcga cagcggcacc   1440
aagtacatga tcaacggcat gccctacctg ggccgcggca cccagaccaa cggcgtgccc   1500
ctgggcgagt actacgtgaa ggagctgagc aagcccgtgc acggcagctg ccgcaacatc   1560
acctgcgaca actggttcac cagcatcccc ctggccaaga acctgctcca ggagccctac   1620
aagctgacca tcgtgggcac cgtgcgcagc aacaagcgcg agatccccga ggtgctgaag   1680
aacagccgca gccgccccgt gggcaccagc atgttctgct cgacgggccc cctgaccctg   1740
gtgagctaca gcccaagcc cgccaagatg gtgtacctgc tgagcagctg cgacgaggac   1800
gccagcatca acgagagcac cggcaagccc cagatggtga tgtactacaa ccagaccaag   1860
ggcggcgtgg acaccctgga ccagatgtgc agcgtgatga cctgctcccg caagaccaac   1920
cgctggccga tggccctgct gtacggcatg attaacatcg cctgcatcaa cagcttcatc   1980
atctacagcc acaacgtgag cagcaagggc gagaaggtgc agagccgcaa gaagttcatg   2040
cgcaacctgt acatgagcct gaccagcagc ttcatgcgca gcgcctgga ggcccccacc   2100 ctgaagcgct acctgcgcga caacatcagc aacatcctgc caacgaggt gcccggcacc   2160
```

| | | | |
|---|---|---|---|
| agcgacgaca | gcaccgagga | gcccgtgacc | aagaagcgca cctactgcac ctactgcccc | 2220 |
| agcaagatcc | gccgcaaggc | caacgccagc | tgcaagaagt gcaagaaggt gatctgccgc | 2280 |
| gagcacaaca | tcgacatgtg | ccagagctgc | ttctaa | 2316 |

<210> SEQ ID NO 7
<211> LENGTH: 2964
<212> TYPE: DNA
<213> ORGANISM: Artificial Sequence
<220> FEATURE:
<223> OTHER INFORMATION: synthetic

<400> SEQUENCE: 7

| | | | | |
|---|---|---|---|---|
| ggcctctagt | gcggtaaata | gcaataaatt | ggccttttt | atcggcaagc tcttttaggt | 60 |
| ttttcgcatg | tattgcgata | tgcataaacc | agccattgag | taagttttta agcacatcat | 120 |
| catcataagc | tttaagttgg | ttctcttgga | tcaatttgct | gacaatggcg tttaccttac | 180 |
| cagtaatgta | ttcaaggcta | attttttcaa | gttcattcca | accaatgata ggcatcactt | 240 |
| cttggatagg | gataaggttt | ttattattat | caataatata | atcaagataa tgttcaaata | 300 |
| tactttctaa | ggcagaccaa | ccatttgtta | aatcagtttt | tgttgtgatg taggcatcaa | 360 |
| tcataattaa | ttgctgctta | taacaggcac | tgagtaattg | ttttttatt ttaaagtgat | 420 |
| gataaaaggc | acctttggtc | accaacgctt | ttcccgagat | cctctacgcc ggacgcatcg | 480 |
| tggccggcat | caccggcgcc | acaggtgcgg | ttgctggcgc | ctatatcgcc gacatcaccg | 540 |
| atggggaaga | tcgggctcgc | cacttcgggc | tcatgagcgc | ttgtttcggc gtgggtatgg | 600 |
| tggcaggccc | cgtggccggg | ggactgttgg | gcgccatctc | cttgctgcct cgcgcgtttc | 660 |
| ggtgatgacg | tgaaaacct | ctgacacatg | cagctcccgg | agacggtcac agcttgtctg | 720 |
| taagcggatg | ccgggagcag | acaagcccgt | cagggcgcgt | cagcgggtgt tggcgggtgt | 780 |
| cggggcgcag | ccatgaccca | gtcacgtagc | gatagcggag | tgtatactgg cttaactatg | 840 |
| cggcatcaga | gcagattgta | ctgagagtgc | accataaatc | aatctaaagt atatatgagt | 900 |
| aaacttggtc | tgacagttac | caatgcttaa | tcagtgaggc | acctatctca gcgatctgtc | 960 |
| tatttcgttc | atccatagtt | gcctgactcc | ccgtcgtgta | gataactacg atacgggagg | 1020 |
| gcttaccatc | tggccccagt | gctgcaatga | taccgcgaga | cccacgctca ccggctccag | 1080 |
| atttatcagc | aataaaccag | ccagccggaa | gggccgagcg | cagaagtggt cctgcaactt | 1140 |
| tatccgcctc | catccagtct | attaattgtt | gccgggaagc | tagagtaagt agttcgccag | 1200 |
| ttaatagttt | gcgcaacgtt | gttgccattg | ctgcaggcat | cgtggtgtca cgctcgtcgt | 1260 |
| ttggtatggc | ttcattcagc | tccggttccc | aacgatcaag | gcgagttaca tgatcccca | 1320 |
| tgttgtgcaa | aaaagcggtt | agctccttcg | gtcctccgat | cgttgtcaga agtaagttgg | 1380 |
| ccgcagtgtt | atcactcatg | gttatggcag | cactgcataa | ttctcttact gtcatgccat | 1440 |
| ccgtaagatg | cttttctgtg | actggtgagt | actcaaccaa | gtcattctga aatagtgta | 1500 |
| tgcggcgacc | gagttgctct | tgcccggcgt | caatacggga | taataccgcg ccacatagca | 1560 |
| gaactttaaa | agtgctcatc | attggaaaac | gttcttcggg | gcgaaaactc tcaaggatct | 1620 |
| taccgctgtt | gagatccagt | tcgatgtaac | ccactcgtgc | acccaactga tcttcagcat | 1680 |
| cttttacttt | caccagcgtt | tctgggtgag | caaaaacagg | aaggcaaaat gccgcaaaaa | 1740 |
| agggaataag | ggcgacacgg | aaatgttgaa | tactcatact | cttcctttt caatattatt | 1800 |
| gaagcattta | tcagggttat | tgtctcatga | gcggatacat | atttgaatgt atttagaaaa | 1860 |
| ataaacaaat | aggggttccg | cgcacatttc | cccgaaaagt | gccacctgac gtctaagaaa | 1920 |

-continued

```
ccattattat catgacatta acctataaaa ataggcgtat cacgaggccc tttcgtcttc    1980
aagaattccc atgtcagccg ttaagtgttc ctgtgtcact caaaattgct ttgagaggct    2040
ctaagggctt ctcagtgcgt tacatccctg gcttgttgtc cacaaccgtt aaaccttaaa    2100
agctttaaaa gccttatata ttctttttt tcttataaaa cttaaaacct tagaggctat    2160
ttaagttgct gatttatatt aattttattg ttcaaacatg agagcttagt acgtgaaaca    2220
tgagagctta gtacgttagc catgagagct tagtacgtta gccatgaggg tttagttcgt    2280
taaacatgag agcttagtac gttaaacatg agagcttagt acgtgaaaca tgagagctta    2340
gtacgtacta tcaacaggtt gaactgctga acatgagag cttagtacgt tagccatgag    2400
agcttagtac gttagccatg agggtttagt tcgttaaaca tgagagctta gtacgttaaa    2460
catgagagct tagtacgtga acatgagag cttagtacgt actatcaaca ggttgaactg    2520
ctgatcttca gatcctctac gccggacgca tcgtggccgg atcgcggccc ggcgcggtcg    2580
agcaagctta ggcctccaag gcggagtact gtcctccggg ctggcggagt actgtcctcc    2640
ggcaaggtcg gagtactgtc ctccgacact agaggtcgga gtactgtcct ccgacgcaag    2700
gcggagtact gtcctccggg ctgcggagta ctgtcctccg gcaaggtcgg agtactgtcc    2760
tccgacacta gaggtcggag tactgtcctc cgacgcaagg tcggagtact gtcctccgac    2820
actagaggtc ggagtactgt cctccgacgc aaggtcggag tactgtcctc cgacactaga    2880
ggtcggagta ctgtcctccg acgcaaggcg gagtactgtc ctccgggctg cggagtact    2940 gtcctccggc aagggtcgct cgac                                          2964
```

<210> SEQ ID NO 8
<211> LENGTH: 97
<212> TYPE: DNA
<213> ORGANISM: Artificial Sequence
<220> FEATURE:
<223> OTHER INFORMATION: synthetic

<400> SEQUENCE: 8

```
tgctgttgac agtgagcgaa agaacggcat caaggtgaac tagtgaagcc acagatgtag    60
ttcaccttga tgccgttctt ctgcctactg cctcgga                              97
```

<210> SEQ ID NO 9
<211> LENGTH: 97
<212> TYPE: DNA
<213> ORGANISM: Artificial Sequence
<220> FEATURE:
<223> OTHER INFORMATION: synthetic

<400> SEQUENCE: 9

```
tgctgttgac agtgagcgcg gtccgagtgt ggttctgtaa tagtgaagcc acagatgtat    60
tacagaacca cactcggacc atgcctactg cctcgga                              97
```

<210> SEQ ID NO 10
<211> LENGTH: 97
<212> TYPE: DNA
<213> ORGANISM: Artificial Sequence
<220> FEATURE:
<223> OTHER INFORMATION: synthetic

<400> SEQUENCE: 10

```
tgctgttgac agtgagcgat gggaggactt gctgctgttc tagtgaagcc acagatgtag    60
aacagcagca agtcctccca gtgcctactg cctcgga                              97
```

```
<210> SEQ ID NO 11
<211> LENGTH: 97
<212> TYPE: DNA
<213> ORGANISM: Artificial Sequence
<220> FEATURE:
<223> OTHER INFORMATION: synthetic

<400> SEQUENCE: 11
tgctgttgac agtgagcgaa caactcacct gcatgtttat tagtgaagcc acagatgtaa      60
taaacatgca ggtgagttgt ctgcctactg cctcgga                              97

<210> SEQ ID NO 12
<211> LENGTH: 97
<212> TYPE: DNA
<213> ORGANISM: Artificial Sequence
<220> FEATURE:
<223> OTHER INFORMATION: synthetic

<400> SEQUENCE: 12
tgctgttgac agtgagcgat tcagaaccg cagagcaaag tagtgaagcc acagatgtac       60
tttgctctgc ggttctgaaa ctgcctactg cctcgga                              97

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
caagctcctg aagcagaaga ggat                                            24

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14
ctcactcggt tctcgatact ggtt                                            24

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
ccggtcaaga aacagaagac caga                                            24

<210> SEQ ID NO 16
<211> LENGTH: 24
<212> TYPE: DNA
<213> ORGANISM: Artificial Sequence
<220> FEATURE:
<223> OTHER INFORMATION: synthetic

<400> SEQUENCE: 16
ccattgctat tcttcggcca gttg                                            24

<210> SEQ ID NO 17
<211> LENGTH: 24
<212> TYPE: DNA
<213> ORGANISM: Artificial Sequence
```

```
<220> FEATURE:
<223> OTHER INFORMATION: synthetic

<400> SEQUENCE: 17
tcaggagttg tcaaggcaga gaag                                          24

<210> SEQ ID NO 18
<211> LENGTH: 24
<212> TYPE: DNA
<213> ORGANISM: Artificial Sequence
<220> FEATURE:
<223> OTHER INFORMATION: synthetic

<400> SEQUENCE: 18
gccgccgccg atgattgtta ttat                                          24

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
tcaccatggc aaataacctg                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
cagcatgcag gagtatgagg                                               20

<210> SEQ ID NO 21
<211> LENGTH: 27
<212> TYPE: DNA
<213> ORGANISM: Artificial Sequence
<220> FEATURE:
<223> OTHER INFORMATION: synthetic

<400> SEQUENCE: 21
gagattcatc tcaggattga gattcta                                       27

<210> SEQ ID NO 22
<211> LENGTH: 25
<212> TYPE: DNA
<213> ORGANISM: Artificial Sequence
<220> FEATURE:
<223> OTHER INFORMATION: synthetic

<400> SEQUENCE: 22
ggcctactgt aatcttttct ccact                                         25

<210> SEQ ID NO 23
<211> LENGTH: 24
<212> TYPE: DNA
<213> ORGANISM: Artificial Sequence
<220> FEATURE:
<223> OTHER INFORMATION: synthetic

<400> SEQUENCE: 23
tgaacacaga cgctatgcgc tcag                                          24
```

```
<210> SEQ ID NO 24
<211> LENGTH: 25
<212> TYPE: DNA
<213> ORGANISM: Artificial Sequence
<220> FEATURE:
<223> OTHER INFORMATION: synthetic

<400> SEQUENCE: 24
cacctttatg tgagtggaca cagag                                          25

<210> SEQ ID NO 25
<211> LENGTH: 23
<212> TYPE: DNA
<213> ORGANISM: Artificial Sequence
<220> FEATURE:
<223> OTHER INFORMATION: synthetic

<400> SEQUENCE: 25
tgtgagcggg atgactgttc act                                            23

<210> SEQ ID NO 26
<211> LENGTH: 22
<212> TYPE: DNA
<213> ORGANISM: Artificial Sequence
<220> FEATURE:
<223> OTHER INFORMATION: synthetic

<400> SEQUENCE: 26
tgtcatggga ttgcagcatg ga                                             22

<210> SEQ ID NO 27
<211> LENGTH: 19
<212> TYPE: DNA
<213> ORGANISM: Artificial Sequence
<220> FEATURE:
<223> OTHER INFORMATION: synthetic

<400> SEQUENCE: 27
ggtaccccga catccactt                                                 19

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
gcctgttctg gaaccatacc t                                              21

<210> SEQ ID NO 29
<211> LENGTH: 18
<212> TYPE: DNA
<213> ORGANISM: Artificial Sequence
<220> FEATURE:
<223> OTHER INFORMATION: synthetic

<400> SEQUENCE: 29
ggcgcagcag aatccaga                                                  18

<210> SEQ ID NO 30
<211> LENGTH: 18
<212> TYPE: DNA
<213> ORGANISM: Artificial Sequence
<220> FEATURE:
<223> OTHER INFORMATION: synthetic

<400> SEQUENCE: 30
```
ccacgacttg cccagcat                             18

<210> SEQ ID NO 31
<211> LENGTH: 25
<212> TYPE: DNA
<213> ORGANISM: Artificial Sequence
<220> FEATURE:
<223> OTHER INFORMATION: synthetic

<400> SEQUENCE: 31
atcaccgtca acaccaccat ctgtg                     25

<210> SEQ ID NO 32
<211> LENGTH: 22
<212> TYPE: DNA
<213> ORGANISM: Artificial Sequence
<220> FEATURE:
<223> OTHER INFORMATION: synthetic

<400> SEQUENCE: 32
agagtgcaca ttgacagctg ag                        22

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
agtccctgcc acactcag                             18

<210> SEQ ID NO 34
<211> LENGTH: 26
<212> TYPE: DNA
<213> ORGANISM: Artificial Sequence
<220> FEATURE:
<223> OTHER INFORMATION: synthetic

<400> SEQUENCE: 34
ccttgtcatg taccatcaat aaagta                    26

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
cttaaggaat tcgataaaag                           20

<210> SEQ ID NO 36
<211> LENGTH: 19
<212> TYPE: DNA
<213> ORGANISM: Artificial Sequence
<220> FEATURE:
<223> OTHER INFORMATION: synthetic

<400> SEQUENCE: 36
gatacattga tgagtttgg                            19

<210> SEQ ID NO 37
<211> LENGTH: 20
<212> TYPE: DNA
<213> ORGANISM: Artificial Sequence

```
<220> FEATURE:
<223> OTHER INFORMATION: synthetic

<400> SEQUENCE: 37
cgtgcttaca ggcattgagc                                                    20

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
ctggaacctc gacttcttgg                                                    20

<210> SEQ ID NO 39
<211> LENGTH: 313
<212> TYPE: DNA
<213> ORGANISM: Trichoplusia ni
<220> FEATURE:
<221> NAME/KEY: mutation
<222> LOCATION: (54)..(54)
<223> OTHER INFORMATION: thymine 54 to cytosine subsitution in enhanced
      5'-terminal repeat
<220> FEATURE:
<221> NAME/KEY: mutation
<222> LOCATION: (137)..(137)
<223> OTHER INFORMATION: cytosine 137 to thymine subsitution in enhanced
      5'-terminal repeat

<400> SEQUENCE: 39
gatatctata caagaaaat atatataa taagttatca cgtaagtaga acacgaaata           60
acaatataat tatcgtatga gttaaatctt aaaagtcacg taaagataa tcatgcgtca        120 ttttgactca cgcggttgtt atagttcaaa atcagtgaca cttaccgcat tgacaagcac       180
gcctcacggg agctccaagc ggcgactgag atgtcctaaa tgcacagcga cggattcgcg       240
ctatttagaa agagagagca atatttcaag aatgcatgcg tcaatttac gcagactatc       300 tttctagggt taa                                                          313
```

<210> SEQ ID NO 40
<211> LENGTH: 771
<212> TYPE: PRT
<213> ORGANISM: Trichoplusia ni

<400> SEQUENCE: 40

| Met | Pro | Lys | Lys | Lys | Arg | Lys | Val | Asp | Pro | Lys | Lys | Arg | Lys | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Asp Ser Asn Leu Leu Thr Val His Leu Lys Leu Leu Ser Ser Ile Glu
            20                  25                  30

Gln Ala Cys Asp Ile Cys Arg Leu Lys Lys Leu Lys Cys Ser Lys Glu
        35                  40                  45

Lys Pro Lys Cys Ala Lys Cys Leu Lys Asn Asn Trp Glu Cys Arg Tyr
    50                  55                  60

Ser Pro Lys Thr Lys Arg Ser Pro Leu Thr Arg Ala His Leu Thr Glu
65                  70                  75                  80

Val Glu Ser Arg Leu Glu Arg Leu Glu Gln Leu Phe Leu Leu Ile Phe
                85                  90                  95

Pro Arg Glu Asp Leu Asp Met Ile Leu Lys Met Asp Ser Leu Gln Asp
            100                 105                 110

Ile Lys Ala Leu Leu Thr Gly Leu Phe Val Gln Asp Asn Val Asn Lys
        115                 120                 125

-continued

```
Asp Ala Val Thr Asp Arg Leu Ala Ser Val Glu Thr Asp Met Pro Leu
        130                 135                 140
Thr Leu Arg Gln His Arg Ile Ser Ala Thr Ser Ser Glu Glu Ser
145                 150                 155                 160
Ser Asn Lys Gly Gln Arg Gln Leu Thr Val Ser Ile Gly Gly Ser Gly
                165                 170                 175
Gly Ser Gly Ser Ser Leu Asp Asp Glu His Ile Leu Ser Ala Leu Leu
            180                 185                 190
Gln Ser Asp Asp Glu Leu Val Gly Glu Asp Ser Asp Ser Glu Ile Ser
        195                 200                 205
Asp His Val Ser Glu Asp Asp Val Gln Ser Asp Thr Glu Glu Ala Phe
        210                 215                 220
Ile Asp Glu Val His Glu Val Gln Pro Thr Ser Gly Ser Glu Ile
225                 230                 235                 240
Leu Asp Glu Gln Asn Val Ile Glu Gln Pro Gly Ser Ser Leu Ala Ser
                245                 250                 255
Asn Lys Ile Leu Thr Leu Pro Gln Arg Thr Ile Arg Gly Lys Asn Lys
                260                 265                 270
His Cys Trp Ser Thr Ser Lys Ser Thr Arg Arg Ser Arg Val Ser Ala
            275                 280                 285
Leu Asn His Val Arg Ser Gln Arg Gly Pro Thr Arg Met Cys Arg Asn
        290                 295                 300
Ile Tyr Asp Pro Leu Leu Cys Phe Lys Leu Phe Phe Thr Asp Glu Ile
305                 310                 315                 320
Ile Ser Glu Ile Val Lys Trp Thr Asn Ala Glu Ile Ser Leu Lys Arg
                325                 330                 335
Arg Glu Ser Met Thr Gly Ala Thr Phe Arg Asp Thr Asn Glu Asp Glu
            340                 345                 350
Ile Tyr Ala Phe Phe Gly Ile Leu Val Met Thr Ala Val Arg Lys Asp
        355                 360                 365
Asn His Met Ser Thr Asp Asp Leu Phe Asp Arg Ser Leu Ser Met Val
        370                 375                 380
Tyr Val Ser Val Met Ser Arg Asp Arg Phe Asp Phe Leu Ile Arg Cys
385                 390                 395                 400
Leu Arg Met Asp Asp Lys Ser Ile Arg Pro Thr Leu Arg Glu Asn Asp
                405                 410                 415
Val Phe Thr Pro Val Arg Lys Ile Trp Asp Leu Phe Ile His Gln Cys
                420                 425                 430
Ile Gln Asn Tyr Thr Pro Gly Ala His Leu Thr Ile Asp Glu Gln Leu
        435                 440                 445
Leu Gly Phe Arg Gly Arg Cys Pro Phe Arg Met Tyr Ile Pro Asn Lys
        450                 455                 460
Pro Ser Lys Tyr Gly Ile Lys Ile Leu Met Met Cys Asp Ser Gly Thr
465                 470                 475                 480
Lys Tyr Met Ile Asn Gly Met Pro Tyr Leu Gly Arg Gly Thr Gln Thr
                485                 490                 495
Asn Gly Val Pro Leu Gly Glu Tyr Tyr Val Lys Glu Leu Ser Lys Pro
            500                 505                 510
Val His Gly Ser Cys Arg Asn Ile Thr Cys Asp Asn Trp Phe Thr Ser
        515                 520                 525
Ile Pro Leu Ala Lys Asn Leu Leu Gln Glu Pro Tyr Lys Leu Thr Ile
        530                 535                 540
Val Gly Thr Val Arg Ser Asn Lys Arg Glu Ile Pro Glu Val Leu Lys
```

```
                545                 550                 555                 560
Asn Ser Arg Ser Arg Pro Val Gly Thr Ser Met Phe Cys Phe Asp Gly
                565                 570                 575

Pro Leu Thr Leu Val Ser Tyr Lys Pro Lys Pro Ala Lys Met Val Tyr
            580                 585                 590

Leu Leu Ser Ser Cys Asp Glu Asp Ala Ser Ile Asn Glu Ser Thr Gly
            595                 600                 605

Lys Pro Gln Met Val Met Tyr Tyr Asn Gln Thr Lys Gly Gly Val Asp
        610                 615                 620

Thr Leu Asp Gln Met Cys Ser Val Met Thr Cys Ser Arg Lys Thr Asn
625                 630                 635                 640

Arg Trp Pro Met Ala Leu Leu Tyr Gly Met Ile Asn Ile Ala Cys Ile
                645                 650                 655

Asn Ser Phe Ile Ile Tyr Ser His Asn Val Ser Ser Lys Gly Glu Lys
                660                 665                 670

Val Gln Ser Arg Lys Lys Phe Met Arg Asn Leu Tyr Met Ser Leu Thr
            675                 680                 685

Ser Ser Phe Met Arg Lys Arg Leu Glu Ala Pro Thr Leu Lys Arg Tyr
        690                 695                 700

Leu Arg Asp Asn Ile Ser Asn Ile Leu Pro Asn Glu Val Pro Gly Thr
705                 710                 715                 720

Ser Asp Asp Ser Thr Glu Glu Pro Val Thr Lys Arg Thr Tyr Cys
                725                 730                 735

Thr Tyr Cys Pro Ser Lys Ile Arg Arg Lys Ala Asn Ala Ser Cys Lys
            740                 745                 750

Lys Cys Lys Lys Val Ile Cys Arg Glu His Asn Ile Asp Met Cys Gln
            755                 760                 765

Ser Cys Phe
        770

<210> SEQ ID NO 41
<211> LENGTH: 17
<212> TYPE: PRT
<213> ORGANISM: Artificial Sequence
<220> FEATURE:
<223> OTHER INFORMATION: synthetic

<400> SEQUENCE: 41

Met Pro Lys Lys Lys Arg Lys Val Asp Pro Lys Lys Lys Arg Lys Val
1               5                   10                  15

Asp

<210> SEQ ID NO 42
<211> LENGTH: 9
<212> TYPE: PRT
<213> ORGANISM: Artificial Sequence
<220> FEATURE:
<223> OTHER INFORMATION: synthetic

<400> SEQUENCE: 42

Gly Gly Ser Gly Gly Ser Gly Ser Ser
1               5

<210> SEQ ID NO 43
<211> LENGTH: 3742
<212> TYPE: DNA
<213> ORGANISM: Artificial sequence
<220> FEATURE:
<223> OTHER INFORMATION: synthetic
```

<400> SEQUENCE: 43

```
gtggcacttt tcggggaaat gtgcgcggaa ccctatttg tttatttttc taaatacatt        60
caaatatgta tccgctcatg agacaataac cctgataaat gcttcaataa tattgaaaaa       120
ggaagagtat gagtattcaa catttccgtg tcgcccttat tccctttttt gcggcatttt       180
gccttcctgt ttttgctcac ccagaaacgc tggtgaaagt aaaagatgct gaagatcagt       240
tgggtgcacg agtgggttac atcgaactgg atctcaacag cggtaagatc cttgagagtt       300
ttcgccccga gaacgttttt ccaatgatga gcacttttaa agttctgcta tgtggcgcgg       360
tattatcccg tattgacgcc gggcaagagc aactcggtcg ccgcatacac tattctcaga       420
atgacttggt tgagtactca ccagtcacag aaaagcatct tacggatggc atgacagtaa       480
gagaattatg cagtgctgcc ataaccatga gtgataacac tgcggccaac ttacttctga       540
caacgatcgg aggaccgaag gagctaaccg cttttttgca acatggggg gatcatgtaa       600
ctcgccttga tcgttgggaa ccggagctga atgaagccat accaaacgac gagcgtgaca       660
ccacgatgcc tgtagcaatg gcaacaacgt tgcgcaaact attaactggc gaactactta       720
ctctagcttc ccggcaacaa ttaatagact ggatggaggc ggataaagtt gcaggaccac       780
ttctgcgctc ggcccttccg gctggctggt ttattgctga taaatctgga gccggtgagc       840
gtgggtctcg cggtatcatt gcagcactgg ggccagatgg taagccctcc cgtatcgtag       900
ttatctacac gacggggagt caggcaacta tggatgaacg aaatagacag atcgctgaga       960
taggtgcctc actgattaag cattggtaac tgtcagacca agtttactca tatatacttt      1020
agattgattt aaaacttcat ttttaattta aaaggatcta ggtgaagatc cttttgata       1080
atctcatgac caaaatccct taacgtgagt tttcgttcca ctgagcgtca gaccccgtag      1140
aaaagatcaa aggatcttct tgagatcctt ttttctgcg cgtaatctgc tgcttgcaaa       1200
caaaaaaacc accgctacca gcggtggttt gtttgccgga tcaagagcta ccaactcttt      1260
ttccgaaggt aactggcttc agcagagcgc agataccaaa tactgtcctt ctagtgtagc      1320
cgtagttagg ccaccacttc aagaactctg tagcaccgcc tacatacctc gctctgctaa      1380
tcctgttacc agtggctgct gccagtggcg ataagtcgtg tcttaccggg ttggactcaa      1440
gacgatagtt accggataag gcgcagcggt cgggctgaac ggggggttcg tgcacacagc      1500
ccagcttgga gcgaacgacc tacaccgaac tgagatacct acagcgtgag ctatgagaaa      1560
gcgccacgct tcccgaaggg agaaaggcgg acaggtatcc ggtaagcggc agggtcggaa      1620
caggagagcg cacgagggag cttccagggg gaaacgcctg gtatctttat agtcctgtcg      1680
ggtttcgcca cctctgactt gagcgtcgat ttttgtgatg ctcgtcaggg gggcggagcc      1740
tatgaaaaaa cgccagcaac gcggcctttt tacggttcct ggccttttgc tggccttttg      1800
ctcacatgtt ctttcctgcg ttatcccctg attctgtgga taaccgtatt accgcctttg      1860
agtgagctga taccgctcgc cgcagccgaa cgaccgagcg cagcgagtca gtgagcgagg      1920
aagcggaaga gcgcccaata cgcaaaccgc ctctccccgc gcgttggccg attcattaat      1980
gcagctggca cgacaggttt cccgactgga aagcgggcag tgagcgcaac gcaattaatg      2040
tgagttagct cactcattag gcaccccagg ctttacactt tatgcttccg gctcgtatgt      2100
tgtgtggaat tgtgagcgga taacaatttc acacaggaaa cagctatgac catgattacg      2160
ccaagcgcgc aattaaccct cactaaaggg aacaaaagct ggagctccac cgcggggcgc      2220
gccgcagcta gattaaccct agaaagatag tctgcgtaaa attgacgcat gcattcttga      2280
aatattgctc tctctttcta aatagcgcga atccgtcgct gtgcatttag gacatctcag      2340
```

```
tcgccgcttg gagctcccgt gaggcgtgct tgtcaatgcg gtaagtgtca ctgattttga    2400
actataacaa ccgcgtgagt caaaatgacg catgattatc ttttacgtga cttttaagat    2460
ttaactcata cgataattat attgttattt cgtgttctac ttacgtgata acttattata    2520
tatatatttt cttgttatag atatccttct cgagggatcc aagcttatcg atgcggccgc    2580
gactctagat cataatcagc cataccacat tgtagaggt tttacttgct ttaaaaaacc    2640
tcccacacct cccctgaac ctgaaacata aatgaatgc aattgttgtt gttaacttgt    2700
ttattgcagc ttataatggt tacaaataaa gcaatagcat cacaaatttc acaaataaag    2760 cattttttc actgcattct agttgtggtt tgtccaaact catcaatgta tcttaaggaa    2820
ttcgataaaa gttttgttac tttatagaag aaattttgag tttttgtttt tttttaataa    2880
ataaataaac ataaataaat tgtttgttga atttattatt agtatgtaag tgtaaatata    2940
ataaaactta atatctattc aaattaataa ataaacctcg atatacagac cgataaaaca    3000
catgcgtcaa ttttacgcat gattatcttt aacgtacgtc acaatatgat tatctttcta    3060
gggttaatct agctgcggcg cgccggtacc caattcgccc tatagtgagt cgtattacgc    3120
gcgctcactg gccgtcgttt tacaacgtcg tgactgggaa aaccctggcg ttacccaact    3180
taatcgcctt gcagcacatc ccctttcgc cagctggcgt aatagcgaag aggcccgcac    3240
cgatcgccct tcccaacagt tgcgcagcct gaatggcgaa tgggacgcgc cctgtagcgg    3300
cgcattaagc gcggcgggtg tggtggttac gcgcagcgtg accgctacac ttgccagcgc    3360
cctagcgccc gctcctttcg ctttcttccc ttcctttctc gccacgttcg ccggcttttcc    3420 ccgtcaagct ctaaatcggg ggctcccttt agggttccga tttagtgctt tacggcacct    3480
cgaccccaaa aaacttgatt agggtgatgg ttcacgtagt gggccatcgc cctgatagac    3540 ggttttcgc cctttgacgt tggagtccac gttctttaat agtggactct gttccaaac    3600 tggaacaaca ctcaaccta tctcggtcta ttctttgat ttataaggga ttttgccgat    3660
ttcggcctat tggttaaaaa atgagctgat ttaacaaaaa tttaacgcga attttaacaa    3720
aatattaacg cttacaattt ag                                            3742

<210> SEQ ID NO 44
<211> LENGTH: 853
<212> TYPE: DNA
<213> ORGANISM: Artificial sequence
<220> FEATURE:
<223> OTHER INFORMATION: synthetic

<400> SEQUENCE: 44
gcagctagat taaccctaga aagatagtct gcgtaaaatt gacgcatgca ttcttgaaat      60
attgctctct ctttctaaat agcgcgaatc cgtcgctgtg catttaggac atctcagtcg     120
ccgcttggag ctcccgtgag gcgtgcttgt caatgcggta agtgtcactg attttgaact     180
ataacaaccg cgtgagtcaa aatgacgcat gattatcttt acgtgacttt taagattta     240 actcatacga taattatatt gttatttcgt gttctactta cgtgataact tattatatat     300
atattttctt gttatagata tccttctcga gggatccaag cttatcgatg cggccgcgac     360
tctagatcat aatcagccat accacatttg tagaggtttt acttgcttta aaaaacctcc     420
cacacctccc cctgaacctg aaacataaa tgaatgcaat tgttgttgtt aacttgttta     480
ttgcagctta taatggttac aaataaagca atagcatcac aaatttcaca aataaagcat     540 tttttcact gcattctagt tgtggtttgt ccaaactcat caatgtatct taaggaattc     600
gataaaagtt ttgttacttt atagaagaaa ttttgagttt ttgtttttttt ttaataaata     660
```

| | |
|---|---|
| aataaacata aataaattgt ttgttgaatt tattattagt atgtaagtgt aaatataata | 720 |
| aaacttaata tctattcaaa ttaataaata aacctcgata tacagaccga taaaacacat | 780 |
| gcgtcaattt tacgcatgat tatctttaac gtacgtcaca atatgattat ctttctaggg | 840 |
| ttaatctagc tgc | 853 |

```
<210> SEQ ID NO 45
<211> LENGTH: 313
<212> TYPE: DNA
<213> ORGANISM: Trichoplusia ni

<400> SEQUENCE: 45
```

| | |
|---|---|
| gatatctata acaagaaaat atatatataa taagttatca cgtaagtaga tcatgaaata | 60 |
| acaatataat tatcgtatga gttaaatctt aaaagtcacg taaaagataa tcatgcgtca | 120 |
| ttttgactca cgcggtcgtt atagttcaaa atcagtgaca cttaccgcat tgacaagcac | 180 |
| gcctcacggg agctccaagc ggcgactgag atgtcctaaa tgcacagcga cggattcgcg | 240 |
| ctatttagaa agagagagca atatttcaag aatgcatgcg tcaattttac gcagactatc | 300 |
| tttctagggt taa | 313 |

```
<210> SEQ ID NO 46
<211> LENGTH: 313
<212> TYPE: DNA
<213> ORGANISM: Trichoplusia ni

<400> SEQUENCE: 46
```

| | |
|---|---|
| gatatctata acaagaaaat atatatataa taagttatca cgtaagtaga acatgaaata | 60 |
| acaatataat tatcgtatga gttaaatctt aaaagtcacg taaaagataa tcatgcgtca | 120 |
| ttttgactca cgcggtcgtt atagttcaaa ataagtgaca cttaccgcat tgacaagcac | 180 |
| gcctcacggg agctccaagc ggcgactgag atgtcctaaa tgcacagcga cggattcgcg | 240 |
| ctatttagaa agagagagca atatttcaag aatgcatgcg tcaattttac gcagactatc | 300 |
| tttctagggt taa | 313 |

```
<210> SEQ ID NO 47
<211> LENGTH: 313
<212> TYPE: DNA
<213> ORGANISM: Trichoplusia ni

<400> SEQUENCE: 47
```

| | |
|---|---|
| gatatctata acaagaaaat atatatataa taagttatca cgtaagtaga acatgaaata | 60 |
| acaatataat tatcgtatga gttaaatctt aaaagtcacg taaaagataa tcatgcgtca | 120 |
| ttcggactca cgcggtcgtt atagttcaaa atcagtgaca cttaccgcat tgacaagcac | 180 |
| gcctcacggg agctccaagc ggcgactgag atgtcctaaa tgcacagcga cggattcgcg | 240 |
| ctatttagaa agagagagca atatttcaag aatgcatgcg tcaattttac gcagactatc | 300 |
| tttctagggt taa | 313 |

```
<210> SEQ ID NO 48
<211> LENGTH: 313
<212> TYPE: DNA
<213> ORGANISM: Trichoplusia ni

<400> SEQUENCE: 48
```

| | |
|---|---|
| gatatctata acaagaaaat atatatataa taagttatca cgtaagtaga acatgaaata | 60 |
| acaatataat tatcgtatga gttaaatctt aaaagtcacg taaaagataa tcatgcgtca | 120 |

```
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
atatttagaa agagagagca atatttcaag aatgcatgcg tcaattttac gcagactatc    300
tttctagggt taa                                                       313

<210> SEQ ID NO 49
<211> LENGTH: 313
<212> TYPE: DNA
<213> ORGANISM: Trichoplusia ni

<400> SEQUENCE: 49
gatatctata acaagaaaat atatatataa taagttatca cgtaagtaga acatgaaata    60
acaatataat tatcgtatga gttaaatctt aaaagtcacg taaaagataa tcatgcgtca   120
ttttgcctca cgcggtcgtt atagttcaaa atcagtgaca cttaccgcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313

<210> SEQ ID NO 50
<211> LENGTH: 313
<212> TYPE: DNA
<213> ORGANISM: Trichoplusia ni

<400> SEQUENCE: 50
gatatctata acaagaaaat atatatataa taagttatca cgtaagtaga acatgaaata    60
acaatataat tatcgtatga gttaaatctt aaaagtcacg taaaagataa tcatgcgtca   120
ttttgactca cgcggtcgtt aaagttcaaa atcagtgaca cttaccgcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313

<210> SEQ ID NO 51
<211> LENGTH: 313
<212> TYPE: DNA
<213> ORGANISM: Trichoplusia ni

<400> SEQUENCE: 51
gatatctata acaagaaaat atatatataa taagttatca cgtaagtaga acatgaaata    60
acaatataat tatcgtatga gttaaatctt aaaagtcacg taaaagataa acatgcgtca   120
ttttgactca cgcggtcgtt atagttcaaa atcagtgaca cttaccgcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313

<210> SEQ ID NO 52
<211> LENGTH: 313
<212> TYPE: DNA
<213> ORGANISM: Trichoplusia ni

<400> SEQUENCE: 52
gatatctata acaagaaaat atatatataa taagttatca cgtaagtaga acatgaaata    60
acaatataat tatcgtatga gttaaatctt aaaagtcacg taaaagataa tcatgcgtca   120
```

```
ttttgactca cgcggtcgtt atagttcaaa atcagtgaca cttaccgcat tgacaagcac    180
gcctcacggg agctccaagc ggcgactgag atgtcctaaa tgcacagcga cggatttgcg    240
ctatttagaa agagagagca atatttcaag aatgcatgcg tcaattttac gcagactatc    300
tttctagggt taa                                                      313
```

<210> SEQ ID NO 53
<211> LENGTH: 313
<212> TYPE: DNA
<213> ORGANISM: Trichoplusia ni

<400> SEQUENCE: 53

```
gatatctata acaagaaaat atatatataa taagttatca cgtaagtaga acatgaaata    60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc aacgactgag atgtcctaaa tgcacagcga cggattcgcg    240
ctatttagaa agagagagca atatttcaag aatgcatgcg tcaattttac gcagactatc    300
tttctagggt taa                                                      313
```

<210> SEQ ID NO 54
<211> LENGTH: 313
<212> TYPE: DNA
<213> ORGANISM: Trichoplusia ni

<400> SEQUENCE: 54

```
gatatctata acaagaaaat atatatataa taagttatca cgtaagtaga acatgaaata    60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgag atgtcctaaa tgcacagcga cggatacgcg    240
ctatttagaa agagagagca atatttcaag aatgcatgcg tcaattttac gcagactatc    300
tttctagggt taa                                                      313
```

<210> SEQ ID NO 55
<211> LENGTH: 313
<212> TYPE: DNA
<213> ORGANISM: Trichoplusia ni

<400> SEQUENCE: 55

```
gatatctata acaagaaaat atatatataa taagttatca cgtaagtaga acatgaaata    60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgac atgtcctaaa tgcacagcga cggattcgcg    240
ctatttagaa agagagagca atatttcaag aatgcatgcg tcaattttac gcagactatc    300
tttctagggt taa                                                      313
```

<210> SEQ ID NO 56
<211> LENGTH: 313
<212> TYPE: DNA
<213> ORGANISM: Trichoplusia ni

<400> SEQUENCE: 56

```
gatatctata acaagaaaat atatatataa taagttatca cgtaagtaga acatgaaata    60
acaatataat tatcgtatga gttaaatctt aaaagtcacg tatcagataa tcatgcgtca    120
```

```
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaatttttac gcagactatc   300 tttctagggt taa                                                      313

<210> SEQ ID NO 57
<211> LENGTH: 313
<212> TYPE: DNA
<213> ORGANISM: Trichoplusia ni

<400> SEQUENCE: 57
gatatctata acaagaaaat atatatataa taagttatca cgtaagtaga acatgaaata    60
acaatataat tatcgtatga gttaaatctt aaaagtcacg taaaagataa tcatgcgtca    120
ttatgactca cgcggtcgtc atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaatttttac gcagactatc   300 tttctagggt taa                                                      313

<210> SEQ ID NO 58
<211> LENGTH: 313
<212> TYPE: DNA
<213> ORGANISM: Trichoplusia ni

<400> SEQUENCE: 58
gatatctata acaagaaaat atatatataa taagttatca cgtaagtaga acatgaaata    60
acaatataat tatcgtatga gttaaatctt aaaagtcacg taaaagataa tcatgcgtct    120
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaatttttac gcagactatc   300 tttctagggt taa                                                      313

<210> SEQ ID NO 59
<211> LENGTH: 313
<212> TYPE: DNA
<213> ORGANISM: Trichoplusia ni

<400> SEQUENCE: 59
gatatctata acaagaaaat atatatataa taagttatca cgtaagtaga acatgaaata    60
acaatataat tatcgtatga gttaaatctt aaaagtcacg taaaagataa tcatgcgtca    120
ttttgactca cgcggtctttt atagttcaaa atcagtgaca cttaccgcat tgacaagcac   180
gcctcacggg agctccaagc ggcgactgag atgtcctaaa tgcacagcga cggattcgcg    240
ctatttagaa agagagagca atatttcaag aatgcatgcg tcaatttttac gcagactatc   300 tttctagggt taa                                                      313

<210> SEQ ID NO 60
<211> LENGTH: 313
<212> TYPE: DNA
<213> ORGANISM: Trichoplusia ni

<400> SEQUENCE: 60
gatatctata acaagaaaat atatatataa taagttatca cgtaagtaga acatgaaata    60
acaatataat tatcgtatga gttaaatctt aaaagtcacg aaaaagataa tcatgcgtca    120
```

```
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taa                                                       313
```

<210> SEQ ID NO 61
<211> LENGTH: 313
<212> TYPE: DNA
<213> ORGANISM: Trichoplusia ni

<400> SEQUENCE: 61

```
gatatctata acaagaaaat atatatataa taagttatca cgtaagtaga acatgaaata    60
acaatataat tatcgtatga gttaaatctt aaaagtcacg taaaagataa tcatgcgaca   120
ttttgactca cgcggtcgtt atagttcaaa atcagtgaca cttacggcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313
```

<210> SEQ ID NO 62
<211> LENGTH: 313
<212> TYPE: DNA
<213> ORGANISM: Trichoplusia ni

<400> SEQUENCE: 62

```
gatatctata acaagaaaat atatatataa taagttatca cgtaagtaga acatgaaata    60
acaatataat tattgtatga gttaaatctt aaaagtcacg taaaagataa tcatgcgtca   120
ttttgactca cgcggtcgtt atagttcaaa atcagtgaca cttaccgcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313
```

<210> SEQ ID NO 63
<211> LENGTH: 313
<212> TYPE: DNA
<213> ORGANISM: Trichoplusia ni

<400> SEQUENCE: 63

```
gatatctata acaagaaaat atatatataa taagttatca cgtaagtaga acatgaaata    60
acaatataat tatcgtatga gttaaatctt aaaagtcacg taaaagataa tcatgcgtca   120
ttttgactca cgcggtcgtt atagttcaaa atcagtgaca cttaccgcat tgacaagccc   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313
```

<210> SEQ ID NO 64
<211> LENGTH: 53
<212> TYPE: DNA
<213> ORGANISM: Artificial sequence
<220> FEATURE:
<223> OTHER INFORMATION: synthetic

<400> SEQUENCE: 64

```
agactatctt tctagggtta agcacatcat catcataagc tttaagttgg ttc           53
```

<210> SEQ ID NO 65
<211> LENGTH: 53
<212> TYPE: DNA
<213> ORGANISM: Artificial sequence
<220> FEATURE:
<223> OTHER INFORMATION: synthetic

<400> SEQUENCE: 65
agactatctt tctagggtta aatcagtttt tgttgtgatg taggcatcaa tca    53

<210> SEQ ID NO 66
<211> LENGTH: 53
<212> TYPE: DNA
<213> ORGANISM: Artificial sequence
<220> FEATURE:
<223> OTHER INFORMATION: synthetic

<400> SEQUENCE: 66
agactatctt tctagggtta attatgattg atgcctacat cacaacaaaa act    53

<210> SEQ ID NO 67
<211> LENGTH: 53
<212> TYPE: DNA
<213> ORGANISM: Artificial sequence
<220> FEATURE:
<223> OTHER INFORMATION: synthetic

<400> SEQUENCE: 67
agactatctt tctagggtta agccagtata cactccgcta tcgctacgtg act    53

<210> SEQ ID NO 68
<211> LENGTH: 53
<212> TYPE: DNA
<213> ORGANISM: Artificial sequence
<220> FEATURE:
<223> OTHER INFORMATION: synthetic

<400> SEQUENCE: 68
agactatctt tctagggtta aagtgatgat aaaaggcacc tttggtcacc aac    53

<210> SEQ ID NO 69
<211> LENGTH: 53
<212> TYPE: DNA
<213> ORGANISM: Artificial sequence
<220> FEATURE:
<223> OTHER INFORMATION: synthetic

<400> SEQUENCE: 69
agactatctt tctagggtta acctataaaa ataggcgtat cacgaggccc ttt    53

<210> SEQ ID NO 70
<211> LENGTH: 53
<212> TYPE: DNA
<213> ORGANISM: Artificial sequence
<220> FEATURE:
<223> OTHER INFORMATION: synthetic

<400> SEQUENCE: 70
agactatctt tctagggtta aaccttaaaa gctttaaaag ccttatatat tct    53

<210> SEQ ID NO 71
<211> LENGTH: 53
<212> TYPE: DNA
<213> ORGANISM: Artificial sequence
<220> FEATURE:
<223> OTHER INFORMATION: synthetic

```
<400> SEQUENCE: 71
agactatctt tctagggtta acgaactaaa ccctcatggc taacgtacta agc            53

<210> SEQ ID NO 72
<211> LENGTH: 42
<212> TYPE: DNA
<213> ORGANISM: Homo sapiens

<400> SEQUENCE: 72
cagggagttt aacatctgga agagccggga gttctttgtg ct                       42

<210> SEQ ID NO 73
<211> LENGTH: 42
<212> TYPE: DNA
<213> ORGANISM: Artificial sequence
<220> FEATURE:
<223> OTHER INFORMATION: synthetic

<400> SEQUENCE: 73
aaattacatt aacatctgga agagccggga gttctttgtg ct                       42

<210> SEQ ID NO 74
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(28)
<223> OTHER INFORMATION: artificial
<220> FEATURE:
<221> NAME/KEY: misc_feature
<222> LOCATION: (1)..(11)
<223> OTHER INFORMATION: n is a,g,c, or t
<220> FEATURE:
<221> NAME/KEY: misc_feature
<222> LOCATION: (12)..(12)
<223> OTHER INFORMATION: d is a,g, or t
<220> FEATURE:
<221> NAME/KEY: misc_feature
<222> LOCATION: (17)..(17)
<223> OTHER INFORMATION: n is a,g,c, or t
<220> FEATURE:
<221> NAME/KEY: misc_feature
<222> LOCATION: (18)..(18)
<223> OTHER INFORMATION: d is a,g, or t
<220> FEATURE:
<221> NAME/KEY: misc_feature
<222> LOCATION: (19)..(27)
<223> OTHER INFORMATION: n is a,g,c, or t
<220> FEATURE:
<221> NAME/KEY: misc_feature
<222> LOCATION: (28)..(28)
<223> OTHER INFORMATION: h is a, c, or t

<400> SEQUENCE: 74
nnnnnnnnnn ndttaandnn nnnnnnh                                        28

<210> SEQ ID NO 75
<211> LENGTH: 15
<212> TYPE: PRT
<213> ORGANISM: Artificial sequence
<220> FEATURE:
<223> OTHER INFORMATION: synthetic

<400> SEQUENCE: 75

Gly Gly Gly Gly Ser Gly Gly Gly Gly Ser Gly Gly Gly Gly Ser
 1               5                  10                  15
```

ENHANCED PIGGYBAC TRANSPOSON AND METHODS FOR TRANSPOSON MUTAGENESIS

CROSS-REFERENCE TO RELATED APPLICATIONS

This application claims the benefit of U.S. Appl. No. 61/161,872, filed Mar. 20, 2009, which is incorporated herein by reference in its entirety.

INCORPORATION OF SEQUENCE LISTING

A computer readable form of the Sequence Listing is provided herein, containing the file named "49248_88651_SEQLST_ST25_V4.txt" (created on Jul. 12, 2013), which is 49,972 bytes in size (measured in MS-DOS), and is incorporated herein by reference. This Sequence Listing consists of SEQ ID NOs: 1-75.

BACKGROUND OF THE INVENTION

Human pluripotent stem cells (hESCs) hold remarkable potential for regenerative medicine, drug screens and basic research on human diseases. However, a number of technical hurdles still limit our ability to fully unravel their potential for therapeutic applications and basic research. One such hurdle is the difficulty in generating transgenic hESC lines and the use of reporter systems or gain- or loss-of-function approaches.

Currently, gene transfer into hESCs is mostly based on the use of viral vectors. These vectors can mediate transgene expression in 20-80% of human ES cells (Pfeifer, A., et al. (2002) Proc. Natl. Acad. Sci. U.S.A. 99: 2140-2145; Ben-Dor, I., et al. (2006) Mol. Ther. 14: 255-267) but their cargo size is restricted to about 5 Kb and their insert is often limited to one expression cassette. Non-viral systems using the Sleeping Beauty transposon are also restricted to a cargo size of 5-6 Kb (Wilber, A., et al. (2007) Stem Cells 25: 2919-2927). These characteristics limit the use of selectable markers, inducible cassettes, insulators and large regulatory sequences often required to restrict transgene expression to specific cell types. Baculoviruses can deliver larger cargo to hESC (Zeng, J., et al. (2007) Stem Cells 25: 1055-1061) but the long-term effect of adeno-associated rep protein expression could lead to undesirable effects (McCarty, D. M., et al. (2004) Annu. Rev. Genet. 38: 819-845). In principle, plasmids and bacterial artificial chromosomes (BACs) can be used when large promoters are required, but stable integration of these vectors in the hESC genome is relatively inefficient and plasmid-borne transgenes are subject to silencing (Braam, S. R., et al. (2008) Nat. Methods 5: 389-392). In addition, BACs usually carry several intact genes in addition to the engineered locus, therefore their integration in the genome leads to gene multiplications. This may have important consequences when the supernumerary genes have regulatory functions.

Regardless of efficiency, gene transfer technologies currently available in hESCs such as viral vectors, Sleeping Beauty transposons or PhiC31 integrase (Thyagarajan, B., et al. (2008) Stem Cells 26: 119-126) mediate irreversible genome modifications. This constitutes a major barrier to the clinic because the presence of exogenous inserts in certain loci may lead to higher predisposition towards tumorigenesis or uncontrolled cellular behavior.

Most if not all gene delivery systems fall into two categories: systems that mediate irreversible gene integrations (e.g. viral vectors, PhiC31-based systems, plasmids and BACs) and systems that can be excised but leave mutations in the host genome upon excision (e.g. Cre-, Flp- or Sleeping beauty-based systems). These irreversible genetic alterations could potentially lead to higher predisposition towards uncontrolled cellular behavior and they constitute a significant barrier to many clinical applications including the use of hESCs.

The Lepidopteran transposable element piggyBac is capable of excision from the host genome without leaving trace mutations and has been shown to be operable in a wide range of host cells. The PiggyBac transposon isolated from the cabbage looper moth *Trichoplusia ni* (Fraser, M. J., et al. (1996) Insect. Mol. Biol. 5: 141-151) is non-viral, can carry cargo sizes of up to 14.3 Kb, and exhibits higher activity than other transposons in mammalian models (Ding, S., et al. (2005) Cell 122: 473-483; Wilson, M. H., et al. (2007) Mol. Ther. 15: 139-145; Cadiñanos, J., et al. (2007) Nucleic Acid Res. 35: e87). Importantly, PiggyBac does not leave footprint mutations upon remobilization (Wilson, M. H., et al. (2007) Mol. Ther. 15: 139-145). A mouse codon-optimized version of the PiggyBac transposase coding sequence (CDS) has also been disclosed and shown to provide increased transposition levels in murine embryonic stem cells (Cadiñanos, J., et al. (2007) Nucleic Acid Res. 35: e87).

Such a fully reversible method of gene delivery that minimizes concerns of permanent genetic alteration would be desirable in the development of clinically useful therapeutic stem cell applications. However, the wild-type piggyBac element is still limited by the size of its cargo (i.e. transposon insert size) and its transposition efficiency.

SUMMARY OF INVENTION

The present invention relates to compositions, kits and methods for the reversible insertion of exogenous nucleic acid sequences into cells.

Provided herein are nucleic acids comprising an enhanced PiggyBac transposon 5'-terminal repeat sequence. In certain embodiments, the enhanced PiggyBac transposon 5'-terminal repeat sequence comprises a cytosine, guanine, or adenine at a position corresponding to residue number 54 of SEQ ID NO:1 and a thymine, guanine, or adenine at a position corresponding to residue number 137 of SEQ ID NO:1. In certain embodiments, the enhanced PiggyBac transposon 5'-terminal repeat sequence comprises a sequence wherein the residue at a position corresponding to residue number 54 of SEQ ID NO:1 is a cytosine and the residue at a position corresponding to residue number 137 of SEQ ID NO:1 is a thymine. In certain embodiments, the enhanced PiggyBac transposon 5'-terminal repeat sequence provides for an increased frequency of transposition of a exogenous insertion sequence of greater than 14.4 kB in length.

Also provided herein are recombinant DNA constructs comprising an enhanced PiggyBac transposon 5'-terminal repeat sequence. In certain embodiments, a recombinant DNA construct comprising an enhanced PiggyBac transposon 5'-terminal repeat sequence, wherein the enhanced PiggyBac transposon 5'-terminal repeat sequence, when operably linked to a PiggyBac transposon 3'-terminal repeat sequence, provides for an increased frequency of transposition relative to a second recombinant DNA construct comprising a wild-type PiggyBac transposon 5'-terminal repeat sequence operably linked to a PiggyBac transposon 3'-terminal repeat sequence is provided. In certain embodiments, the recombinant DNA construct further comprises a PiggyBac 3' terminal repeat sequence and an exogenous insertion sequence that is operably linked to the 5'-terminal repeat sequence and to the 3'-terminal repeat sequence. In certain embodiments, the 5'-terminal repeat sequence comprises a cytosine, guanine, or adenine at a position corresponding to residue number 54 of SEQ ID NO:1 and a thymine, guanine, or adenine at a position corresponding to residue number 137 of SEQ ID NO:1. In certain embodiments, the 5'-terminal repeat sequence comprises a residue at a position corresponding to residue number 54 of SEQ ID NO:1 is a cytosine and the residue at a position corresponding to residue number 137 of SEQ ID NO:1 is a thymine. In certain embodiments, the recombinant DNA construct further comprises a exogenous insertion sequence that comprises at least one of: i) a sequence for operable insertion of a heterologous DNA sequence; ii) a selectable marker; iii) a counter-selectable marker; iv) a gene encoding a regulatory protein; v) a gene encoding an inhibitory RNA, or any combination thereof. In certain embodiments, the recombinant DNA construct comprises an enhanced PiggyBac transposon 5'-terminal repeat sequence that provides for an increased frequency of transposition of a exogenous insertion sequence of greater than 14.4 kB in length. In certain embodiments, the recombinant DNA comprises an enhanced PiggyBac transposon 5'-terminal repeat sequence that provides for an increased frequency of transposition of a exogenous insertion sequence of 14.4 kB to about 18 kB in length. In certain embodiments, the recombinant DNA construct comprises an enhanced PiggyBac transposon 5'-terminal repeat sequence that comprises a sequence that has at least 80%, 90%, 95%, or 98% sequence identity to SEQ ID NO:1. In certain embodiments, the recombinant DNA construct comprises an enhanced PiggyBac transposon 5'-terminal repeat sequence that comprises SEQ ID NO: 39. In certain embodiments, the recombinant DNA construct comprises an enhanced PiggyBac transposon 5'-terminal repeat sequence that consists of SEQ ID NO:39. In certain embodiments, the recombinant DNA construct further comprises an operably linked PiggyBac transposon 3'-terminal repeat sequence. In certain embodiments, the PiggyBac transposon 3'-terminal repeat sequence comprises a sequence that has at least 90% sequence identity to SEQ ID NO:3. In certain embodiments, an exogenous insertion sequence is operably linked to the 5'-terminal repeat sequence and to the 3'-terminal repeat sequence.

Also provided herein are cells comprising any of the aforementioned nucleic acids of this invention and/or any of the aforementioned recombinant DNA constructs of this invention.

Also provided herein are kits comprising: i) any of the aforementioned nucleic acids of this invention, any of the aforementioned recombinant DNA constructs of this invention, and/or any of the aforementioned cells of this invention and ii) a container. In certain embodiments, the kits can further comprise instructions for the use thereof and/or a recipient nucleic acid molecule. In certain embodiments, any of the aforementioned kits can further comprise a recombinant DNA construct comprising a nucleic acid sequence that encodes a PiggyBac transposase, wherein the nucleic acid sequence comprises a plurality of codons encoding the transposase that are more common to humans than to insects. In certain embodiments, the kits can further comprise a nucleic acid sequence that encodes a PiggyBac transposase has at least 95% sequence identity to SEQ ID NO:4.

Also provided herein are nucleic acids encoding a PiggyBac transposase, wherein the nucleic acid sequence comprises a plurality of codons encoding the transposase that are more common to humans than to insects and has at least 95% sequence identity to SEQ ID NO:4. In certain embodiments, the nucleic acid encodes a PiggyBac transposase comprising a deletion of one or more N-terminal amino acid residues, a deletion of one or more C-terminal amino acid residues, or a combination thereof. In certain embodiments, the nucleic acid encoding a PiggyBac transposase comprises a sequence selected from the group consisting of SEQ ID NO:4 and SEQ ID NO:6. In certain embodiments, the nucleic acid encoding a PiggyBac transposase comprises a sequence has at least 98% identity to SEQ ID NO:4. In certain embodiments, the nucleic acid encodes a PiggyBac transposase of SEQ ID NO: 5 or SEQ ID NO:40. In certain embodiments, the nucleic acid encoding a PiggyBac transposase consists of the sequence of SEQ ID NO:4 or SEQ ID NO:6. In certain embodiments, the nucleic acid encoding a PiggyBac transposase comprises a nucleic acid sequence that further comprises sequences encoding a nuclear localization signal and a DNA binding domain that are operably linked to the N-terminus of the PiggyBac transposase. In certain embodiments, the nucleic acid encoding a PiggyBac transposase comprises a nucleic acid sequence encoding a fusion protein that comprises from N- to C-terminus: i) two copies of a nuclear localization signal; ii) a DNA binding domain; iii) a flexible hinge region; and iv) the PiggyBac transposase, wherein the nuclear localization signals, DNA binding domain, flexible hinge region, and PiggyBac transposase are operably linked. In certain embodiments, the nucleic acid encodes a fusion protein that comprises the protein of SEQ ID NO: 40.

Also provided herein are cells comprising any of the aforementioned nucleic acids of the invention that encode PiggyBac transposases.

Also provided herein are methods for obtaining a cell with a genome comprising a reversibly integrated exogenous DNA insert, the methods comprising the steps of: (a) introducing an enhanced PiggyBac transposon into a cell in the presence of a PiggyBac transposase, wherein the enhanced PiggyBac transposon comprises: i) an operably linked 5'-terminal repeat sequence comprising a cytosine, guanine, or adenine at a position corresponding to residue number 54 of SEQ ID NO:1 and a thymine, guanine, or adenine at a position corresponding to residue number 137 of SEQ ID NO:1; ii) an operably linked exogenous DNA insert; and iii) an operably linked 3' terminal repeat sequence; and, (b) isolating a cell wherein the enhanced PiggyBac transposon has integrated into a genomic sequence of the cell, thereby obtaining a cell with a genome comprising a reversibly integrated exogenous DNA insert. In certain embodiments of the methods, the exogenous DNA insert comprises at least one of: i) a selectable marker; ii) a counter-selectable marker; iii) a gene encoding a regulatory protein; iv) a gene encoding an inhibitory RNA, or any combination thereof. In certain embodiments of the methods, the PiggyBac transposase is operably linked to a DNA binding domain, the DNA binding domain having a high affinity for a corresponding nucleic acid binding site sequence, and wherein the recipient nucleic acid molecule comprises one or more binding site sequences recognized by the DNA binding domain. In certain embodiments, the PiggyBac transposase is provided by: i) co-introduction of the enhanced PiggyBac transposon and a nucleic acid construct that provides for the presence of PiggyBac transposase into the cell; or by ii) introducing the enhanced PiggyBac transposon into a cell comprising a nucleic acid construct that provides for the presence of PiggyBac transposase. In certain embodiments of the methods, the exogenous DNA insert is greater than about 14.4 kB in length. In certain embodiments, wherein the exogenous DNA insert is 14.4 kB to about 18 kB in length. In certain embodiments, the 5'-terminal repeat sequence comprises a sequence wherein the residue at a position corresponding to residue number 54 of SEQ ID NO:1 is a cytosine and the residue at a position corresponding to residue number 137 of SEQ ID NO:1 is a thymine.

Also provided herein are cells obtained by any of the aforementioned methods of obtaining a cell with a genome comprising a reversibly integrated exogenous DNA.

Also provided herein are methods for obtaining a cell that has undergone a reversible genetic modification, the methods comprising: (a) providing a cell with a genome comprising a reversibly integrated enhanced PiggyBac transposon, wherein the enhanced PiggyBac transposon comprises: i) an operably linked 5'-terminal repeat sequence comprising a cytosine, guanine, or adenine at a position corresponding to residue number 54 of SEQ ID NO:1 and a thymine, guanine, or adenine at a position corresponding to residue number 137 of SEQ ID NO:1; ii) an operably linked exogenous DNA insert; and iii) an operably linked 3' terminal repeat sequence with a PiggyBac transposase and a recipient nucleic acid molecule, wherein the recipient nucleic acid molecule can be removed or lost from the cell; b) culturing the cell under conditions that provide for transposition of the PiggyBac transposon to the recipient nucleic acid molecule and subsequent removal or loss of the recipient nucleic acid molecule; and c) isolating a cell comprising a genomic sequence wherein the enhanced PiggyBac transposon has been excised, thereby obtaining a cell that has undergone a reversible genetic modification. In certain embodiments of the methods, the transfer of the PiggyBac transposon from the genome to the recipient nucleic acid molecule returns the sequence of the genome at an original transposon insertion site to exactly its pre-insertion sequence. In certain embodiments of the methods, the 5'-terminal repeat sequence has a residue at a position corresponding to residue number 54 of SEQ ID NO:1 that is a cytosine and has a residue at a position corresponding to residue number 137 of SEQ ID NO:1 that is a thymine. In certain embodiments, the PiggyBac transposase is expressed from a codon-humanized sequence encoding the PiggyBac transposase. In certain embodiments, the PiggyBac transposase is operably linked to a DNA binding domain, the DNA binding domain having a high affinity for a corresponding nucleic acid binding site sequence, and wherein the recipient nucleic acid molecule comprises one or more binding site sequences recognized by the DNA binding domain. In certain embodiments, the DNA binding domain in the PiggyBac transposase is selected from the group consisting of a helix-turn-helix domain, a Zn-finger domain, a leucine zipper domain, and a helix-loop-helix domain. In certain embodiments, the DNA binding domain in the PiggyBac transposase is selected from the group consisting of a Gal4 DNA binding domain, a LexA DNA binding domain, or a Zif268 DNA binding domain. In certain embodiments, the DNA binding domain is a Gal4 DNA binding domain, and the recipient nucleic acid molecule comprises one or more Gal4 UAS binding sites. In certain embodiments, the operably linked exogenous DNA insert comprises one or more sequences encoding one or more gene product(s) that trigger(s) Embryonic Stem Cell (ESC) differentiation. In certain embodiments, the expression of at least one of the one or more gene products is inducible. In certain embodiments, one or more of the gene products inhibit Oct4 expression. In certain embodiments, the operably linked exogenous DNA insert comprises one or more sequences encoding one or more gene products that drive differentiation of a pluripotent cell towards a desired cell fate. In certain embodiments, expression of at least one of the one or more gene products is inducible. In certain embodiments, the desired cell fate is a neural cell type;

and wherein the one or more gene products comprise a Sox1 protein. In certain embodiments, the one or more gene products comprise gene product(s) that inhibit expression of at least one of an Oct4, a Gata6, a Brachyury, or a Cdx2 gene. In certain embodiments, the one or more gene products comprise: i) one or more gene products that inhibit expression of an Oct4, a Gata6, a Brachyury, and a Cdx2 gene and ii) a Sox1 protein. In certain embodiments, the exogenous DNA insert comprises at least one of: i) a selectable marker; ii) a counter-selectable marker; iii) a gene encoding a regulatory protein; iv) a gene encoding an inhibitory RNA, or any combination thereof. In certain embodiments, the DNA insert comprises a counter-selectable marker and wherein the conditions that provide for subsequent removal of the recipient nucleic acid molecule comprise culturing the cell in step (b) in the presence of a counter-selective agent.

Also provided herein are cells obtained by any of the aforementioned methods of obtaining a cell that has undergone a reversible genetic modification.

Also provided herein are methods of obtaining an induced pluripotent stem cell, where the methods comprise: (a) culturing a cell comprising a reversible genetic modification, wherein the reversible genetic modification comprises: i) an enhanced PiggyBac transposon 5'-terminal repeat sequence that is operably linked to ii) a DNA insert that provides one or more gene products that induce the cell to become a pluripotent stem cell that is operably linked to iii) a PiggyBac transposon 3'-terminal repeat sequence, for a period of time sufficient to convert the cell to a pluripotent stem cell; (b) reversing the genetic modification; and (c) isolating a pluripotent stem cell wherein the reversible genetic modification has been removed from the cell, thereby obtaining an induced pluripotent stem cell. In certain embodiments, the pluripotent stem cell is a mammalian cell. In certain embodiments, the mammalian cell is a human cell, a mouse cell, or a rat cell. In certain embodiments, the enhanced PiggyBac transposon 5'-terminal repeat sequence comprises a cytosine, guanine, or adenine at a position corresponding to residue number 54 of SEQ ID NO:1 and a thymine, guanine, or adenine at a position corresponding to residue number 137 of SEQ ID NO:1. In certain embodiments, the DNA insert is greater than 14.4 kB in length. In certain embodiments, the DNA insert is 14.4 kB to about 18 kB in length. In certain embodiments, the DNA insert is up to about 18 kB in length. In certain embodiments, the enhanced PiggyBac transposon 5'-terminal repeat sequence comprises a sequence that has at least 80%, 90%, 95%, or 98% sequence identity to SEQ ID NO:1. In certain embodiments, the one or more gene products that induce the cell to become a pluripotent stem cell comprise Oct4, Sox2 and KLF4 or c-Myc. In certain embodiments, reversing the genetic modification comprises providing the cell from step (a) with a PiggyBac transposase and a recipient nucleic acid molecule, wherein the recipient nucleic acid molecule can be removed or lost from the cell, and culturing the cell under conditions that provide for transposition of the PiggyBac transposon to the recipient nucleic acid molecule and subsequent removal or loss of the recipient nucleic acid molecule. In certain embodiments, the PiggyBac transposase is operably linked to a DNA binding domain, the DNA binding domain having a high affinity for a corresponding nucleic acid binding site sequence, and wherein the recipient nucleic acid molecule comprises one or more binding site sequences recognized by the DNA binding domain. In certain embodiments, the DNA insert further comprises at least one of a selectable marker, a counter-selectable marker, or a combination thereof. In certain embodiments, the gene products of the DNA insert comprise at least one of a gene encoding a regulatory protein; a gene encoding an inhibitory RNA, or a combination thereof. In certain embodiments, the DNA insert comprises a counter-selectable marker and wherein the conditions that provide for subsequent removal of the recipient nucleic acid molecule comprise culturing the cell in step (b) in the presence of a counter-selective agent.

Also provided herein are cells obtained by any of the aforementioned methods of obtaining an induced pluripotent stem cell.

BRIEF DESCRIPTION OF THE DRAWINGS

The accompanying drawings, which are incorporated in and form a part of the specification, illustrate certain embodiments of the present invention and together with the description, serve to explain the principles of the invention. In the drawings:

FIG. 1: FIG. 1A through FIG. 1J demonstrate an engineered PiggyBac transposable element for efficient gene delivery in human and non-primate ESCs.

FIG. 1A: FIG. 1A is a schematic representation of the basic EGFP- or RFP-expressing transposable transgenes. Triangles represent the PiggyBac transposon 5'- and 3'-terminal repeat sequences required for transposition.

FIG. 1B: FIG. 1B illustrates the results of RUES2 cells transfected with a circular plasmid containing the EGFP-expressing transposon (neg.), a linearized plasmid containing the EGFP-expressing transposon (lin.) or a circular plasmid containing the transposon together with a helper plasmid expressing the original PiggyBac transposase (wt) or the codon-humanized PiggyBac transposase (co). Two thousand cells were plated and cultured for 7 days before numbers of fluorescent colonies were determined. The codon-humanized transposase mediated significantly higher gene transfer efficiency ($P<0.01$ co versus wt, n=3 independent repeats)

FIG. 1C: FIG. 1C illustrates the result on gene-transfer efficiency of mutations made to the 5'TR sequence. Twenty 5'TR mutants were generated by random PCR mutagenesis. Mutant number 16, which carries T54C and C137T mutations led to a significant ($P<0.01$ versus control, n=3 independent repeats) increase in gene delivery. The wild type (wt) sequence is SEQ ID NO:2, mutant 1 is SEQ ID NO:45, mutant 2 is SEQ ID NO:46, mutant 3 is SEQ ID NO:47, mutant 4 is SEQ ID NO:48, mutant 5 is SEQ ID NO:49, mutant 6 is SEQ ID NO:50, mutant 7 is SEQ ID NO:51, mutant 8 is SEQ ID NO:52, mutant 9 is SEQ ID NO:53, mutant 10 is SEQ ID NO:54, mutant 11 is SEQ ID NO:55, mutant 12 is SEQ ID NO:56, mutant 13 is SEQ ID NO:57, mutant 14 is SEQ ID NO:58, mutant 15 is SEQ ID NO:59, mutant 16 is SEQ ID NO:1, mutant 17 is SEQ ID NO:60, mutant 18 is SEQ ID NO:61, mutant 19 is SEQ ID NO:62, and mutant 20 is SEQ ID NO:63.

FIG. 1D: FIG. 1D shows that the engineered PiggyBac system composed of the codon-humanized transposase and the T54C/C137T mutant 5'TR mediates efficient gene delivery in hESC lines RUES 2, RUES1, H1, HUES10 and BGN1 as well as Maccaca ESC lines. Scale bars 100 µm.

FIG. 1E: FIG. 1E illustrates the results of inserts of increasing size added to the basic PGK-EGFP transposon. The number of fluorescent colonies was counted 7 days after gene delivery by ePiggyBac (solid bars) or original PiggyBac (open bars). ePiggyBac was able to deliver transgenes of up to 18 Kb with significantly higher efficiency ($P<0.001$ ePiggyBac versus original PiggyBac, n=3 studies).

FIG. 1F: FIG. 1F shows a schematic representation of the hOct4-EGFP transposable element. The 12 Kb transgene includes a neomycin selection cassette (Neo), an HS4 chicken insulator, a 4 Kb human Oct4 promoter driving EGFP expression, and a poly(A) signal (pA).

FIG. 1G: FIG. 1G shows time-lapse imaging of single neomycin-resistant colonies kept undifferentiated in conditioned medium (CM) or differentiated in non conditioned medium (NoCM). Fluorescence levels remain high in undifferentiated cells while they decrease with time as differentiation progresses. Eighteen-day embryoid bodies (EB) have lost most of the hOct4-EGFP labeling. Inset in EB photo shows embryoid body EGFP fluorescence level. Scale bars 100 µm.

FIGS. 1H and 1I: FIGS. 1H and 1I show simultaneous immunohistochemical labeling of both endogenous Oct4 and EGFP in undifferentiated (FIG. 1*h*) and differentiated (FIG. 1*i*) cells. This confirms that EGFP labeling is consistent with endogenous Oct 4 expression. The hOct4-EGFP reporter transgene delivered by ePiggyBac is therefore functional. Scale bars 200 µm.

FIG. 1J: FIG. 1J illustrates the final optimization of transposition parameters: compared to basic gene delivery protocols (basic) disclosed in published data (Siemen, H., et al. (2005) Stem Cells Dev. 14: 378-383). Expressing the transposase from the CAG promoter, using 6 µg of DNA per $1.5 \cdot 10^5$ cells, a transposase/transposon ratio of 1:2 and transfection solution L instead of V (Siemen, H., et al. (2005) Stem Cells Dev. 14: 378-383) (improved) led to a dramatic increase in transgenesis efficiency.

FIG. 2: FIG. 2A through FIG. 2E demonstrate that ePiggyBac retains basic properties of the original PiggyBac system.

FIG. 2A: FIG. 2A is a schematic representation of the plasmid rescue system used to sequence and map integration sites. In addition to the EGFP-expressing cassette, the transposon includes a DNA replication origin and an ampicillin selection cassette. 62 integration sites were sequenced.

FIG. 2B: FIG. 2B illustrates that consensus logo analysis revealed no obvious consensus sequence other than the TTAA tetranucleotide sequence required for PiggyBac transposition.

FIG. 2C: FIG. 2C illustrates that frequency plots revealed a preference for AT-rich regions around the site of integration (SEQ ID NO:74).

FIG. 2D: FIG. 2D shows that ePiggyBac exhibited no hot spot for integration and all chromosomes of the X,X ESC line RUES2 were hit.

FIG. 2E: FIG. 2E shows that distribution of insertions within known transcription units revealed a preference for introns over exons, a 10 Kb window upstream of the transcription start site and a 10 Kb window downstream of the poly(A) site.

FIG. 3: FIG. 3A through FIG. 3G demonstrate that ePiggyBac transposons can be removed from the genome.

FIG. 3A: FIG. 3A is a schematic representation of the transgene integrated in hESC line RUES2. The construct includes a pUC DNA replication origin for plasmid rescue, neomycin/kanamycin phosphotransferase (Neo) and thymidine kinase (TK) cassettes for negative and positive selections respectively, an RFP-expressing insert using the PGK promoter, and SV40 poly(A) (pA) signal, all flanked by the required PiggyBac transposon 5'- and 3'-terminal repeat sequences (triangles).

FIG. 3B: FIG. 3B shows that after neomycin selection, an RFP-positive line containing a single copy of the transgene was established. Scale bar, 100 µm.

FIG. 3C: FIG. 3C shows that upon transfection of the recipient plasmid (R6Kγ-UAS) and Gal4-ePiggyBac helper, colonies exhibit mosaic RFP expression. Scale bar, 100 µm.

FIG. 3D: FIG. 3D illustrates the analyses of 8 plasmid sequences from ampicillin/kanamycin resistant *E. coli* clones. The analysis revealed that the transposon originally carried by the hESC genome (black sequence to the left of the underlined TTAA sequence) has been inserted in the recipient plasmid (grey sequence to the right of the TTAA sequence) at a TTAA junction typical of ePiggyBac transposition. Sequences shown from top to bottom are SEQ ID NO:64 (top), SEQ ID NO:65, SEQ ID NO:66, SEQ ID NO:67, SEQ ID NO:68, SEQ ID NO:69, SEQ ID NO:70, and SEQ ID NO:71 (bottom).

FIG. 3E: FIG. 3E shows that ganciclovir-resistant colonies are only observed after co-transfection of both the Gal4-ePiggyBac helper and R6Kγ-UAS recipient plasmid.

FIG. 3F: FIG. 3F shows that PCR genotyping revealed that gancyclovir-resistant hESC lines (GanR-1 and GanR-2) have reverted from a transgenic (RUES2-RFP) to a wild-type RUES2 genotype (RUES2).

FIG. 3G: FIG. 3G shows sequence analyses illustrating that transgene (RUES2-RFP; dark sequence to the left of underlined TTAA sequence) removal did not leave any mutation in the RUES2 genome (compare RUES2 and Revertant). Chromatogram confirms the absence of mutations in the revertant sequence. Sequences shown from top to bottom are SEQ ID NO:72 (RUES2), SEQ ID NO:73 (RUES2-RFP), SEQ ID NO:72 (Revertant), and SEQ ID NO:72 (sequence directly above the chromatogram).

FIG. 4A through FIG. 4E demonstrate that ePiggyBac transposons can deliver doxycycline-inducible shRNA expressing cassettes to induce hESC differentiation.

FIG. 4A: FIG. 4A is a schematic representation of an shRNA-expressing transposable element. The transgene includes a TetON cassette, a neomycin selection cassette (Neo), an HS4 chicken insulator (Ins), a Tet-responsive elements (TRE) driving shRNA expression, and a poly(A) signal (pA), all flanked by the required PiggyBac transposon 5'- and 3'-terminal repeats sequences (triangles).

FIG. 4B: FIG. 4B shows quantitative RT-PCR analyses performed four days after the addition of doxycycline (+DOX). The expression of pluripotency markers Oct4, Sox2 and Nanog decreases whereas levels of differentiation markers Gata6, Sox1, Brachyury and Cdx2 increases compared to samples grown in the absence of doxycycline (−DOX) or in cells expressing a control anti-EGFP shRNA (shEGFP+DOX).

FIG. 4C and FIG. 4D: FIG. 4C shows cells grown in the absence of doxycycline, which formed tightly packed colonies characteristic of undifferentiated hESCs whereas FIG. 4D shows cells expressing the anti-Oct4 shRNA which exhibited a flattened morphology reminiscent of differentiated cells. Scale bars 30 μm.

FIG. 4E: FIG. 4E shows that morphological changes were accompanied by a loss in Oct4 immunoreactivity and a strong increase in immunoreactivity for the trophectoderm marker cytokeratin 18. Scale bars 50 μm.

FIG. 5: FIG. 5A through FIG. 5G demonstrate that ePiggyBac transposons can direct hESC differentiation toward a neural phenotype and be removed.

FIG. 5A: FIG. 5A shows quantitative RT-PCR analyses indicating that in hESCs transfected with a cocktail of gain- and loss-of-function transposons, expression of pluripotency markers significantly decrease upon doxycycline treatment and the expression of neuroectodermal marker Pax6 and neural-specific genes Sox1 and NFH is preponderant over that of endodermal (Mixl1, Sox17), mesodermal (Chordin) and trophectodermal (hCG beta) markers.

FIG. 5B and FIG. 5C FIG. 5B shows neural rosettes. FIG. 5C shows that the neural rosettes exhibiting Pax6- and Nestin-immunoreactivity also appear in doxycycline-treated cultures. Scale bars 50 μm (b), 5 μm (c).

FIGS. 5D-5G: FIG. 5D shows that upon transgene removal, ganciclovir-resistant neural spheres are selected. These neural spheres give rise to nestin- (FIG. 5E), doublecortin (DCX)-, NFH- (FIG. 5F) and Map2-positive (FIG. 5G) neurons. Scale bars 100 μm (D), 20 μm (E, G), 10 μm (F).

FIG. 6: Nucleotide sequence of the codon-humanized ePiggyBac transposase (SEQ ID NO:4) and amino acid sequence alignment between the wild-type transposase (SEQ ID NO:5) and enhanced transposase (SEQ ID NO:5) showing that transposase is unaltered at the protein level.

FIG. 7: Nucleotide sequence of 5'TR mutant 16 (SEQ ID NO:1) and alignment with the wild-type (wt) sequence (SEQ ID NO:2) to indicate T54C and C137C mutations that improve gene delivery in hESCs.

FIG. 9A through FIG. 9D demonstrate that transgenic hESCs remain pluripotent and able to differentiate into all three germ layers.

FIG. 9A: FIG. 9A shows immunohistochemical detection of pluripotency markers Oct3/4, Sox2 and Nanog in RUES2 after gene transfer using ePiggyBac. Scale bars 100 μm.

FIG. 9B and FIG. 9C: FIG. 9B shows that transgenic PGK-EGFP RUES2 cells are able to form embryoid bodies. FIG. 9C shows that these cells exhibit strong fluorescence. Scale bars 500 μm.

FIG. 9D: FIG. 9D shows immunohistochemical detection of endodermal marker Gata 6, mesodermal marker muscle actin (M. actin) and neurofilament heavy chain (NFH) in differentiated transgenic RUES2. Insets show sytox orange nuclear counter stain. Scale bars 100 μm.

FIG. 10A through FIG. 10F confirm by histological analyses of teratomas that upon transposition, hESCs remain able to differentiate into all three germ layers.

FIG. 10A: FIG. 10A shows green fluorescence conferred by the basic EGFP-expressing transposon (see FIG. 1A) in an 8-week old teratoma. Scale bars 100 μm.

FIGS. 10B-10F: Hematoxylin and eosin staining demonstrates the presence of derivatives of all three germ layers including: cartilage (1), squamous keratin epithelium (2), blood vessels (3), bone (4), connective tissue (5), ductular epithelium (6), muscle tissue (7), neural tissue (8), adipose tissue (9) and pseudostratified epithelium (10). Scale bars 100

FIG. 11 is a schematic representation of the removal system. The helper plasmid expresses a fusion between the Gal4 DNA binding domain (Gal4) and the ePiggyBac transposase (Gal4-ePBac). The recipient plasmid includes an ampicillin resistance cassette (Amp), 14 repeats of the Gal4 UAS sequence and an R6Kγ DNA replication origin. Upon expression, the chimeric Gal4-ePBac transposase binds to the Gal4 UAS sequences to increase the odds that transposons are transferred to the recipient plasmid. The R6Kγ DNA replication origin is only active in *E. coli* strains that provide the π protein encoded by the pir gene. DH5α *E. coli* strains used in this study for plasmid rescue are pir-, therefore upon expression of Gal4-ePiggyBac and DNA extraction from hESCs, the recipient plasmid can only give rise to ampicillin-resistant DH5α colonies if a transposon containing a pUC replication origin has been inserted in the recipient plasmid. In addition, the modified plasmid resulting from integration of the transposon into the recipient plasmid only contains one functional replication origin in DH5α strains. This reduces possible replication defects and decreases in plasmid rescue efficiency due to interference between two replication origins in the same plasmid.

FIG. 12A shows RT minus controls for quantitative RT-PCR analyses shown in FIG. 4B.

FIG. 12B shows high magnification images showing that cells grown in the absence of doxycycline, exhibit strong nuclear Oct4-immunofluorescence characteristic of undifferentiated hESCs whereas cells in FIG. 12c expressing the anti-Oct4 shRNA exhibit immunoreactivity for the trophectoderm marker cytokeratin 18 in filamentous structures characteristic of epithelial cell types. Scale bar 20 µm.

FIG. 20. The sequence of the cassette [5'TR-MCS-pA-3'TR] (SEQ ID NO: 44). Note that the 5'TR and 3'TR sequences are underlined, the MCS sequence is in uppercase and bold, and the pA (polyadenylation) sequence is in small caps and italics.

FIG. 21A, B, C, D, E. An alignment of the indicated wild type (wt) and mutant 5'TR sequences are shown with the mutant sequences corresponding to those tested in FIG. 1C. Residues in the mutants that differ from wild type are underlined. The wild type (wt) sequence is SEQ ID NO:2, mutant 1 is SEQ ID NO:45, mutant 2 is SEQ ID NO:46, mutant 3 is SEQ ID NO:47, mutant 4 is SEQ ID NO:48, mutant 5 is SEQ ID NO:49, mutant 6 is SEQ ID NO:50, mutant 7 is SEQ ID NO:51, mutant 8 is SEQ ID NO:52, mutant 9 is SEQ ID NO:53, mutant 10 is SEQ ID NO:54, mutant 11 is SEQ ID NO:55, mutant 12 is SEQ ID NO:56, mutant 13 is SEQ ID NO:57, mutant 14 is SEQ ID NO:58, mutant 15 is SEQ ID NO:59, mutant 16 is SEQ ID NO:1, mutant 17 is SEQ ID NO:60, mutant 18 is SEQ ID NO:61, mutant 19 is SEQ ID NO:62, and mutant 20 is SEQ ID NO:63.

DETAILED DESCRIPTION OF THE INVENTION

Figure 4:
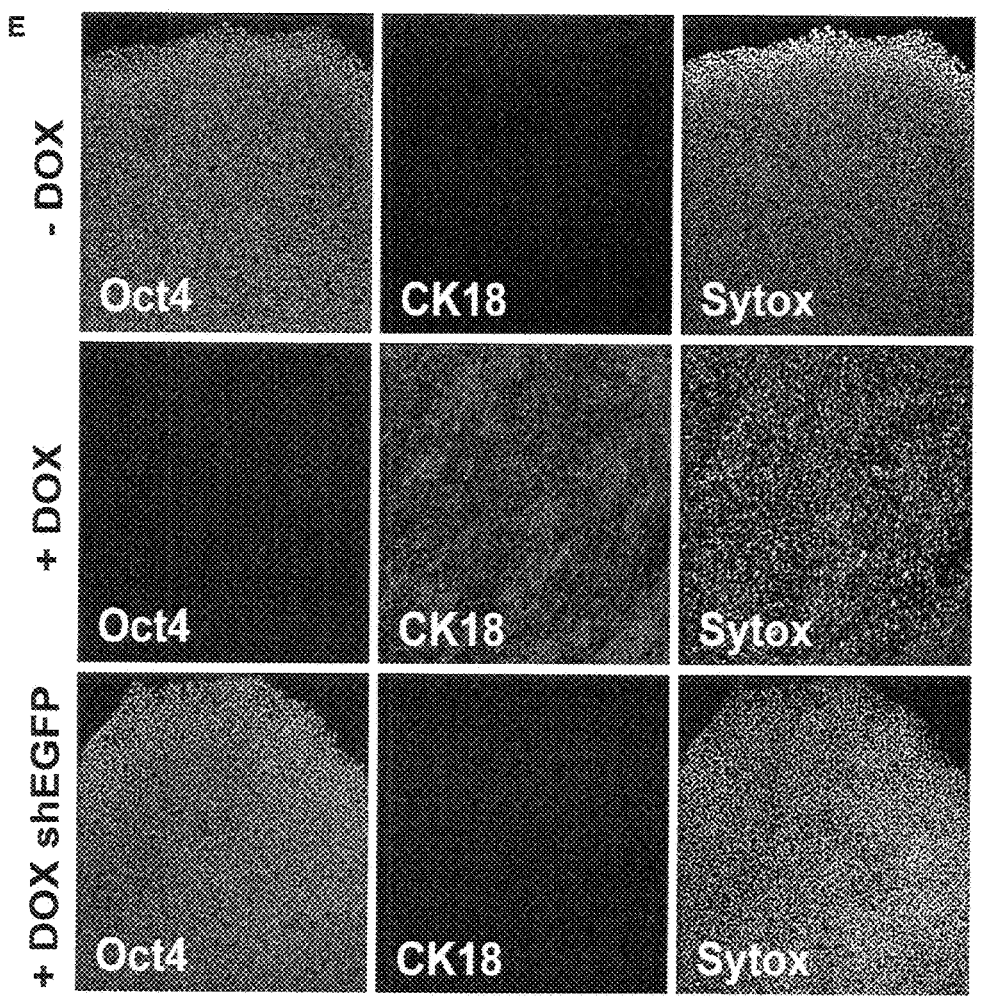
FIG. 4.

An enhanced version of the PiggyBac transposon and an enhanced sequence encoding a PiggyBac transposase and kits comprising the same are provided herein. In certain embodiments, the enhanced PiggyBac transposon, the enhanced sequence encoding a PiggyBac transposase, and/or a transposition system comprising the two provide for an increased frequency of transposition and/or an increased transposition cargo capacity. Methods of utilizing the enhanced PiggyBac components are also provided. It is demonstrated that such compositions and methods are useful in obtaining cells with a genome comprising a reversibly integrated exogenous DNA insertion sequence and for obtaining cells that have undergone a reversible genetic modification.

DEFINITIONS

Unless otherwise defined, all technical and scientific terms used herein have the same meaning as commonly understood by one of ordinary skill in the art to which this invention pertains. To the extent to which any of the following definitions is inconsistent with definitions provided in any patent or non-patent reference incorporated herein or in any reference found elsewhere, it is understood that the following definition will be used herein.

As used herein, the phrase "recombinant DNA construct", refers to any DNA molecule that results from the combination of DNA sequences from different sources. Examples of DNA constructs include, but are not limited to, plasmids, cosmids, viruses, BACs (bacterial artificial chromosomes), YACs (yeast artificial chromosomes), autonomously replicating sequences, phage, or linear or circular single-stranded or double-stranded DNA sequences, derived from any source, that are capable of genomic integration and/or autonomous replication. DNA constructs can be assembled by a variety of methods including, but not limited to, recombinant DNA techniques, DNA synthesis techniques, PCR (Polymerase Chain Reaction) techniques, or any combination thereof.

As used herein, the phrase "enhanced PiggyBac" or "ePiggyBac" refers to a PiggyBac transposon and/or PiggyBac transposase that provides for an increased frequency of transposition relative to a wild-type PiggyBac transposon and/or transposase.

As used herein, the phrase "enhanced PiggyBac transposon 5'-terminal repeat sequence" refers to a PiggyBac transposon 5'-terminal repeat sequence that has been mutated such that when operably linked to a PiggyBac transposon 3'-terminal repeat, it provides for an increased frequency of transposition relative to a second recombinant DNA construct comprising a wild-type PiggyBac transposon 5'-terminal repeat sequence operably linked to a PiggyBac transposon 3'-terminal repeat sequence.

As used herein, the phrase "wild-type PiggyBac transposon 5'-terminal repeat sequence", refers to the PiggyBac transposon 5'-terminal repeat sequence isolated from the cabbage looper moth Trichoplusia ni.

As used herein, the phrase "enhanced PiggyBac transposon", refers to a PiggyBac transposon that provides for an increased frequency of transposition relative to a wild-type PiggyBac transposon. In certain embodiments, mutations in the 5'-terminal repeat sequence provide for the increased frequency of transposition.

As used herein, the phrase "operably linked", refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration and/or excision functions (i.e., transposon sequences, transposase-encoding sequences, site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences), and sequences that provide replication functions (i.e., bacterial origins of replication, autonomous replication sequences, centromeric sequences).

As used herein, the phrase "position corresponding to", when used in the context of comparing, aligning, or identifying equivalent nucleotides or amino acids in one nucleic acid or amino acid sequence respectively, with another nucleic acid or amino acid sequence, refers to the comparison or alignment that will yield the highest percent identity when aligned with the other nucleic acid or amino acid sequence.

As used herein, the phrases or terms "sequence identity", "sequence similarity" or "homology" is used to describe sequence relationships between two or more nucleic acid or two or more amino acid sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

As used herein, the phrases "PiggyBac transposon 3'-terminal repeat sequence" or "wild-type PiggyBac transposon 3'-terminal repeat sequence" refers to the PiggyBac transposon 3'-terminal repeat sequence isolated from the cabbage looper moth *Trichoplusia ni.*

As used herein, the phrases, "exogenous DNA insertion sequence", "exogenous insertion sequence", "exogenous DNA insert", or the like refers to any sequence derived from a source other than the native transposon that is operably linked to transposon sequences.

As used herein, the term "encodes" refers to the capacity of a nucleic acid to provide another nucleic acid or a polypeptide. A nucleic acid sequence or construct is said to "encode" a polypeptide if it can be transcribed and/or translated to produce the polypeptide.

As used herein, the phrase "increased frequency of transposition", refers to any increase in the number of integrative and/or excisive transposition events.

As used herein, the term "PiggyBac transposase", refers to the transposase isolated from the cabbage looper moth *Trichoplusia ni*, or the nucleic acid sequence encoding said transposase.

As used herein, the phrase "codon-humanized sequence", refers to a coding sequence wherein the number of codons that occur more frequently in human genes is increased relative to the coding sequence obtained from the original source.

As used herein, the term "reversibly integrated", refers to the ability of the PiggyBac transposon that is inserted into a site in a cell's genome to be remobilized by excision from the insertion site such that the sequence of the insertion site in the cell's genome is restored to the sequence present at that site in the cell's genome prior to insertion of the transposon.

As used herein, the term "reversible genetic modification", refers to a modification in a cell's genome that can be reversed to restore the genome back to its pre-modification sequence. A reversibly integrated PiggyBac transposon is an example of a reversible genetic modification.

As used herein, the term "removed or lost", when referring to a nucleic acid construct refers to any active or passive process whereby a construct introduced into a cell is induced or permitted to disappear from the cell or from one or more daughter cell(s) derived from a parent cell.

As used herein, the term "Gal4 UAS binding site" refers to any DNA sequence that permits recognition and binding by a GAL4 DNA binding domain or protein attached thereto.

As used herein, the term "gene products", refers to either an RNA molecule or to a polypeptide resulting from the expression of a DNA sequence encoding for the RNA molecule or polypeptide.

As used herein, the term "regulatory protein", refers to any protein that: increases or decreases the activity of another polypeptide or RNA molecule; increases or decreases the abundance or another polypeptide or RNA molecule; alters the interaction between another polypeptide or RNA molecule with other polypeptides, DNA or RNA molecules, or any other binding substrates; and/or alters the cellular location of another polypeptide or RNA molecule.

I. Recombinant DNA Constructs Comprising an Enhanced PiggyBac Transposon 5'-Terminal Repeat Sequence.

In certain embodiments of the present invention a recombinant DNA construct comprises an enhanced PiggyBac transposon 5'-terminal repeat sequence. The wild-type Pigybac transposon comprising a wild-type 5'-terminal repeat sequence and an operably linked 3'-terminal repeat sequence is active, albeit at low transposition frequencies, in hESCs. Certain mutations to the wild-type Pigybac transposon 5'-terminal repeat sequence have been demonstrated herein to increase the frequency of transposition of a PiggyBac transposon comprising such a mutated 5'-terminal repeat sequence. Those same mutations have also been demonstrated herein to provide for an increased frequency of transposition of transposon inserts of greater than 14.4 kb in length. Thus, a mutated 5'-terminal repeat sequence that provides for an increased frequency of transposition in comparison to the wild-type frequency and/or an increased frequency of transposition of transposon inserts of greater than 14.4 kb in length is considered an enhanced 5'-terminal repeat sequence. In certain embodiments, such an increase in transposition frequency can be determined as being any statistically significant increase over the wild-type frequency. An increase in transposition frequency for an enhanced transposon provided herein can be at least about a 10%, 20%, 30,%, 40%, 50%, or about a 60% increase in frequency over the frequency obtained for the wild-type transposon comprising a wild-type PiggyBac 5'-terminal repeat sequence.

Certain embodiments of the present invention contemplate any recombinant DNA construct comprising a PiggyBac transposon 5'-terminal repeat sequence that provides for an increase in transposition frequency. It is anticipated that mutations can be introduced into the PiggyBac transposon 5'-terminal repeat sequence and screened for their ability to confer an increased transformation efficiency and/or an increased transposon insert size (i.e. cargo capacity) using methods provided herein. Although the majority of random mutations made to the 5'-terminal repeat sequence do not increase the frequency of transposition in hESCs and certain mutations decrease the efficiency of transposition (FIG. 1C), substitution mutations that increase transpositions efficiency have been identified herein. Thus, recombinant DNA constructs comprising an enhanced PiggyBac transposon 5'-terminal repeat sequence that provides for an increase in transposition frequency are provided herein.

A recombinant DNA construct provided herein can comprise an enhanced PiggyBac transposon 5'-terminal repeat sequence that comprises nucleotide substitutions at two or more positions in the sequence relative to a wildtype PiggyBac transposon 5'-terminal repeat sequence. In certain embodiments of the present invention, nucleotides at positions in an enhanced PiggyBac transposon 5'-terminal repeat sequence corresponding to position 54 and position 137 of SEQ ID NO:1 are non-wild-type nucleotide residues. Therefore, certain embodiments of the present invention provide for a recombinant DNA construct comprising an enhanced PiggyBac transposon 5'-terminal repeat sequence comprising non-wild-type nucleotide residues at positions corresponding to residues 54 and 137 of SEQ ID NO:1. The wild-type residue at the position corresponding to residue number 54 of SEQ ID NO:1 is a thymine and the wild-type residue at the position corresponding to residue number 137 of SEQ ID NO:1 is a cytosine. The reference wild-type PiggyBac transposon 5'-terminal repeat sequence wherein the residue at the position corresponding to residue number 54 of SEQ ID NO:1 is thymine and the residue at the position corresponding to residue number 137 of SEQ ID NO:1 is cytosine is provided herein as SEQ ID NO:2. Thus, the enhanced PiggyBac transposon 5'-terminal repeat can comprise a cytosine, guanine, or adenine residue at the position corresponding to residue number 54 of SEQ ID NO:1 and a thymine, guanine, or adenine residue at the position corresponding to residue number 137 of SEQ ID NO:1. In certain embodiments, an enhanced PiggyBac transposon 5'-terminal repeat sequence can comprise SEQ ID NO:39, wherein a cytosine is at the position corresponding to residue number 54 of SEQ ID NO:1 and wherein a thymine is at the position corresponding to residue number 137 of SEQ ID NO:1.

In still other embodiments, a recombinant DNA construct provided herein can comprise an enhanced PiggyBac transposon 5'-terminal repeat sequence comprising at least one mutation. In certain embodiments of the present invention, a nucleotide at a position in an enhanced PiggyBac transposon 5'-terminal repeat sequence corresponding to either position 54 or position 137 of SEQ ID NO:1 is substituted with a non-wild-type nucleotide residue. Therefore, certain embodiments of the present invention provide for a recombinant DNA construct comprising an enhanced PiggyBac transposon 5'-terminal repeat sequence comprising non-wild-type nucleotide residues at positions corresponding to residues 54 or 137 of SEQ ID NO:1. The wild-type residue at the position corresponding to residue number 54 of SEQ ID NO:1 is a thymine and the wild-type residue at the position corresponding to residue number 137 of SEQ ID NO:1 is a cytosine. The reference wild-type PiggyBac transposon 5'-terminal repeat sequence wherein the residue at the position corresponding to residue number 54 of SEQ ID NO:1 is thymine and the residue at the position corresponding to residue number 137 of SEQ ID NO:1 is cytosine is provided herein as SEQ ID NO:2. Thus, the enhanced PiggyBac transposon 5'-terminal repeat sequence can comprise a cytosine, guanine, or adenine residue at the position corresponding to residue number 54 of SEQ ID NO:1 or can comprise a thymine, guanine, or adenine residue at the position corresponding to residue number 137 of SEQ ID NO:1. In certain embodiments, an enhanced PiggyBac transposon 5'-terminal repeat sequence can comprise a sequence wherein a cytosine is substituted at the position corresponding to residue number 54 of SEQ ID NO:1. In certain embodiments, an enhanced PiggyBac transposon 5'-terminal repeat sequence can comprise a sequence wherein a thymine is substituted at the position corresponding to residue number 137 of SEQ ID NO:1.

Enhanced PiggyBac transposon 5'-terminal repeat sequences that combine a non-wild-type residue at either position 54 or position 137 of SEQ ID NO:1 with one or more non-wild-type residues at other nucleotide sequence positions of SEQ ID NO:1 are also provided herein. In certain embodiments, an enhanced PiggyBac transposon 5'-terminal repeat sequence that combines a cytosine residue at either position 54 or a thymine residue at position 137 of SEQ ID NO:1 with one or more non-wild-type residues at other nucleotide sequence positions of SEQ ID NO:1 is provided.

An enhanced PiggyBac transposon 5'-terminal repeat sequence can be altered through nucleotide substitutions, nucleotide insertions, and/or nucleotide deletions without destroying its function. It is further contemplated that certain insertions and/or certain deletions can be made in an enhanced PiggyBac transposon 5'-terminal repeat sequence at positions corresponding to residues other than residues 54 and 137 of SEQ ID NO:1 without altering the efficiency of transposition. Insertions and/or deletions at positions corresponding to residues other than residues 54 and 137 of SEQ ID NO:1 can comprise insertions and/or deletions of 1, 2, 3, 4, 5, 6 nucleotides. Certain embodiments of the present invention provide for enhanced PiggyBac transposon 5'-terminal repeat sequences that comprise non-wild type nucleotides at positions corresponding to residues 54 and 137 of SEQ ID NO:1, and further have at least 80%, 90%, 95%, 98, or 99% sequence identity to SEQ ID NO:1. Certain embodiments provide for an enhanced PiggyBac transposon 5'-terminal repeat sequences that comprise a cytosine at a position corresponding to residue number 54 of SEQ ID NO:1, a thymine at a position corresponding to residue number 137 of SEQ ID NO:1, and further have at least 80%, 90%, 95%, 98, or 99% sequence identity to SEQ ID NO:1. Enhanced PiggyBac transposon 5'-terminal repeat sequences that have at least 80%, 90%, 95%, 98%, or 99% sequence identity to SEQ ID NO:39 are also provided herein.

In order to mediate transposition of an exogenous DNA insertion sequence into the genome of a host cell, the PiggyBac transposon requires both 5'- and 3'-terminal repeat sequences. Terminal repeat sequences can be operably linked to an exogenous DNA insertion sequence by placement at the 5'- and 3-flanking termini of the insertion sequence. SEQ ID NO:3 is the wild-type PiggyBac 235 bp minimal 3'-terminal repeat sequence. As with the 5'-terminal repeat sequence, mutations may be introduced into the wild-type 3'-terminal repeat sequence without destroying its ability to mediate transposition. Certain embodiments of the present invention provide for a recombinant DNA construct comprising an enhanced PiggyBac transposon 5'-terminal repeat sequence and further comprising an operably linked PiggyBac transposon 3'-terminal repeat sequence. In certain embodiments, the PiggyBac transposon 3'-terminal repeat sequence comprises a sequence that has at least 80%, 90%, 95%, 98%, or 99% sequence identity to SEQ ID NO:3.

The enhanced PiggyBac transposon of the present invention can be used to insert an exogenous DNA insertion sequence into the genome of a host cell. The transposon containing the operably linked exogenous DNA insertion sequence can serve to disrupt the host cell's genomic sequence at the site of insertion. The exogenous DNA insertion sequence can also comprise a variety of useful sequences such as sequences encoding markers for visualization (i.e. reporter genes) or selection, transcription factors, inhibitory RNA sequences, and/or other gene products that can alter the phenotype of the cell. Often, such sequences will be operably linked to other sequences such as promoter sequences, enhancer or regulatory sequences, and polyadenylation sequences, untranslated regions, and intronic sequences that allow for, regulate, and/or increase the expression of the a gene product. Other useful sequences include, but are not limited to, insulator sequences, and/or origins of replication. The use of operably linked sequences that permit expression of multiple gene products that are encoded by a single primary transcript is also provided. Sequences that permit expression of multiple gene products include, but are not limited to, internal ribosome entry sites and/or protease recognition sites.

In certain embodiments, recombinant DNA constructs provided herein can comprise a sequence for operable insertion of an exogenous DNA insertion sequence, where the sequence that provides for operable insertion is flanked at it's 5' terminus to an enhanced PiggyBac transposon 5'-terminal repeat sequence and flanked at it's 3' terminus to a PiggyBac transposon 3'-terminal repeat sequence. A sequence for operable insertion of an exogenous DNA sequence can comprise any sequence that permits operable insertion of an exogenous sequence into the transposon such that the inserted sequence can be transposed In certain embodiments, a sequence for operable insertion of an exogenous sequence comprises at least one restriction endonuclease recognition sequence. In still other embodiments, a sequence for operable insertion of an exogenous DNA sequence can comprise a site for integration by homologous recombination. In still other embodiments, a sequence for operable insertion of an exogenous DNA sequence can comprise a site-specific recombination recognition sequence. Examples of site-specific recombination recognition sequences include, but are not limited to, lox sites recognized by a bacteriophage P1 Cre recombinase, or FRT sites recognized by a yeast FLP recombinase. In still other embodiments, a sequence for operable insertion of an exogenous DNA sequence can comprise a Ligation Independent Cloning site that provides for DNA topoisomerase I mediated integration of the heterologous coding sequence. Various methods for operable insertion of exogenous sequences into specified sites in U.S. Pat. No. 7,109,178, which is incorporated herein by reference with respect to its disclosure of Ligation Independent Cloning and directional cloning.

Certain embodiments of the current invention allow for the transposition of large exogenous DNA insertion sequences. The ability to insert large sequences into the genome of a host cell is advantageous. Such ability can allow for the introduction of multiple components such as expression cassettes, insulator sequences, plasmid rescue systems, and other sequences with a variety of cellular functions. Such complexity and/or increased insertion sequence size may be required to determine, alter, or reverse cellular characteristics including, but not limited to, developmental fate, differentiation stage, and/or metabolic state. Previously described versions of the PiggyBac system have been limited in the size of exogenous sequence that they are able to insert. The use of a mouse optimized PiggyBac system that allows for the insertion of sequences up to 14.3 kB in length was reported (Ding, S., et al. (2005) Cell 122: 473-483). It is demonstrated herein that the enhanced PiggyBac transposon system of the current invention allows for insertion of sequences of greater than 14.3 or 14.4 kB in length and up to at least about 18 kB in length at significantly higher transposition efficiencies than the original wildtype PiggyBac transposon that comprises a wild-type 5'- and 3'-terminal repeat sequence.

Certain embodiments of the current invention provide for a cell comprising a recombinant DNA construct, the DNA construct comprising an enhanced PiggyBac transposon 5'-terminal repeat sequence. As described herein, the original wild-type PiggyBac transposon system has been mutated to enhance its ability to mediate transposition in cells. The enhanced PiggyBac transposon system provided herein can provide increased transposition efficiency in human embryonic stem cell lines (hESC) relative to wild-type PiggyBac transposon systems. Increased transposition efficiency of the enhanced PiggyBac transposon system provided herein can be observed in hESC lines including, but not limited to, RUES2, RUES1, H1, HUES10, and BGN1. The enhanced PiggyBac system can also provide increased transposition efficiency mediate efficient transposition in non-human primate embryonic cell lines relative to wild-type PiggyBac transposon systems. Increased transposition efficiency of the enhanced PiggyBac transposon system provided herein can be observed in non-human primate embryonic cell lines that include, but are not limited to, *Macacca fascicularis, M. nemestrina*, and *M. mulatta*. The PiggyBac transposon has also been shown to be capable of transposition in a variety of vertebrate cells such as mouse and zebra fish (*Danio rerio*). Thus, the use of the enhanced PiggyBac transposon systems provided herein is not limited to human or primate cells, but also extends to use in other vertebrate cells. Further, the original PiggyBac transposon was isolated from an invertebrate species, and is functional in numerous invertebrate species. Thus, the use of the enhanced PiggyBac transposon systems provided herein also extends to use in an invertebrate cell.

II. Recombinant DNA Constructs Comprising a Nucleic Acid Sequence that Encodes a Piggybac Transposase and Related Methods of Use SEQ ID NO:5 is the amino acid sequence of the PiggyBac transposase and SEQ ID NO:41 is the original or wild-type nucleic acid sequence isolated from cabbage looper moth that encodes the PiggyBac transposase. Due to the degeneracy of the genetic code, one or more of the wild type codons present in a PiggyBac transposase gene obtained from the cabbage looper moth can be substituted with one or more synonymous codons to obtain a distinct sequence that encodes the same functional PiggyBac transposase as the wild-type PiggyBac transposase gene from cabbage looper moth.

In order to optimize expression of a sequence, it can be advantageous to introduce synonymous changes to one or more codons in the coding region of the sequence. Without seeking to be limited by theory, the substitution of codons that are more common to the organism in which expression is desired than to the organism from which the sequence was originally identified can contribute to improved expression. Such substitutions can also result in a change in the A+T content of a coding sequence that can be advantageous in the context of achieving expression in certain organisms characterized by having genes with certain A+T content (U.S. Pat. No. 5,500,365). However, such changes in the codon usage can also inadvertently introduce sequences that reduce expression (U.S. Pat. No. 5,689,052).

Provided herein are nucleic acids comprising codon-humanized sequences that encode PiggyBac transposases wherein the number of codons that occur more frequently in human genes is increased relative to the coding sequence obtained from *Trichoplusia*. In one exemplary embodiment, a codon-humanized sequence that encodes a PiggyBac transposase wherein the sequence comprises a plurality of codons encoding the transposase that are more common to humans than to insects is provided as SEQ ID NO:4. Also provided herein are additional codon-humanized variants of SEQ ID NO:4 comprising a nucleic acid sequence that encodes for a PiggyBac transposase and that has at least 95%, 96%, 97%, 98%, or 99% sequence identity to SEQ ID NO:4. In certain embodiments, such sequence that encodes for a PiggyBac transposase can comprise or consist of SEQ ID NO:4.

It is well known in the art that the function, activity, etc., of a polypeptide does not necessarily require the full length of the polypeptide as originally identified. In some cases, removal of a portion of a polypeptide chain has an insubstantial effect on its activity. In some cases, it can be desirable to remove portions of a polypeptide chain, for instance to express an active peptide instead of an inactive pro-form, or to remove a localization signal. It is thus contemplated that certain deletions can be made to either one or more N-terminal residues, one or more C-terminal residues, or a combination of N-terminal and C-terminal residues of a sequence that encodes a PiggyBac transposase.

Operably linked fusions of certain protein functional domains to a PiggyBac transposase encoded by a codon-humanized gene are also provided herein. Such protein functional domains can include, but are not limited to, one or more DNA binding domains, one or more nuclear localization signals, one or more flexible hinge regions that can facilitate one or more domain fusions, and combinations thereof. Fusions can be made either to the N-terminus, C-terminus, or internal regions of the transposase protein so long as transposase activity is retained. In certain embodiments, a fusion protein provided herein can comprise a nuclear localization signal and DNA binding domain that are operably linked to the N-terminus of the PiggyBac transposase encoded by a codon-humanized gene. In still other embodiments, a fusion protein provided herein can comprise, from N- to C-terminus: i) two copies of a nuclear localization signal; ii) a DNA binding domain; iii) a flexible hinge region; and iv) a PiggyBac transposase encoded by a codon-humanized sequence, wherein the nuclear localization signals, DNA binding domain, flexible hinge region, and PiggyBac transposase are operably linked. Nuclear localization signals (NLS) used can include, but are not limited to, consensus NLS sequences, viral NLS sequences, cellular NLS sequences, and combinations thereof. DNA binding domains used can include, but are not limited to, a helix-turn-helix domain, a Zn-finger domain, a leucine zipper domain, or a helix-loop-helix domain. Specific DNA binding domains used can include, but are not limited to, a Gal4 DNA binding domain, a LexA DNA binding domain, or a Zif268 DNA binding domain. Flexible hinge regions used can include, but are not limited to, glycine/serine linkers (i.e. (Gly4Ser)3 (SEQ ID NO: 75) and variants thereof.

Certain embodiments of the current invention provide for a cell comprising a recombinant DNA construct comprising a codon-humanized gene that encodes a PiggyBac transposase as described above. The cell of certain embodiments of the present invention is not limited to human or primate cells, but encompasses all vertebrate cells. Further, the cell of certain embodiments of the present invention encompasses invertebrate species as well.

III. Kit Comprising a Recombinant DNA Construct Comprising ePiggyBac

In certain embodiments, a kit is provided that comprises a recombinant DNA construct comprising an enhanced PiggyBac transposon 5'-terminal repeat sequence and a container. The recombinant DNA construct can be provided in a kit in a variety of forms. Isolated nucleic acids can be provided in forms that include, but not limited to, as an isolated nucleic acid wherein the nucleic acid is not contained within a cell, or provided within a transformed cell or a population of transformed cells. An isolated nucleic acid can be provided in a liquid solution or it can be provided as a lyophilisate. In embodiments wherein the nucleic acid is provided in a liquid solution, such solution can be aqueous solution. The aqueous solution can be a buffered solution that stabilizes nucleic acids.

The recombinant DNA construct of the kit comprising an enhanced PiggyBac transposon 5'-terminal repeat sequence can comprises a variety of other sequences operably linked to the 5'-terminal repeat sequence such as a PiggyBac transposon 3'-terminal repeat sequence and exogenous DNA insertion sequences as described above. In certain embodiments, kits provided herein can comprise a sequence for operable insertion of an exogenous DNA insertion sequence, where the sequence that provides for operable insertion is flanked at it's 5' terminus to an enhanced PiggyBac transposon 5'-terminal repeat sequence and flanked at it's 3' terminus to a PiggyBac transposon 3'-terminal repeat sequence. Kits provided herein can also further comprise a recombinant DNA construct comprising a nucleic acid sequence that encodes a PiggyBac transposase. In certain embodiments, kits provided herein can comprise PiggyBac transposase enzyme. Thus, a kit can provide for some or all of the nucleic acid sequences necessary for transposition of a PiggyBac transposon into a host cell genome and/or sequences necessary for excision of an integrated transposon from a host cell genome. Kits provided herein can additionally provide for exogenous DNA insertion sequences that encode for gene products to be expressed in a host cell. Kits provided herein can also comprise a recipient nucleic acid that comprises one or more copies of a nucleic acid binding site sequence that is bound with high affinity by a corresponding protein DNA binding site domain.

The sequence that encodes for a PiggyBac transposase can comprise the wild-type transposase sequence or a codon-humanized PiggyBac transposase sequence. Thus in certain embodiments, kits provided herein can comprise a recombinant DNA construct comprising a nucleic acid sequence that encodes for a PiggyBac transposase that has at least 95%, 96%, 97%, 98% or 99% sequence identity to SEQ ID NO:4.

Certain embodiments of a kit also comprise instructions for use of a recombinant DNA construct. Such instructions can included directions as to the amount or concentration of the recombinant construct provided. Such instructions may be provided in the kit in either printed or electronic form. Alternatively, the instructions can be provided by way of a link or internet address that provides access to instructions located on an intranet or extranet site, or the like. The internet site can be either publicly available or secure. If the construct is provided dried, the instructions may teach how to reconstitute the nucleic acid construct into solution. The instructions may further teach how to introduce an isolated nucleic acid construct into a cell. The kit may also teach how to introduce an enzyme into a cell. The instructions may indicate how to culture various cell types under conditions amenable for transposition experiments. In certain applications, insertion of an exogenous DNA insert into a host cell genome via transposition is meant to alter the developmental state of the cell. For example, to drive an undifferentiated cell towards a differentiated phenotype, or to induce a differentiated cell to revert to exhibiting characteristics of undifferentiated or stem cells. For such applications, the instructions may instruct how to culture cells under conditions that allow for maintenance or differentiation.

IV. Method for Obtaining a Cell with a Genome Comprising a Reversibly Integrated Exogenous DNA Insert A major advantage of the PiggyBac transposon is that the exogenous DNA insertion sequence carried by the transposon is reversibly integrated into a host cell's genome. Thus, an exogenous DNA insertion sequence can be subsequently removed, such as by the reintroduction of the transposase activity. To take advantage of this desirable attribute, one must first obtain a cell comprising a reversibly integrated exogenous DNA insertion sequence. Certain embodiments of the present invention provide for obtaining a cell with a genome comprising a reversibly integrated exogenous DNA insertion sequence.

Methods of obtaining a cell with a genome comprising a reversibly integrated exogenous DNA insertion sequence can comprise the step of introducing an enhanced PiggyBac transposon into a cell in the presence of a PiggyBac transposase. In this context, "introducing" refers to any method whereby a nucleic acid is transferred into the cell. In certain embodiments, a cell can be transfected with a recombinant DNA construct comprising an enhanced PiggyBac transposon and a sequence encoding a PiggyBac transposase. In certain embodiments, the enhanced PiggyBac transposon and the PiggyBac transposase are on separate recombinant DNA constructs, for example a donor plasmid comprising an enhanced PiggyBac transposon and a helper plasmid comprising a sequence encoding a PiggyBac transposase wherein the donor and helper plasmid are co-introduced. Recombinant nucleic acid constructs can be introduced into a cell through a variety of standard methods including, but not limited to, chemical transfection, liposome-mediated transfections, microprojectile-mediated delivery, viral mediated delivery, electroporation, and nucleofection. Introduction of exogenous DNA into stem cells by a variety of methods has been disclosed (Kobayashi, N.; (2005) Birth Defects Res C Embryo Today 75(1): 10-8). Introduction of exogenous DNA into stem cells by nucleofection has been disclosed (Lakshmipathy, U., (2007) Methods Mol. Biol. 407: 115-26). The PiggyBac transposase can also be provided by providing the cell with the transposase enzyme. Delivery of protein can be achieved by any suitable method, including but not limited to, microinjection of transposase into the cell. In certain embodiments, a cell may previously express or contain a PiggyBac transposase activity, and an enhanced PiggyBac transposon is subsequently introduced into the cell.

Transposition efficiency can also be improved by optimizing a variety of DNA introduction parameters. One introduction parameter that can be optimized is the ratio of total introduced DNA to cell number. In certain embodiments where nucleofection is used to introduce the DNA into the cell, a ratio of about 1 to about 10 micrograms of transfected DNA per $1.5 \times 10^5$ cells can provide for optimal transposition efficiency. In certain embodiments where nucleofection is used to introduce the DNA into the cell, a ratio of about 5.5 to about 6.5 micrograms of transfected DNA per $1.5 \times 10^5$ cells can provide for optimal transposition efficiency. In certain embodiments where nucleofection is used to introduce the DNA into the cell, a ratio of about 6 micrograms of transfected DNA per $1.5 \times 10^5$ cells can provide for optimal transposition efficiency.

Another DNA introduction parameter that can be optimized is a ratio of the nucleic acid encoding the transposase to the ratio of the nucleic acid containing the transposon that are introduced into the cell. In certain embodiments where nucleofection is used to introduce the DNA into the cell, a transposase/transposon ratio of about 1 part transposase (by mass) to about 1.8 to about 2.2 parts transposon (by mass) can provide for optimal transposition efficiency. In certain embodiments where nucleofection is used to introduce the DNA into the cell, a transposase/transposon ratio of about 1 part transposase (by mass) to about 2 parts transposon (by mass) can provide for optimal transposition efficiency.

Another DNA introduction parameter that can be optimized is a type or composition of a solution used in the DNA introduction process. When nucleofection is used to introduce the DNA into the cell, a nucleofection solution V or nucleofection solution L (both obtainable from Amaxa, Gaithersburg, Md., USA) can be used. In certain embodiments where nucleofection is used to introduce the DNA into the cell, a nucleofection solution V (Amaxa, Gaithersburg, Md., USA) is preferred.

Combinations of any of the aforementioned optimized conditions for DNA introduction are also provided herein. In certain embodiments where nucleofection is used to introduce the DNA into the cell, a ratio of about 6 micrograms of transfected DNA per $1.5 \times 10^5$ cells, a transposase/transposon ratio of about 1 part transposase (by mass) to about 2 parts transposon (by mass), and a nucleofection solution V (Amaxa, Gaithersburg, Md., USA) can provide for optimal transposition efficiency.

Expression of an encoded transposase within the cell can be driven by an operably linked promoter that is active in the cell. In certain embodiments, this promoter can be a constitutive promoter. Useful constitutive promoters include, but are not limited to, viral promoters, cellular promoters and combinations thereof. In certain embodiments, a transposase coding region is operably linked to a CAG promoter that is a composite promoter comprising CMV and chicken beta-actin promoter elements (Niwa H. et al. 1991.-Gene 108(2):193-9). Transposase sources comprising a CAG promoter that is operably linked to a codon-humanized gene encoding a PiggyBac transposase are provided herein.

Expression of transposase within the cell can also be controlled or regulated such that it occurs for desired intervals of time. Such control or regulation can be achieved by operable linkage of the transposase encoding sequence to a regulatable promoter. Regulatable promoters useful for the controlled expression of transposase include, but are not limited to, promoters whose activity are regulated by steroidal compounds, doxycycline or other tetracyclin analogs, and the like.

An enhanced PiggyBac transposon can comprise an operably linked enhanced PiggyBac transposon 5'-terminal repeat sequence such as previously described, an operably linked exogenous DNA insertion sequence, and an operably linked PiggyBac transposon 3'-terminal repeat sequence. In certain embodiments, the enhanced PiggyBac transposon 5'-terminal repeat sequence can comprise SEQ ID NO:1 or functional variants thereof as described previously herein. The operably linked exogenous DNA insertion sequence can comprise numerous sequences, combinations of sequences, gene expression cassettes, and the like as described previously. Because of the enhancements made to the PiggyBac transposon and/or enhanced expression of the PiggyBac transposase, the exogenous DNA insertion sequence can be greater than 14.4 kB in length. In certain embodiments, the exogenous DNA insertion sequence is up to about 18 kB in length. In certain embodiments, the exogenous DNA insertion sequence can be between 14.4 kB and about 18 kB in length. In certain embodiments, the PiggyBac transposase is encoded by a codon-humanized nucleic acid sequence comprising a plurality of codons encoding the transposase that are more common to humans than to insects, such as previously described.

A next step in obtaining a cell with a genome comprising a reversibly integrated exogenous DNA insert is isolating a cell wherein an enhanced PiggyBac transposon has integrated into a genomic sequence of the cell. There are a variety of methods known in the art by which cells comprising an exogenous DNA insertion sequence in their genome can be isolated. For example, a cell comprising an exogenous DNA insert can express a visible marker, such as a fluorescent protein or other reporter protein, encoded by the sequence of the insert that aids in the identification and isolation of a cell or cells comprising the exogenous DNA insert. A cell comprising an exogenous DNA insertion sequence can also express a selectable marker from the insert. Survival of the cell under certain conditions, for example exposure to a cytotoxic substance or the lack of a nutrient or substrate ordinarily required for survival, is dependent on expression or lack of expression of a selectable marker. Thus, survival or lack of survival of cells under such conditions allows for identification and isolation cells or colonies of cells comprising a reversibly integrated exogenous DNA insertion sequence. Cells comprising a reversibly integrated exogenous DNA insertion sequence can also be isolated by examining the nucleic acid sequence of the cell's genome, such as by Southern Blotting or PCR analysis, to assay for the presence of the exogenous DNA insertion sequence. Cells from colonies that test positive for the exogenous DNA insertion sequence can be isolated. In some cases, the sequences expressed by an exogenous DNA insertion sequence may produce a morphological change to the cell, such as when such expressed sequences alters the development mental fate of the cell. Such cells can be selected based on their morphology and/or expression of one or more endogenous gene products induced by the transposon insert to obtain a cell comprising a reversibly integrated exogenous DNA insert.

V. Method for Obtaining a Cell that has Undergone a Reversible Genetic Modification The ability to transfer exogenous sequences into the genome of a cell, and then to remove those sequences provides many advantages over non-reversible gene transfer. Such an ability is especially desirable in cells intended for therapeutic use. Preferably, the removal of exogenous sequences is fully-reversible, meaning that the genome of the host cell at the site of insertion reverts back to a sequence that is indistinguishable from the pre-insertion sequence at that site. Enhanced PiggyBac transposons provided herein can permit fully-reversible transposition of an exogenous DNA insertion sequence Certain embodiments of the present invention thus provide for obtaining a cell that has undergone a reversible genetic modification.

Methods of obtaining a cell that has undergone a reversible genetic modification can first comprise providing a cell with a genome comprising a reversibly integrated PiggyBac transposon containing an operably linked exogenous DNA insert with a PiggyBac transposase and a recipient nucleic acid molecule. In certain embodiments, a cell comprising a reversibly integrated PiggyBac transposon can be obtained by using any of the previously described compositions and/or methods previously described. A cell comprising a reversibly integrated PiggyBac transposon is provided with a PiggyBac transposase to mediate remobilization and excision of the exogenous DNA insertion sequence. For example, the PiggyBac transposase may be provided by introducing a recombinant DNA construct into the cell that comprises a sequence encoding a PiggyBac transposase. The sequence encoding a PiggyBac transposase can be a wild-type sequence or an codon-humanized sequence as previously described herein. The PiggyBac transposase may also be provided by providing the PiggyBac transposase enzyme, such as by micro-injection into the cell.

A recipient nucleic acid molecule is provided along with the PiggyBac transposase activity. In the presence of transposase and a recipient nucleic acid molecule, a reversibly integrated PiggyBac transposon containing an operably linked exogenous DNA insertion sequence can be reversibly excised from its integration site in a host cell genome and transferred to a site in the recipient DNA molecule. Transfer to the site in the recipient DNA molecule can thus reduce the frequency of reintegrating of the excised transposon into another genomic location. After providing for transfer of a PiggyBac transposon exogenous DNA insert to a recipient nucleic acid molecule, the recipient nucleic acid molecule containing the reintegrated transposon can be removed or lost. Removal or loss of recipient nucleic acid molecules can be achieved by use of recipient nucleic acid molecules that are deficient in or lack host cell origins of replication. In certain embodiments, a recipient nucleic acid molecule can comprise a plasmid comprising one or more bacterial origin(s) of replication but lacking origins of replication or other sequences that provide for maintenance in the eukaryotic host cell. Recipient nucleic acid molecules that are deficient in or lack host cell origins of replication and contain the reintegrated transposon are lost from daughter cells in the absence of any selection for the recipient nucleic acid molecule. In certain embodiments, either the recipient nucleic acid molecule or the reintegrated transposon can comprise a nucleic acid sequence that permits removal of the sequence by a counter-selection. Genes permitting counter selection include, but are not limited to, a herpes simplex virus type 1 (HSV-1) thymidine kinase (TK) gene which can be counter selected by exposure of cells to counter selective agents including, but not limited to, acyclovir, trifluorothymidine and ganciclovir (Brisebois, J J; et al. (1993) Mutat. Res. 287: 191-205). Genes with both selectable and counter-selectable properties (a dual selectable/counter-selectable marker) can also be operably linked to the transposon. Such dual selectable/counter-selectable marker genes would thus provide for selection of cells comprising a reversibly integrated exogenous DNA insert containing a selectable marker. Dual selectable/counter-selectable marker genes also provide for counter selection of cells that have undergone a reversible genetic modification (i.e. cells where the reversibly integrated transposon has been excised and been removed). Dual selectable/counter-selectable marker genes include, but are not limited to, a TKNeo gene encoding a fusion protein comprising both HSV-TK and neomycin phosphotransferase (Neo) functional domains (Schwartz, F., et al. (1991) Proc. Natl. Acad. Sci. U.S.A. 88: 10416-10420). In other embodiments, both selectable and counter selectable marker genes can be provided in the transposon as separate transcription units and can comprise separate promoters. In still other embodiments, a transposon can contain both selectable and counter selectable marker genes that are operably linked within a single transcription unit where a single promoter drives expression of both genes and the promoter-distal or 3' most gene in the transcription unit is operably linked to an IRES.

The cell is cultured under conditions that allow for transposition of the PiggyBac transposon exogenous DNA insertion sequence to the recipient nucleic acid molecule and for subsequent removal or loss of said recipient nucleic acid molecule. Thereafter, a cell is isolated that no longer contains the exogenous DNA insertion sequence in its genome, and hence has undergone a reversible genetic modification. In certain embodiments, not only is the exogenous DNA insertion sequence removed from the genome, but the transposition of the insertion sequence to the recipient nucleic acid molecule returns the sequence of the genome at the original site of transposon insertion to its exact pre-insertion sequence. As previously described, there are a variety of methods of determining whether a cell contains an exogenous DNA insertion sequence. In particular, to isolate a cell that has undergone a reversible genetic modification, one may select cells that lack a marker or trait introduced by genetic modification from the cells originally obtained with a genome comprising a reversible genetic modification. In some cases however, it may be desirable or required that the trait introduced, such an acquired developmental fate, persist despite the removal of the reversible genetic modification. In such cases, means other than selecting for those particular traits should be relied on. Where reversible removal of the exogenous DNA insertion without any permanent alteration of the host genome is desired or required, verification may be achieved by post-excision examination of the host genome. Such examination can be achieved by direct or indirect sequencing of the insertion site, PCR analysis, DNA blot analysis, and the like.

To increase the probability that the PiggyBac transposon exogenous DNA insertion sequence is transferred to the recipient nucleic acid molecule, the molecule providing the PiggyBac transposase activity and the recipient nucleic acid molecule can be designed to increase their affinity for each other. One of skill in the art will recognize that there are numerous DNA binding proteins that have a high affinity for certain nucleic acid sequences. Many DNA binding domains have been identified that comprise distinct regions of a protein comprising a specific amino acid sequence responsible for recognition and association with a specific nucleic acid sequence, referred to herein as a binding site sequence. Certain embodiments of the present invention provide for a PiggyBac transposase that is operably linked to a DNA binding domain and a recipient nucleic acid molecule comprising one or more binding site sequences recognized by the DNA binding domain. It is contemplated that any sequence encoding a DNA binding domain and its corresponding nucleic acid binding site sequence may be useful. Non-limiting examples of different classes of DNA binding domains that can be operably linked to a PiggyBac transposase include the helix-turn-helix domain, the Zn-finger domain, the leucine zipper domain, and the helix-loop-helix domain. Further non-limiting examples of specific DNA binding domains include the Gal4 DNA binding domain, the LexA DNA binding domain, and the Zif268 DNA binding domain. One of skill in the art will recognize that the use of a flexible linker sequence linking the DNA binding domain to the PiggyBac transposase may be desirable. It may also be desirable to incorporate one or more nuclear localization signals into the transposase molecule to target its activity to the nucleus of the cell. The recipient nucleic acid molecule comprises one or more DNA binding site sequences corresponding to the DNA binding domain linked to the PiggyBac tranposase. For example, when the DNA binding domain used is a Gal4 DNA biding domain, the recipient nucleic acid molecule comprises one or more Gal4 UAS binding site sequences. Increasing the number of binding site sequences can increase the affinity of interaction between the recipient nucleic acid molecule, and thus increase the probability that the transposon insertion sequence will transfer to the recipient nucleic acid molecule. Therefore, in certain embodiments, numerous, for example six or more, or twelve or more, binding site sequences are incorporated into the recipient nucleic acid molecule.

VI. Embryonic Stem Cell (ESC) Differentiation

In certain embodiments, the reversibly integrated PiggyBac transposon exogenous DNA insertion sequence comprises one or more sequences encoding one or more gene products that alter the developmental fate of a pluripotent stem cell. For example, expression of the transcription factor Oct4 is known to be involved in maintaining embryonic stem cells in an undifferentiated state. Disruption of Oct4 expression can result in stem cell differentiation. Certain embodiments of the present invention provide for an exogenous DNA insertion sequence encoding a gene product that inhibits Oct4 expression. Inhibitory gene products include, but are not limited to, an antisense nucleic acid sequence or an inhibitory RNA sequence such as an shRNA, siRNA, and the like.

Differentiation of a pluripotent stem cell may be further guided to drive differentiation of the cell towards a desired cell fate. In certain embodiments, the reversibly integrated PiggyBac transposon exogenous DNA insertion sequence comprises one or more sequences encoding one or more gene products that drive differentiation of a pluripotent cell towards a desired cell fate. For example, in certain embodiments, it is desirable to obtain a cell that is of a neural cell type. It is known in the art that expression of certain proteins, such as the Sox1 protein, can drive a cell towards a neural cell fate. Thus, in a first illustrative example, one of the gene products encoded by the exogenous DNA insertion sequence comprises Sox1. Inhibition of expression of certain genes, such as Oct4, Gata6, Brachyury, and Cdx2 is also known to drive a cell towards a neural cell fate. Thus, in another illustrative example, one or more of the gene products encoded by the exogenous DNA insertion sequence comprise inhibitory gene products that inhibit expression of at least one or all of an Oct4, a Gata6, a Brachyury, or a Cdx2 gene. Inhibitory gene products include, but are not limited to, an antisense nucleic acid sequence or an inhibitory RNA sequence such as an shRNA, siRNA, and the like. In certain embodiments, the one or more gene products encoded by the exogenous DNA insertion sequence comprise a combination of both proteins and inhibitory gene products, such as those previously described. In certain cases, it may be advantageous to place control of the expression of such gene products under the control of an inducible promoter or regulatory system so that expression of the gene products is inducible when desired.

Piggybac transposons comprising operably linked genes that drive stem cell differentiation can be introduced into stem cells using aforementioned compositions and methods provided herein to obtain a cell where the genes that provide for stem cell differentiation are reversibly integrated. Reversibly integrated stem cell differentiation genes that have exerted a desired effect (i.e. differentiation of the stem cell to a desired differentiated cell type) can then be excised by using aforementioned methods and compositions that provide for a cell that has undergone a reversible genetic modification. In this case, the cell that has undergone the reversible genetic modification will be differentiated and the sequence of the insertion site in the cell's genome is restored to the sequence present at that site in the cell's genome prior to insertion of the transposon.

VII. Method for Obtaining an Induced Pluripotent Stem Cell

In certain embodiments of the present invention, the method described previously for obtaining a cell that has undergone a reversible genetic modification can be used to obtain an induced pluripotent stem cell. Such methods can first comprise obtaining a cell comprising a reversible genetic modification as previously described. The reversible genetic modification comprises an exogenous DNA insertion sequence that provides one or more gene products that induce a cell to become a pluripotent stem cell. The cell is cultured for a period of time that is sufficient for the one or more gene products of the exogenous DNA insertion sequence to convert the cell to a pluripotent stem cell. The exogenous DNA insertion sequence is then removed from the cells genome, such as by the introduction of a PiggyBac transposase and a recipient nucleic acid molecule as previously described. A pluripotent stem cell can then be isolated wherein the reversible genetic modification has been removed from the cell. It is contemplated that such pluripotent stem cell can be a vertebrate or invertebrate cell. In certain embodiments, the pluripotent stem cell is a mammalian sell, such as but not limited to, a human cell, a mouse cell, or a rat cell.

The disclosed embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

All reagents and chemicals are either commercially available or can be prepared by standard procedures found in the literature or are known to those of skill in the arts of cell and molecular biology, genetics and molecular genetics, organic chemistry, biochemistry, and the like.

Example 1

Methods

DNA Constructs.

The original PiggyBac transposase DNA was obtained from Dr. M. Fraser (University of Notre Dame, Ind., USA). The ePiggyBac transposase cDNA was custom synthesized. To generate helper plasmids, transposase cDNAs were cloned in PBLUESCRIPT™ (Stratagene, La Jolla, Calif., USA) downstream of a human phosphoglycerate kinase (PGK) or CAG promoter and upstream of an SV40 polyadenylation signal sequence. Minimal 313 bp 5'TR and 235 bp 3'TR were custom synthesized and cloned respectively upstream and downstream of expression cassettes containing the PGK promoter driving EGFP (BD Biosciences, San Jose, Calif., USA) or tagRFP (Evrogen, Moscow, Russia). The plasmid rescue system also included an ampicillin resistance cassette and an origin of replication from in PBLUESCRIPT™ cloned between the 5'- and 3'-terminal repeats. To improve gene transfer efficiency, mutations in terminal repeats were introduced using the GeneMorph II random PCR mutagenesis system (Stratagene, La Jolla, Calif., USA). To generate the Oct4-EGFP transposon, the human Oct4 promoter (Gerrard, L., et al. (2005) Stem Cells 23: 124-133) was cloned upstream of EGFP. The 250 bp chicken β-globin HS4 core insulator (Recillas-Targa, F., et al. (2002) Proc. Natl. Acad. Sci. USA 99: 6883-6888) was custom-synthesized and inserted between the hOct4-EGFP reporter and a neomycin/kanamycin cassette subcloned from pEGFP-N1 (BD Biosciences, San Jose, Calif., USA). Finally, the hOct4-EGFP reporter, HS4 insulator and selection cassette were flanked by 5' and 3'TR. The helper plasmid for transgene removal was generated by cloning the Gal4 DNA binding domain between the PGK promoter and the transposase cDNA of the ePiggyBac helper plasmid to create a Gal4-ePiggyBac fusion. Two consensus nuclear localization signals (MPKKKRKVDP-KKKRKVD) (SEQ ID NO: 41) were incorporated at the N-terminus of the Gal4 DNA binding domain and a flexible linker (GGSGGSGSS) (SEQ ID NO: 42) was incorporated at its C-terminus. The recipient plasmid was generated by adding 14 UAS sequences to the pLD53 backbone (Metcalf, W. W., et al. (1996) Plasmid 35: 1-13). This plasmid contains an R6Kγ origin of replication which is inactive unless the π protein is provided by the bacterial host. It was therefore maintained in pir-2 *E. coli* (Invitrogen Carlsbad, Calif., USA). For nucleofection, all plasmids were prepared using a QIAPREP™ Spin Miniprep kit (Qiagen, Valencia, Calif., USA) and purified by phenol:chloroform extraction and ethanol precipitation. For RNA interference, shRNA were designed as described (Silva, J. M., et al. (2005) Nat. Genet. 37: 1281-1288). The shRNAs used in this study are summarized in Table 1.

Table 1.

Sequence of shRNAs used in Example 9. All shRNAs were modeled after human miR-30. (shEGFP, SEQ ID NO:8; shOCT4, SEQ ID NO:9; shGata6, SEQ ID NO:10; shBrachyury, SEQ ID NO:11; shCdx2, SEQ ID NO:12)

```
shEGFP
TGCTGTTGACAGTGAGCGAAAGAACGGCATCAAGGTGAACTAGTGAAGCCACAGATGTAGTTCACCTTGATGCCGTTCTTCTGCCTACTGCCTCGGA shOCT4
TGCTGTTGACAGTGAGCGCGGTCCGAGTGTGGTTCTGTAATAGTGAAGCCACAGATGTATTACAGAACCACACTCGGACCATGCCTACTGCCTCGGA shGata6
TGCTGTTGACAGTGAGCGATGGGAGGACTTGCTGCTGTTCTAGTGAAGCCACAGATGTAGAACAGCAGCAAGTCCTCCCAGTGCCTACTGCCTCGGA shBrachyury
TGCTGTTGACAGTGAGCGAACAACTCACCTGCATGTTTATTAGTGAAGCCACAGATGTAATAAACATGCAGGTGAGTTGTCTGCCTACTGCCTCGGA shCdx2
TGCTGTTGACAGTGAGCGATTTCAGAACCGCAGAGCAAAGTAGTGAAGCCACAGATGTACTTTGCTCTGCGGTTCTGAAACTGCCTACTGCCTCGGA
``` hESC Lines and Culture Conditions.

hESC lines RUES1 (James, D., et al. (2006) Dev. Biol. 295: 90-102), RUES2, H1 (Thomson, J. A., et al. (1998) Science 282: 1145-1147), HUES10 (Cowan, C. A., et al. (2004) N. Engl. J. Med. 350: 1353-1356), and BGN1 (Mitalipova, M., et al. (2003) Stem Cells 21: 521-526), as well as *Macacca fascicularis, M. nemestrina* (both from the Reproductive Biology Core, Washington National Primate Research Center) and *M. mulatta* line R366.4 (Thompson, J. A., et al. (1995) Proc. Natl. Acad. Sci. USA 92: 7844-7848) ESCs were grown on mitotically inactivated MEF feeders (strain CF-1; Chemicon, Billerica, Mass., USA) in HUESM (DMEM supplemented with 20% KSR, 100 µM non-essential amino acids, 2 mM GlutaMAX, 100 µM β-mercaptoethanol, 100 U/ml penicillin, 100 µg/ml streptomycin and 1× B27 supplement without Vitamin A; all from Invitrogen, Carlsbad, Calif., USA) supplemented with 20 ng/ml bFGF. All hESC lines were transferred to feeder-free conditions on Matrigel-coated dishes and cultured in conditioned medium (CM) for at least one passage prior to gene delivery. For the preparation of CM, mitotically inactivated MEFs were seeded at a density of $4.10^6$ cell per 100 mm dish and incubated in HUESM supplemented with 20 ng/ml bFGF for 24 h. CM was then collected, supplemented with 20 ng/ml bFGF and used to feed human and macacca ESCs. For expansion, hESC were enzymatically passaged using 1 mg/ml dispase treatment (James, D., et al. (2006) Dev. Biol. 295: 90-102). Embryoid bodies were generated by incubation of hESC cultures in dispase until colonies detached from the substrate. Individual aggregates were then transferred to low attachment 96-well plates (Evergreen Scientific, Los Angeles, Calif., USA) and grown in HUESM for at least 2 weeks prior to GFP or immunofluorescence imaging. To generate teratomas, $1-2\times10^6$ hESCs were injected into the rear leg muscle or subcutaneously into SCID/Beige mice. Teratomas were allowed to develop for 6-8 weeks, excised, fixed in neutral buffered formalin and analyzed histologically by trained pathologists. hESC lines were karyotyped by standard G-banding.

Gene Transfer.

Prior to dissociation and nucleofection, hESC and *Maccaca* ESC cultures or dissociated neural spheres were treated for 1 h with 10 µM ROCK inhibitor Y-27632 which strongly diminishes dissociation-induced apoptosis and increases cloning efficiency (Watanabe, K., et al. (2007) Nat. Biotechnol. 25: 681-686). ESCs were then dissociated in 0.25% (wt/vol) trypsin-EDTA at 37° C. for 5 min, washed in CM with ROCK inhibitor and resuspended in nucleofection solution V or L (Amaxa, Gaithersburg, Mass., USA). Helper and transposon plasmids were added to the cell suspension and nucleofection was performed using program setting B-016 as described (Siemen, H., et al. (2005) Stem Cells Dev. 14: 378-383). ESCs were then plated in CM supplemented with 10 µM ROCK inhibitor at densities of $2.10^5$ cells per 6 cm dish for the selection of clonal cell line hOct4-EGFP or $2.10^3$ cells per 6 cm dish for fluorescent colony counts. Culture medium was changed to CM without ROCK inhibitor 20-24 h after nucleofection and colonies were allowed to form for 7 days before numbers of fluorescent colonies were evaluated. EGFP-positive colony count based on microscopic observation was preferred over single cell counts by flow cytometry. This constitutes a more stringent and more functionally relevant way to assess the efficiency of a gene delivery system because transgene silencing is frequent in hESCs and only a fraction of single transgenic cells gives rise to an EGFP-labeled marked cell line that can be used for further applications (Brawn, S. R., et al. (2008) Nat. Methods 5: 389-392). In experiments where selection was needed, exposure to neomycin (100 µg/ml) or ganciclovir (1 µM) was initiated three days after nucleofection and maintained until large resistant colonies became visible. Media were refreshed daily.

Plasmid Rescue and hESC Genotyping.

Genomic DNA isolated from transgenic hESC clones was digested with restriction enzymes BamHI, BglII and NotI. DNA was self-ligated at low concentration with T4 DNA ligase overnight at 16° C., precipitated with 100% isopropanol and washed with 70% ethanol before transformation in DH10B *Escherichia coli* and selection on ampicillin. For transgene removal experiments, undigested DNA was extracted from hESC cultures and used for *E. coli* transformations. Bacterial transformants were then selected on both ampicillin and kanamycin. Plasmid DNA from resistant *E. coli* clones was sequenced using primers that read through the 5'TR of the PiggyBac transposon. hESCs were genotyped before and after transposon removal using the following primers: 3'TR-F 5'-CTTAAGGAATTCGATAAAAG-3' (SEQ ID NO:35) and 3'TR-R 5'-GATACATTGAT-GAGTTTGG-3' (SEQ ID NO:36) which read through the 3'TR of the PiggyBac transposon, 18-F 5'-CGTGCTTACAG-GCATTGAGC-3' (SEQ ID NO:37) and 18-R 5'-CTGGAAC-CTCGACTTCTTGG-3' (SEQ ID NO:38) which flank the integration site of the Neo-TK-RFP transposon (FIG. 3A) on chromosome 18.

mRNA Quantifications.

RNA was isolated using RNA-BEE™ (Tel-Test Inc. Friendswood, Tex., USA) and first-strand cDNA was generated using a SUPERSCRIPT III™ cDNA First Strand Synthesis kit (Invitrogen, Carlsbad, Calif., USA). Quantitative Real-time PCR reactions were performed using a LIGHTCY-CLER™ 480 SYBR Green I Master Kit (Roche, Basel, Switzerland). Primers used to measure mRNA levels are summarized in Table 2.

Table 2.

Sequences of quantitative RT-PCT primers referred to in Examples. (Oct2 Forward Primer, SEQ ID NO:13; Oct4 Reverse Primer, SEQ ID NO:14; Nanog Forward Primer, SEQ ID NO:15, Nanog Reverse Primer, SEQ ID NO:16, Sox2 Forward Primer, SEQ ID NO:17; Sox2 Reverse Primer, SEQ ID NO:18; Pax6 Forward Primer, SEQ ID NO:19; Pax6 Reverse Primer, SEQ ID NO:20; Sox1 Forward Primer, SEQ ID NO:21; Sox1 Reverse Primer, SEQ ID NO:22; NFH Forward Primer, SEQ ID NO:23; NFH Reverse Primer, SEQ ID NO:24; Chordin Forward Primer, SEQ ID NO:25; Chordin Reverse Primer, SEQ ID NO:26; Mix11 Forward Primer, SEQ ID NO:27; Mix11 Reverse Primer, SEQ ID NO:28; Sox17 Forward Primer, SEQ ID NO:29; Sox17 Reverse Primer, SEQ ID NO:30; hCG beta Forward Primer, SEQ ID NO:31; hCG beta Reverse Primer, SEQ ID NO:32; GAPDH Forward Primer, SEQ ID NO:33; GAPDH Reverse Primer, SEQ ID NO:34).

|          | Forward primer                | Reverse primer               |
|----------|-------------------------------|------------------------------|
| Oct4     | CAAGCTCCTGAAGCAGAAGAGGAT      | CTCACTCGGTTCTCGATACTGGTT     |
| Nanog    | CCGGTCAAGAAACAGAAGACCAGA      | CCATTGCTATTCTTCGGCCAGTTG     |
| Sox2     | TCAGGAGTTGTCAAGGCAGAGAAG      | GCCGCCGCCGATGATTGTTATTAT     |
| Pax6     | TCACCATGGCAAATAACCTG          | CAGCATGCAGGAGTATGAGG         |
| Sox1     | GAGATTCATCTCAGGATTGAGATTCTA   | GGCCTACTGTAATCTTTTCTCCACT    |
| MFH      | TGAACACAGACGCTATGCGCTCAG      | CACCTTTATGTGAGTGGACACAGAG    |
| Chordin  | TGTGAGCGGGATGACTGTTCACT       | TGTCATGGGATTGCAGCATGGA       |
| Mix11    | GGTACCCCGACATCCACTT           | GCCTGTTCTGGAACCATACCT        |
| Sox17    | GGCGCAGCAGAATCCAGA            | CCACGACTTGCCCAGCAT           |
| hCG beta | ATCACCGTCAACACCACCATCTGTG     | AGAGTGCACATTGACAGCTGAG       |
| GAPDH    | AGTCCCTGCCACACTCAG            | CCTTGTCATGTACCATCAATAAAGTA   |

Immunohistochemical Assays and Confocal Imaging.

Undifferentiated hESCs or adherent embryoid bodies plated on MATRIGEL™-coated MatTek (Ashland, Mass., USA) coverslip dishes were fixed in 4% paraformaldehyde (PFA), washed in phosphate buffered saline solution and blocked in 0.1% triton X-100 and 3% donkey serum in PBS. Samples were exposed to primary antibodies in blocking solution overnight at 4° C., washed 3 times in PBS with 0.1% tween-20 at room temperature and exposed to Alexa-conjugated secondary antibodies (dilution 1:500). Primary antibodies included Oct3/4 (BD Transduction Labs, San Jose, Calif.), tagRFP (Evrogen, Moscow, Russia), GATA6, Nestin, Cytokeratin 18 and doublecortin (Santa Cruz, Santa Cruz, Calif., USA), Muscle MHC/MF20 (Developmental Studies Hybridoma Bank, University of Iowa, USA), Neurofilament Heavy Chain (SMI32, Sternberger, Baltimore, Md., USA), Map2 (Millipore, Billerica, Mass., USA) Nanog and Sox2 (R&D Systems, Minneapolis, Minn., USA). Alexa-conjugated secondary antibodies and SYTOXORANGE™ nuclear counterstain were purchased from Molecular Probes (Invitrogen, Carlsbad, Calif., USA). All imaging was performed on a Zeiss LSM 500 Pascal confocal microscope (Carl Zeiss, Inc., Thornwood, N.Y., USA).

Statistical Analysis.

The statistical significance (P values) in means of two-sample comparison was determined with Student's t-test. The statistical significance in mean values among multiple sample groups was examined with two-way ANOVA and Bonferroni's post-hoc test. Values shown in graphs represent the mean±s.d.

Example 2

Activity of ePiggyBac in hESC and Non-Human Primate ESC Lines

Figure 8:
FIG. 8: Standard G-banding reveals that upon transposition, XX hESC line RUES2 retains a normal karyotype.
Figure 9:
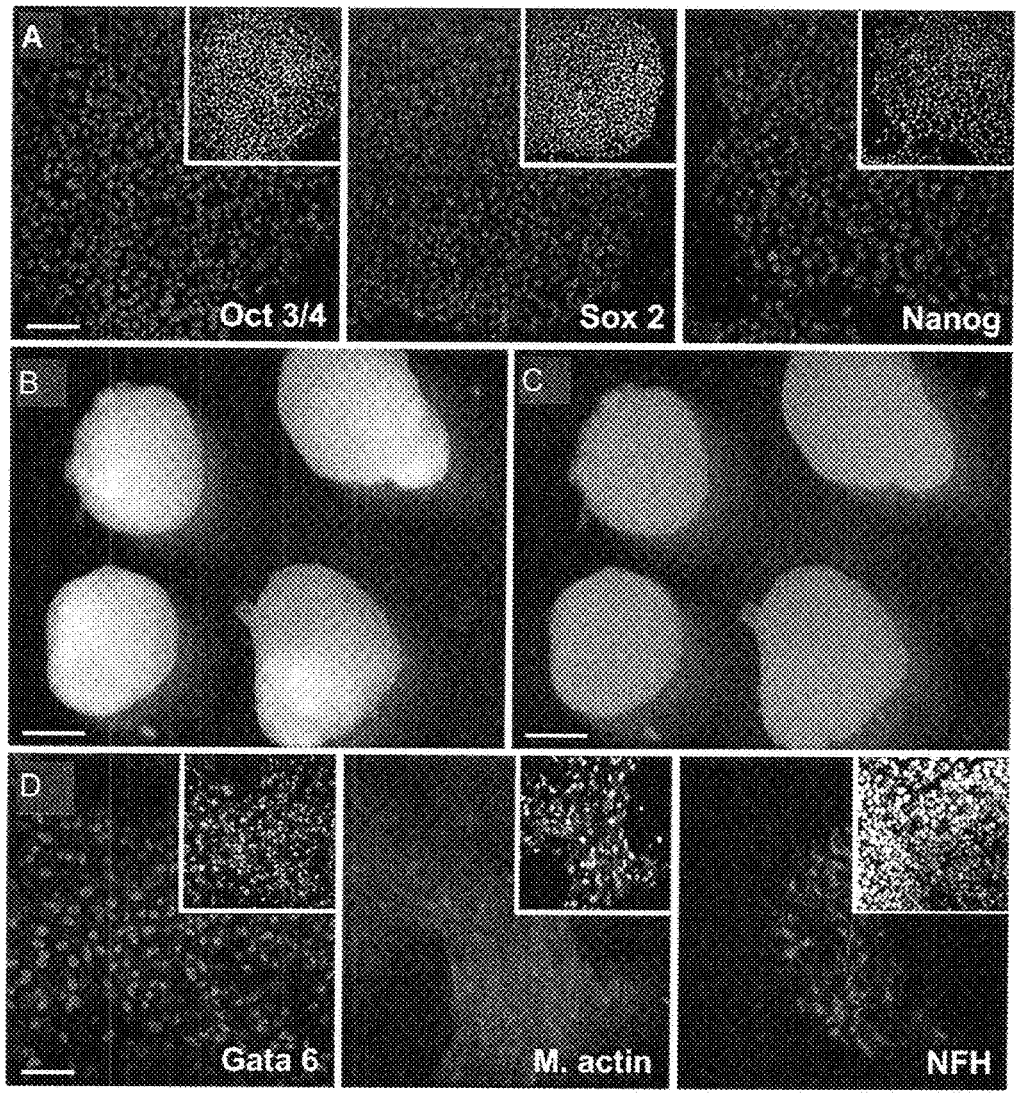
FIG. 9.
Figure 10:
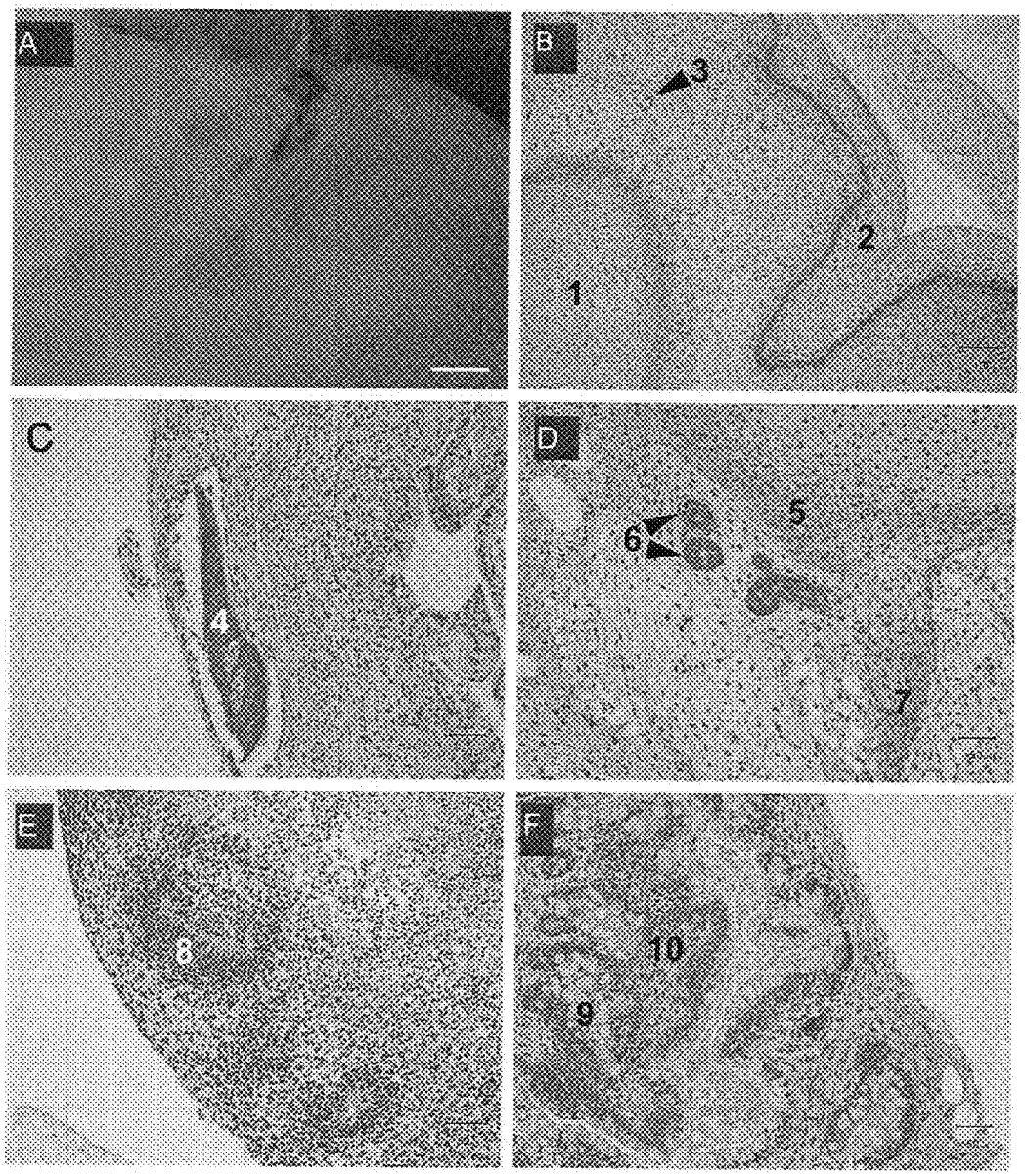
FIG. 10.

Gene delivery experiments were performed in hESC and non-human primate ESC lines. FIG. 1d demonstrates that ePiggyBac efficiently transferred EGFP- or RFP-expressing transgenes in different hESC lines. Importantly, ePiggyBac-mediated gene delivery does not alter the hESC karyotype (FIG. 8) or the ability of hESCs to express pluripotency markers, form embryoid bodies and differentiate into all three germ layers (FIG. 9 and FIG. 10). In addition, no silencing of fluorescent protein expression was observed after over 40 passages and gene transfer efficiency remained high in non-human primate ESCs (FIG. 1d) indicating that ePiggyBac can be used as a generic gene delivery system in primate ESCs.

Example 3 ePiggyBac can be Used to Deliver Large Inserts into the hESC Genome

One of the most important advantages of the use of the PiggyBac system over other gene delivery systems lies in the PiggyBac transposon's ability to carry large DNA inserts (Ding, S., et al. (2005) Cell 122: 473-483). To investigate ePiggyBac's ability to integrate large DNA constructs in the hESC genome, inserts of increasing size were added to the transposon (FIG. 1E). It was found that although transposition efficiency decreased significantly for inserts larger than 14 Kb, ePiggyBac could deliver inserts of up to 18 Kb in size to the hESC genome, which is larger than the insert size delivered by the original PiggyBac system (FIG. 1E), or the maximum 14.3 Kb insert size previously reported for mouse embryos (Ding, S., et al. (2005) Cell 122: 473-483).

Example 4 ePiggyBac can Deliver Large Inserts Containing Multiple Components Such as Expression Cassettes, Insulator Sequences and Plasmid Rescue Systems A 12 Kb transposable insert was created containing an origin of replication for plasmid rescue, a constitutively expressed neomycin-phosphotransferase cassette, and a reporter construct where EGFP expression is driven by the human Oct4 promoter (Gerrard, L., et al. (2005) Stem Cells 23: 124-133) (FIG. 1F). The insert included a chicken HS4 insulator (Recillas-Targa, F., et al. (2002) Proc. Natl. Acad. Sci. USA 99: 6883-6888) to prevent the constitutively expressed neomycin cassette from interfering with the hOct4-EGFP reporter, which should only label undifferentiated hESCs (Gerrard, L., et al. (2005) Stem Cells 23: 124-133). After gene delivery, 7 days of neomycin selection were sufficient to select EGFP-positive colonies that could be expanded to establish an hOct4-EGFP RUES2 cell line. To test the specificity of EGFP labeling, we compared levels of fluorescence in cells cultured in non-differentiating versus differentiating conditions (FIG. 1G). Live-cell imaging showed that EGFP-labeling is lost in cells maintained in differentiating conditions and in 18 days-old embryoid bodies. In addition, co-immunostaining showed that the decrease in EGFP expression is consistent with the decrease in endogenous Oct4 protein expression (FIG. 1H and FIG. 1I). These experiments indicate that ePiggyBac can integrate large multi-component inserts into the hESC genome without differentiating conditions altering their functionality.

Example 5

Optimization of Gene-Delivery Parameters

Figure 13:
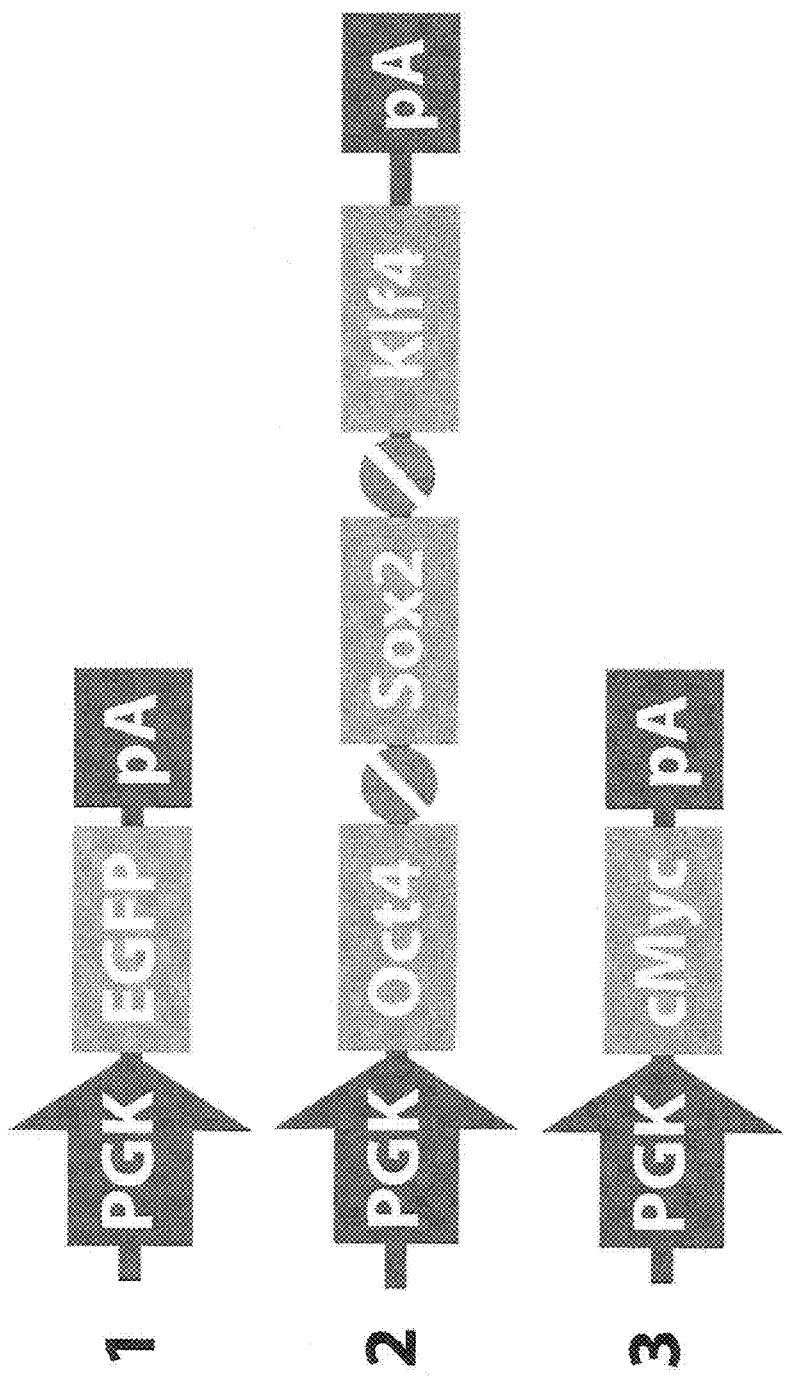
FIG. 13. Recombinant DNA constructs for experimental set 1.

Systematic alteration of gene-delivery parameters was conducted to define conditions that would further increase gene-delivery efficiency and complement our molecular modifications to the transposase and transposon. It was found that expressing the transposase from the CAG promoter, using 6 μg of DNA per $1.5 \cdot 10^5$ cells, a transposase/transposon ratio of 1:2 and transfection solution L instead of V (Siemen, H., et al. (2005) Stem Cells Dev. 14: 378-383) led to a dramatic increase in transgenesis efficiency. Using ePiggyBac under these conditions, we commonly obtain transgene expression in almost 90% of hES cell colonies (FIG. 13) which is higher than gene delivery efficiencies reported for viral vectors (Pfeifer, A., et al. (2002) Proc. Natl. Acad. Sci. USA 99: 2140-2145; Ben-Dor, I., et al. (2006) Mol. Ther. 14: 255-267).

Example 6 ePiggyBac Retains Basic PiggyBac Characteristics

To determine whether gene transfer was the result of a transposition event, sites of integration were isolated using a plasmid rescue strategy (FIG. 2A), sequenced and analyzed by BLAST search of the Ensembl database. Analysis of 62 ePiggyBac integration sites revealed no obvious consensus sequence other than the TTAA tetranucleotide sequence (FIG. 2B) required for PiggyBac transposition (Ding, S., et al. (2005) Cell 122: 473-483; Wilson, M. H., et al. (2007) Mol. Ther. 15: 139-145; Cadiñanos, J. and Bradley, A. (2007) Nucleic Acid Res. 35: e87; Li, X., et al. (2005) Insect Mol. Biol. 14: 17-30). A nucleotide frequency plot (FIG. 2C) also revealed a preference for AT reach regions around the core TTAA sequence. Sequence analyses showed that ePiggyBac integrations occurred in all chromosomes of the female hESC line RUES2 (FIG. 2D). Transgenic hESCs typically carried 1-12 copies of the transposon. Interestingly, 72% of integrations occurred within 10 Kb of a known transcription start site and 96% of integrations that took place downstream of the transcription start site occurred in introns (FIG. 2E) as described for the original PiggyBac transposable element (Ding, S., et al. (2005) Cell 122: 473-483; Wilson, M. H., et al. (2007) Mol. Ther. 15: 139-145). These data indicate that mutations introduced in the PiggyBac system, increased gene delivery efficiency without altering its basic properties.

Example 7 ePiggyBac-Mediated Transposition does not Alter hESC Fundamental Properties

To verify that ePiggyBac-mediated gene transfer did not alter basic hESC properties, a transgenic RUES2 line was tested for its ability to express pluripotency markers and differentiate into the three germ layers. Immunostaining experiments revealed that upon transposition, RUES2 still expressed pluripotency markers Oct3/4, Sox 2 and Nanog (FIG. 9A). This cell line also retained its ability to form embryoid bodies (FIG. 9B) which were fluorescent, indicating that transgene expression is not silenced upon differentiation (FIG. 9C). Finally, immunostaining showed that embryoid bodies contained representatives of all three germ layers (FIG. 9D). The ability to differentiate into all three germ layers was further confirmed in teratomas (FIG. 10) and standard G-banding indicated that transposition does not alter the hESC karyotype (FIG. 8). These experiments indicated that ePiggyBac-mediated gene transfer does not alter hESC fundamental properties.

Example 8 ePiggyBac Transgenes can be Removed from the Genome

In contrast to viral vectors and PhiC31 systems, transposons can be remobilized and moved from one locus to another by re-expression of the transposase (Wilson, M. H., et al. (2007) Mol. Ther. 15: 139-145; Elick, T. A., et al. (1996) Genetica 98: 33-41). Transposons are commonly transferred from a donor plasmid to a recipient plasmid or genomic DNA. Transfer of ePiggyBac transposons from the genome to a plasmid would enable reversions from a transgenic to a completely intact genome because PiggyBac does not leave any mutation upon excision. However, transposition from the genome to a recipient plasmid is an unlikely event because plasmids are million times smaller than the human genome and therefore, genomic DNA is a much more likely target for integration.

Figure 11:
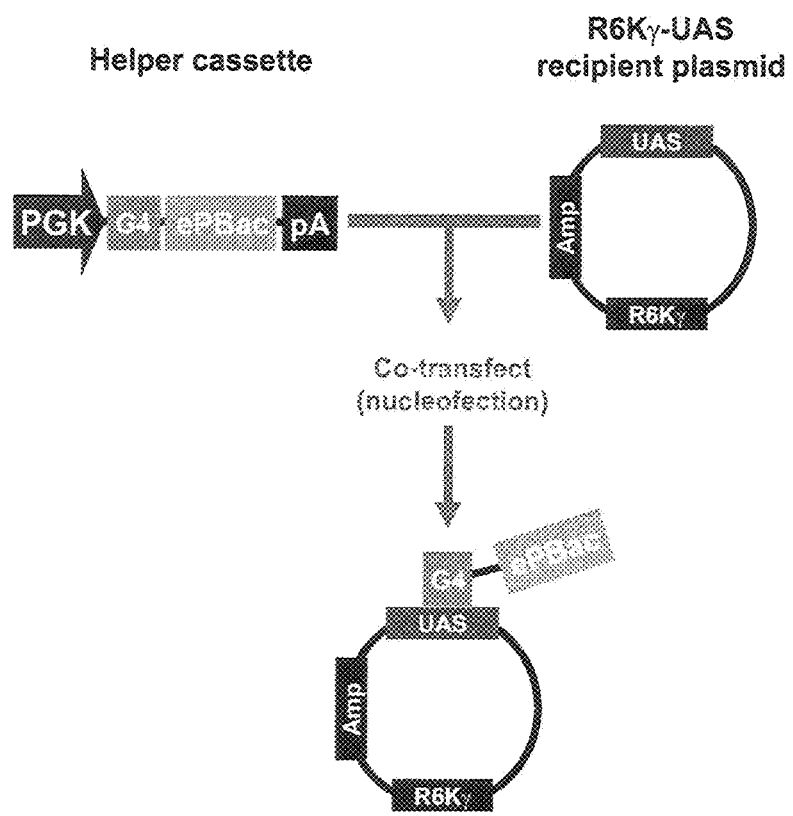
FIG. 11.

To increase the probability that ePiggyBac transposons excised from the genome are transferred to a plasmid rather than moved to another genomic location, a recipient plasmid was first engineered carrying 14 "upstream activating sequences" (UAS) (FIG. 11). Next, a helper plasmid was generated where the Gal4 DNA binding domain is fused to the N-terminus of ePiggyBac. Upon co-transfection of these two vectors, the Gal4-ePiggyBac chimeric protein binds to the UAS-carrying recipient plasmid with high affinity (FIG. 11). This interaction between the Gal4-ePiggyBac chimeric protein and the UAS-carrying recipient plasmid is expected to strongly increase chances that transposons are transferred to the recipient plasmid (Maragathavally, K. J., et al. (2006) FASEB J. 20: 1880-1882).

To test whether this strategy enables the removal of transposons from the hESC genome, we created a transgenic RUES2 cell line containing a single copy of an RFP-expressing transposon where neomycin-phosphotransferase and thymidine kinase cassettes are used for negative and positive selection respectively (FIG. 3A). This cell line was maintained under 200 µg/ml neomycin selection for 5 passages to eliminate non-transgenic cells. It is ganciclovir sensitive and exhibits uniform RFP expression (FIG. 3B).

Upon co-transfection of the Gal4-ePiggyBac helper and recipient plasmid, 6.48+/−1.04% colonies exhibited mosaic RFP expression (FIG. 3C) whereas mosaic RFP expression was not observed in non-transfected cultures (not shown). DNA extracted from these hESC was used to transform *E. coli* bacteria. Bacterial transformants were then selected for both ampicillin and kanamycin resistance conferred by the recipient plasmid and transposon respectively. Sequence analyses revealed that the transposable element originally carried by the transgenic hESC genome had been transferred to the recipient plasmid (FIG. 3D). In addition, presence of the typical TTAA tetranucleotide at the junction between transposon and plasmid sequences indicated that the transposon had been inserted in the recipient plasmid by ePiggyBac transposition.

Ganciclovir selection was used to recover RFP-negative hESC colonies. These colonies did not survive under neomycin selection (not shown), indicating that the cells had lost all three selectable markers: RFP, neomycin phosphotransferase and thymidine kinase. Importantly, un-transfected hESCs or controls where hESCs were transfected with either helper or recipient plasmid alone did not give rise to ganciclovir-resistant colonies (FIG. 3E). This result excludes the possibility that ganciclovir resistance, neomycin sensitivity and loss of RFP expression are due to silencing of selection cassettes on the transposon. Furthermore, PCR genotyping (FIG. 3F) indicated that ganciclovir-resistant/neomycin-sensitive/RFP negative colonies did not carry any transgene. Finally, sequence analyses revealed that the original transposon integration site was devoid of transgene or footprint mutation (FIG. 3G). These data indicate that ePiggyBac can both deliver large multicomponent transgenes to the hESC genome and remove them without leaving any mutation.

Figure 12:
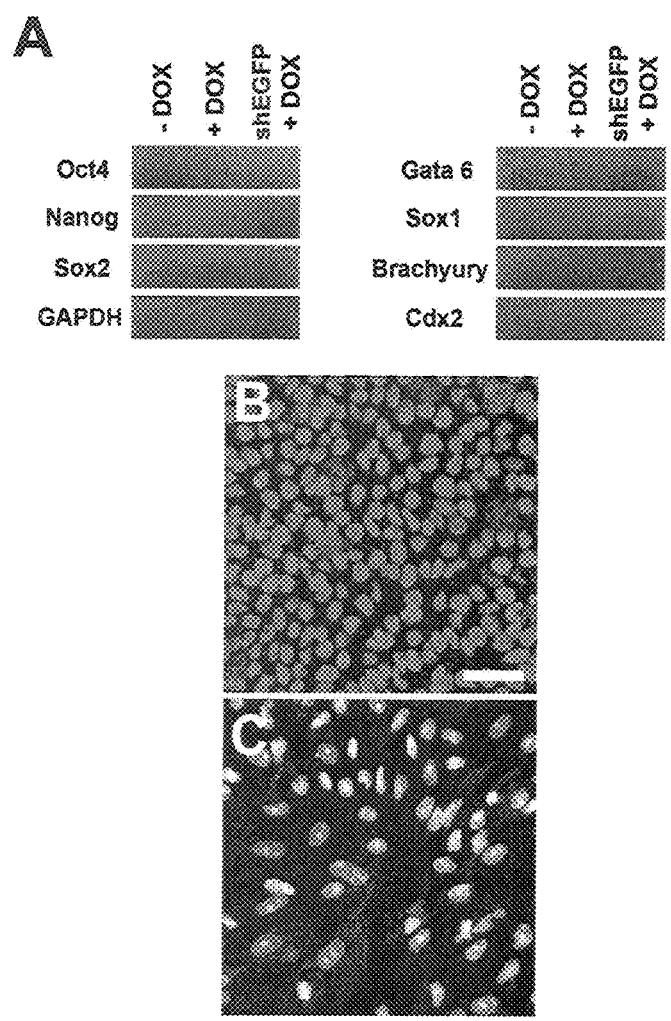
FIG. 12A.
FIG. 12B and FIG. 12C.

Example 9 ePiggyBac-Mediated Loss- and Gain-of-Function Directs hESC Differentiation Towards Specific Cell Types without Genome Alterations It was investigated whether the ability to deliver large multicomponent transgenes to hESC and remove them could be used to drive hESC differentiation toward a specific cell type. First, a transposable and inducible short hairpin RNA (shRNA)-expressing system was created in order to knockdown pluripotency gene expression. This transposon (FIG. 4A) expresses shRNAs modeled after human miR-30 (Silva, J. M., et al. (2005) Nat. Genet. 37: 1281-1288). Previous studies have shown that miR-30-based shRNAs inhibit gene expression more efficiently than simple stem-loop shRNAs and their expression can be driven by Pol II promoters. This enabled the use of the TetON system and control gene knockdown by addition of doxycycline to the cell culture medium. RUES2 cells were transfected with an shRNA vector targeting Oct4 and grown in the presence of Neomycin until 500-1000-cell colonies were obtained. Doxycycline was then added to the conditioned culture medium to induce anti-Oct4 shRNA expression. Quantitative RT-PCR analyses showed that four days after the addition of doxycycline, the expression of pluripotency markers Oct4, Sox2 and Nanog decreased whereas differentiation markers Gata6, Sox1, Brachyury and Cdx2 increased compared to samples grown in the absence of doxycycline or in cells expressing a control anti-EGFP shRNA (FIG. 4B and FIG. 12). Concomitantly, clear morphological differences appeared between cells grown in the absence of doxycycline, which formed tightly packed colonies (FIG. 4C) characteristic of undifferentiated hESCs, and cells expressing the anti-Oct4 shRNA, which exhibited a flattened morphology reminiscent of differentiated cells (FIG. 4D). These morphological changes were accompanied by a strong increase in immunoreactivity for the trophectoderm marker cytokeratin 18 in filamentous structures characteristic of epithelial cell types (FIG. 4E and FIG. 12). These results indicate that the ePiggyBac system can be used to deliver loss-of-function vectors that trigger hESC differentiation in a doxycycline-inducible manner despite the presence of non-differentiating culture conditions.

It was also investigated whether a combination of loss- and gain-of-function systems could be used to drive differentiation toward one particular cell type, namely a neural cell type. We added a thymidine kinase cassette to our TetON system (FIG. 4A) and made transgenic RUES2 cells expressing human Sox1 cDNA to direct differentiation toward ectoderm, and shRNAs against Oct4, Gata6, Brachyury and Cdx2 to induce differentiation but minimize the acquisition of endodermal, mesodermal or trophectodermal phenotypes. Five-hundred to 1000-cell transgenic colonies were obtained under neomycin selection before doxycycline was added to the conditioned culture medium. After 10 days of culture in conditioned medium with doxycycline, quantitative RT-PCR analyses indicated that expression of pluripotency markers had significantly decreased upon doxycycline treatment and the expression of neural-specific genes Sox1 and NFH was preponderant over that of endodermal, mesodermal and trophectodermal markers (FIG. 5A). Furthermore, hESCs had differentiated into flattened cell types and groups of 10-50 round structures (FIG. 5B) reminiscent of neural rosettes (Zhang, S. C., et al. (2001) Nat. Biotechnol. 19: 1129-1133) had appeared in 91% (n=309) of flattened cell colonies. Immunofluorescent staining for the neuroectodermal marker Pax6 and the neural precursor marker nestin (FIG. 5C) confirmed that the round structures were neural rosettes. These results indicate that ePiggyBac can deliver cocktails of doxycycline-inducible loss- and gain-of-function transgenes that drive differentiation toward a neuronal cell type without the need for a defined culture medium (other than the conditioned medium commonly used to maintain hESCs), feeder cells or embryoid body formation (Zhang, S. C., et al. (2001) Nat. Biotechnol. 19: 1129-1133).

To determine whether transgenes could be removed without loss of the neural phenotype, neural rosettes were isolated by enzymatic treatment and allowed to form neural spheres (Zhang, S. C., et al. (2001) Nat. Biotechnol. 19: 1129-1133) in conditioned medium supplemented with doxycycline. Seven-day-old neural spheres were then triturated to obtain 5-10-cell clumps, nucleofected with the Gal4-ePiggyBac helper and UAS-carrying recipient plasmid and cultured in suspension in N2 medium. Forty eight hours after transfection, ganciclovir selection was applied and ganciclovir-resistant neural spheres were obtained (FIG. 5D) after an additional seven days of culture. Neural spheres were then cut in halves. PCR genotyping was performed on one half to confirm that the transgenes had been removed (not shown). The other half of the sphere was plated on matrigel-coated plates and cultured for 4 days. Genotyping confirmed that all ganciclovir-resistant neural spheres were devoid of transposons and upon attachment to the matrigel substrate, they formed neurites expressing the neural precursor marker nestin and the neuronal markers doublecortin, neurofilament heavy chain and Map2 (FIGS. 5E-G). These results indicate that ePiggyBac can deliver cocktails of transgenes that direct differentiation toward a specific phenotype which is conserved upon transgene removal.

Example 10

Reprogramming Human Somatic Cells into Induced Pluripotent Cells by Reversible Transpositional Strategy In our previous work (study 2) we described the optimization of an insect transposable system for human embryonic stem cell expression and forward genetic approaches. In the present study we take advantage of this new tool to reprogram mouse and human somatic cells into induced pluripotent cell (iPS). Three genes have been recently shown to be sufficient for this reprogramming (Yamanaka 2005, Jaenish 2005, Yamanaka 2007, Thomson 2007, Dailey 2008). We provide an alternative for the precise delivery of these genes, alone or as cargo (using the polycistronic 2-peptide system), encoded within the transposable element. We show that this approach is superior to the technology previously adopted for these experiments, as it is inducible, and more importantly reversible. Current technology describing reprogramming suffers from using retroviral-mediated integration, which ultimately compromises genome integrity and is not compatible with clinical applications. Our system does not use retroviruses, and once reprogrammed the transposable element can be removed from the human genome without leaving a trace. These improvements eliminate one of the most important current limitations in the use of iPS in clinic.

Introduction

The recent discovery that three or four genes are sufficient to convey pluripotency to human somatic cells has generated tremendous excitement regarding the possible application of cell-based therapies in clinic. Pluripotency is one of the main attributes of stem cells and describes the potential of a cell to give rise to a variety of other cell types. The repertoire of cell types that a stem cell can give rise to varies extensively among different stem cell types. The mother of all stem cells is the fertilized egg, which manages to make a whole organism, and therefore has the ability to ultimately differentiate to all cell types, a property known as totipotency. The only other totipotent cell type known is embryonic stem cells, derived from the very early cleavage stage embryos. Adult stem cells are not endowed with totipotency, but are pluripotent instead, reflecting the fact that while they can differentiate into many cell types their range is much more limited. Best-studied examples of adult stem cells include the stem cells of the bone marrow, currently used in clinic for the regeneration of the entire hematopoeitic system in vivo. Special emphasis on the study of in human embryonic stem cells (HESCs) is based on this unique totipotency attribute.

The study of HESCs, which provides both a window to the basic understanding of human development, as well as a potential to establish a cell-based therapy platform, suffers from socio-political restrictions as they involve the destruction of human embryo. In order to provide an alternative source of pluripotent (if not totipotent) cells for clinical use, a recent report inspired by pioneering work done in the mouse (Yamanaka 2005, Jaenish 2005), has shown that human somatic cells can be "reprogrammed" to embryonic stem cells (Yamanaka 2007, Thomson 2007, Dailey 2008). This can be accomplished by a simple retroviral-mediated transfection of three genes, Sox2, Oct4, and Klf4 to human somatic cells. Reprogramming somatic cells provides a unique opportunity to generate patient specific pluripotent cells. However, while this retroviral mediated reprogramming clearly endows somatic cells with embryonic type of activity, it suffers from the delivery technology that irreversibly modifies the human genome and introduces serious risk of tumorigenesis making it currently inappropriate for clinical application.

In this study, we explore the ability of our new transposons elements, to deliver the same genes, but this time in a reversible manner, not leaving any trace in the genome. After reproducing published results, we first establish that, reprogramming can be achieved when the three genes are delivered by our transposon. This can be accomplished by either mono- or poly-cistronic cassette message under the control of an UAS element, which amplifies expression when co-expressed with Gal4-VP16 provided in trans. Our approach therefore provides an alternative protocol for reprogramming human somatic cells. More importantly, once this reprogramming is conveyed to the cells, the vector can be removed from the genome without affecting genome integrity. This transient expression and clean removal that sustains pluripotency, without the use of retroviruses and without affecting genome integrity, eliminates a major hurdle toward cell based therapies in clinical application of HESCs.

Material and Methods
1—Lentiviral vector construction
2—PiggyBac vector construction
3—Cell culture, lipofection
4—Microscopy and signal detection
5—RT-PCR analysis
6—Embryoid body formation
7—Teratoma formation Results Poly-cistronic delivery of reprogramming genes in mouse and human somatic cells To test and compare the activity of the reprogramming genes when delivered by different vectors we perform three sets of experiments addressing the feasibility of our approach.

In the first set we tested the activity of plasmids encoding the Oct4, Sox2, and Klf4 genes under the control of the ubiquitous PGK promoter in a tri-cistronic message (FIG. 13). cMyc was put on a separate mono-cistronic vector also under the control of PGK to be included separately if needed. EGFP was used as control.

Figure 14:
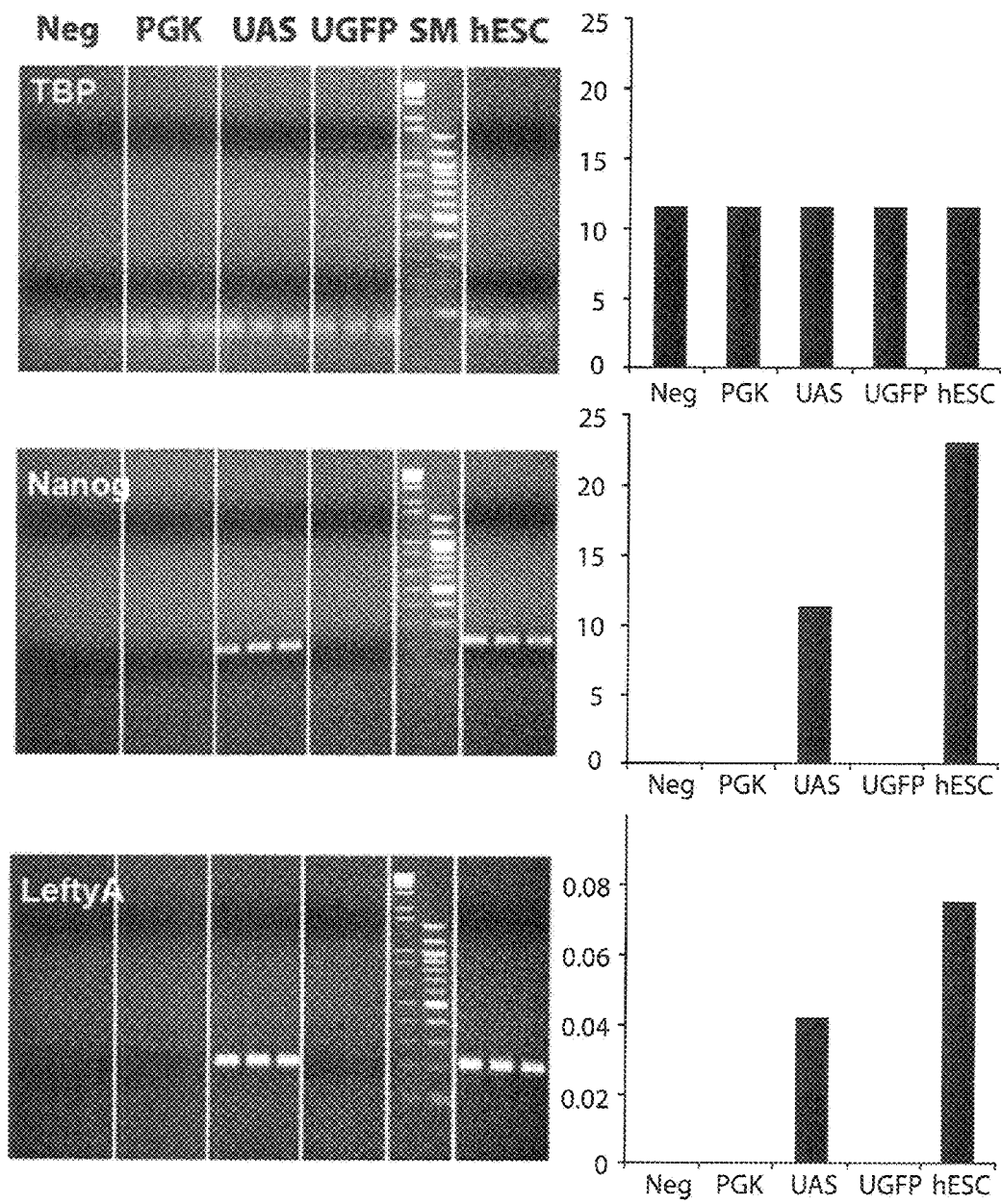
FIG. 14. Reprogramming of human fibroblast cells by combining poly-cistronic expression with transcriptional amplification. Right panel RT-PCR analysis of reprogramming. TBP is a loading control; Nanog and lefty are cell-type specific markers of sternness in embryonic stem cells. Neg.=non-transfected negative control human fibroblast cells; PGK=transfection with genes under PGK control (no-amplification); UAS=Oct4-Sox2-Klf4 and c-Myc under UAS amplification control; hESC=positive controls for marker expression; SM=Size markers. RT-PCR was done for 45 cycles. Left panel represent quantification of the RT-PCR. Only when the four genes are presented under amplification that reprogramming can be achieved.

These plasmids were transfected in foreskin fibroblasts human cells and evaluated for their activity in reprogramming these somatic cells in iPS. Under this type of condition the plasmids do not integrate into the human genome and remain episomal. No reprogramming activity was observed (FIG. 14).

Figure 15:
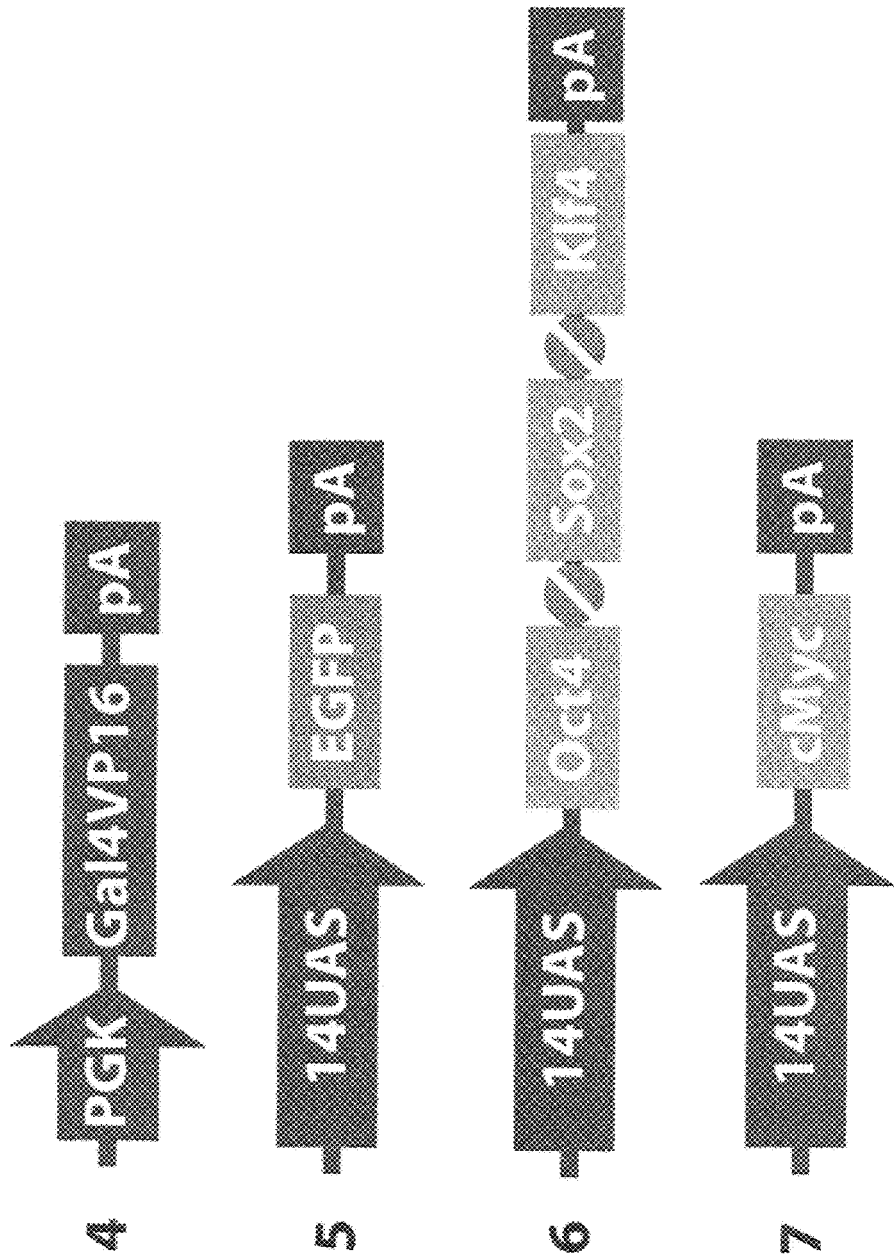
FIG. 15. Recombinant DNA constructs for experimental set 2.

In the second set, we generated a transcriptional amplification system by taking advantage of the Gal4VP16/UAS system. Gal4VP16 transcriptional activator under the control of the ubiquitous promoter PGK, activates and amplifies a synthetic promoter made of 14 tandem copies of the Gal4 promoter, 14UAS (FIG. 15). This produces high levels of expression of the reprogramming genes, a requirement observed both in human and mouse ESCs (Yamanaka 2005, 2007, Jaenish 2005, Thomson 2007). When this collection was assayed for its reprogramming activity on somatic human fibroblast, we observed robust reprogramming after a few days, as illustrated by the expression embryonic stem cells specific marker nanog and lefty (FIG. 14).

Figure 16:
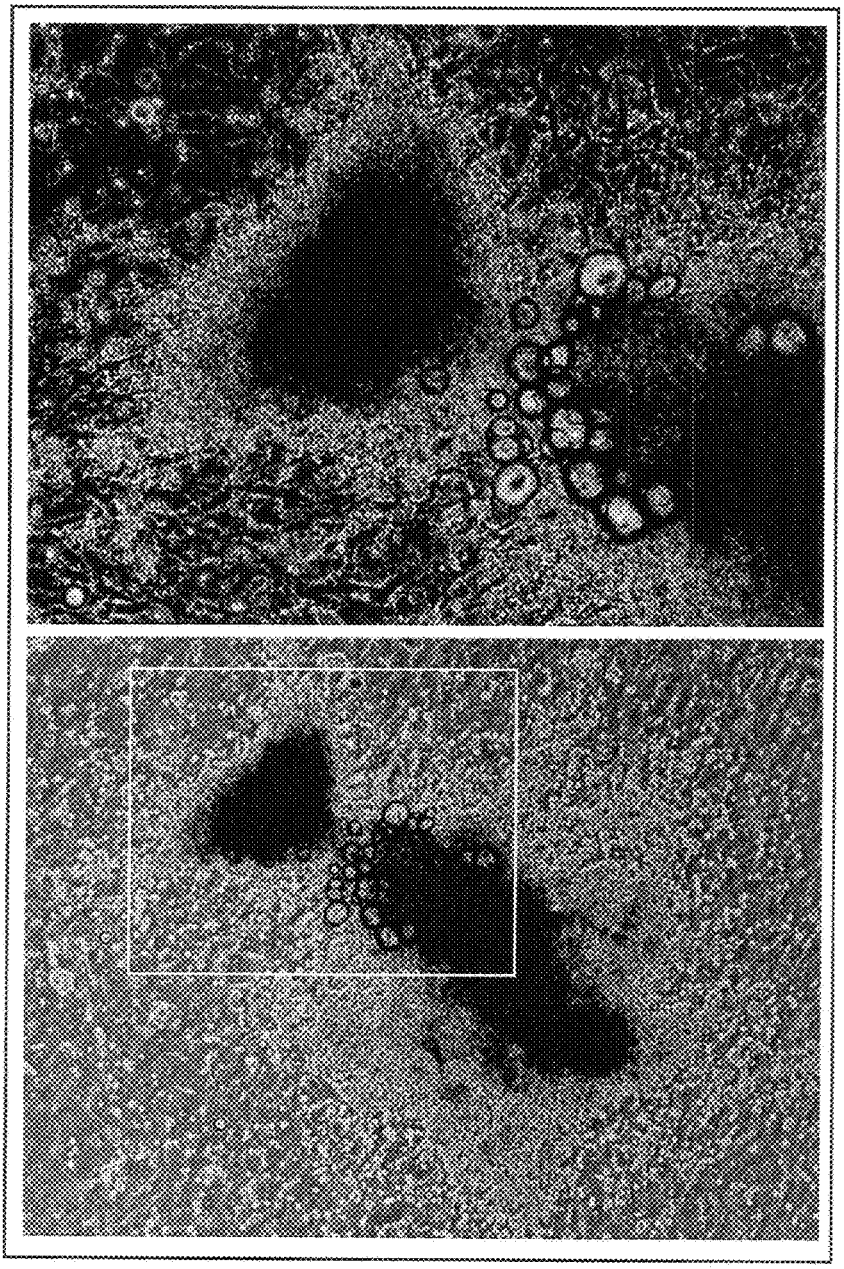
FIG. 16. Mouse somatic fibroblasts (MEF) adapt stable stem cell colony morphology. Left panel is a magnification of the inset in the panel on the right.

While this result confirmed that reprogramming of human somatic cells can occur under over-expression conditions, provided by the transcriptional amplification cassette, the cells lost stemness marker expression and thus could not maintain their reprogram state. When these same constructs were tested in the context of mouse fibroblasts (MEF), but this time presented in a linear topology, stable stem cell colonies could be observed over several passages (FIG. 16).

In human ESCs the lack of maintenance of the reprogrammed state is due to the instability of circular plasmids that do not integrate in the genome, and are expressed episomally, while in mouse ESCs linearized plasmids integrate easily in the genome. This observation highlights the requirement for stable genomic integration to maintain sternness fate.

Figure 17:
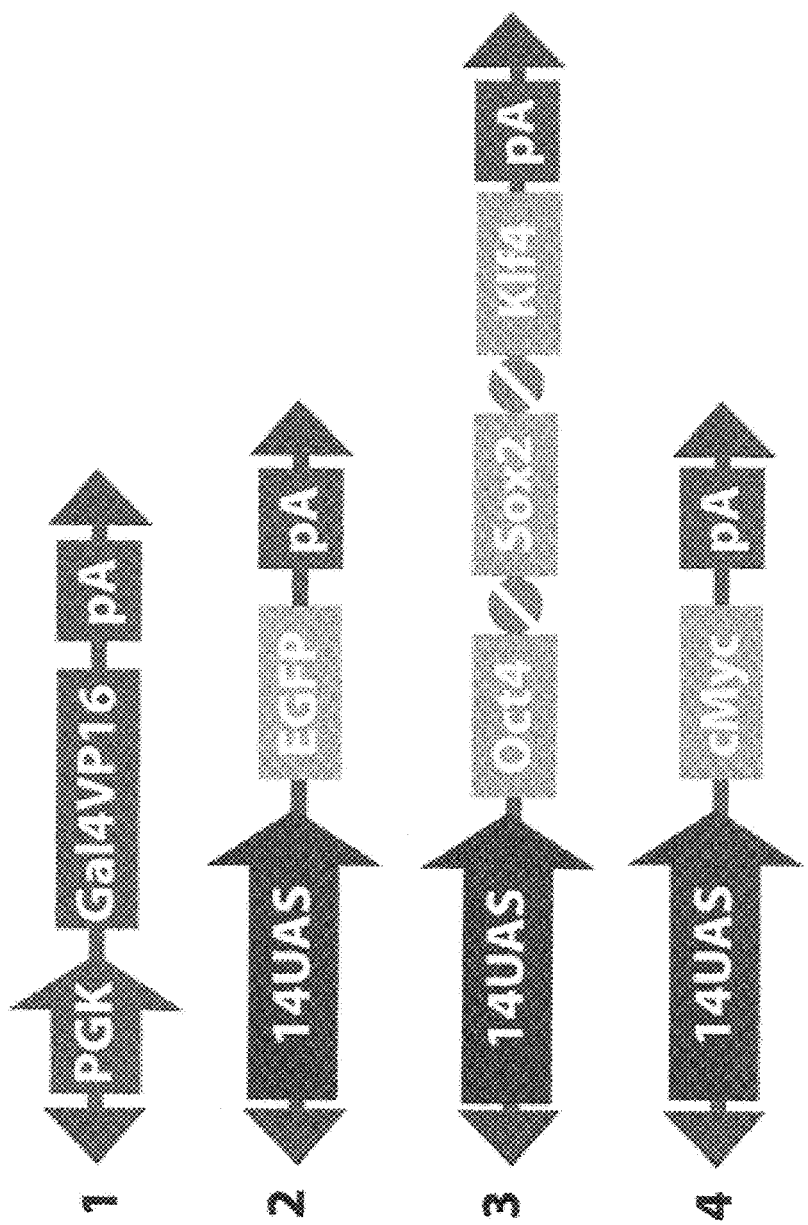
FIG. 17. Amplification/poly-cistronic reprogramming genes in humanized piggyBac. Small, lighter shade triangles at ends of construct represent terminal repeats of the transposon.

In our third experimental setting we sub-cloned our amplification multi- and mono-cistronic cassettes in our humanized piggyBac vector (FIG. 17).

Figure 18:
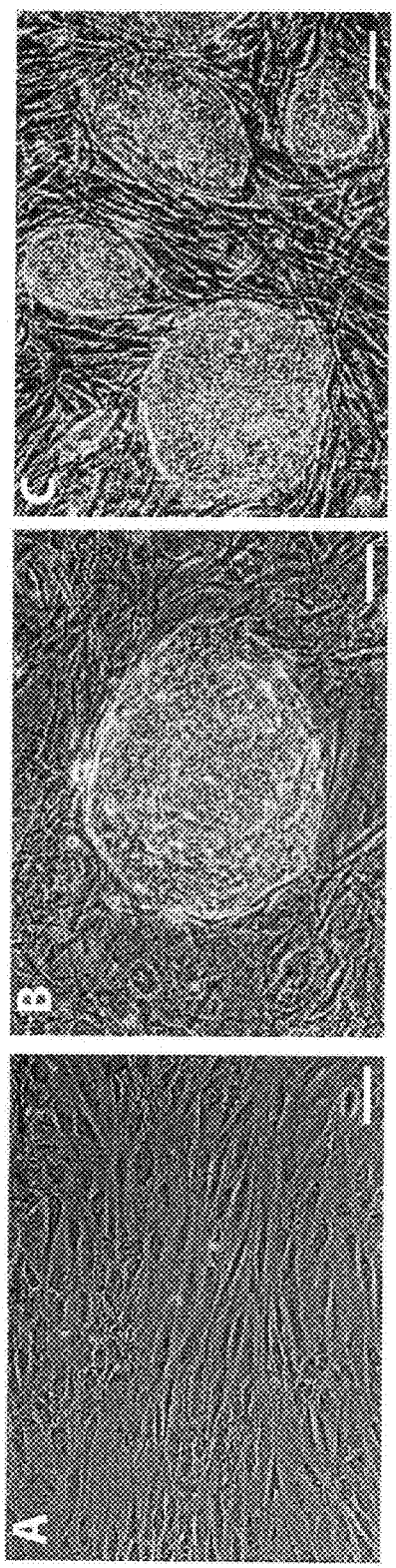
FIG. 18. Human foreskin somatic fibroblast reprogrammed to iTS cells. (A) Control human fibroblast grown throughout the experiment in CM display normal fibroblast morphology. (B) Reprogrammed iTS. (C) Human embryonic stem cells colony (RUES1).

These constructs along with a PGK plasmid encoding the optimized transposase were lipofected into human foreskin fibroblast and cultured for several days in the presence of CM. FIG. 18 shows that human somatic cells have been reprogrammed to colonies that morphologically are identical to human embryonic stem cells. For this reason we suggest the nomenclature iTS, as oppose to iPS, to highlight the totipotency of our reprogrammed cells. The reprogrammed morphology is stable over several passages and does not change. Negative controls for this experiment included lipofection of 14UAS-EGFP with PGK-Gal4VP16, or non-lipofected cells grown in the presence of CM did not show any colony formation (data not shown).

We have therefore demonstrated that an alternative approach to reprogramming human somatic cells toward embryonic stem cells does work. This represents a major improvement of the technology, as retroviral insertion into the human genome, which causes tumor formation, is no longer required. In addition the fact that this transposition is reversible and does not affect the integrity of the human genome allows the removal of all vectors from the genome once the reprogramming is accomplished, alleviating a clinical limitation.

Example 11

Construction and Description of the ePiggyBac-MCS (epB-MCS) Vector

To construct the ePiggyBac-MCS (epB-MCS) vector (SEQ ID NO:41), the cassette [5′TR-MCS-pA-3′TR] was synthesized by GenScript, Inc. (Piscataway, N.J., USA) and cloned between the SacII and KpnI sites of the vector pBluescript™ II SK+ (Stratagene, Carlsbad, Calif.).

Figure 19:
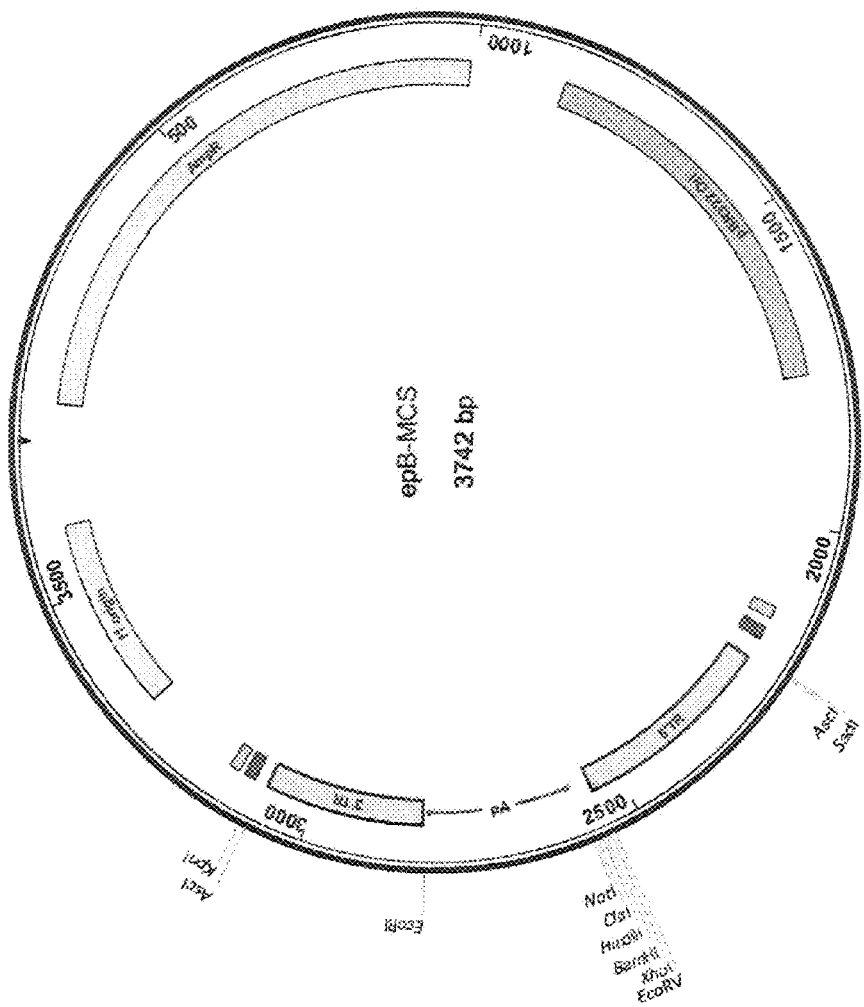
FIG. 19. A diagram of the epB-MCS vector is shown. The polyadenylation sequence is labeled "pA" the enhanced 5' terminal repeat is labelled "5'TR", and the 3' terminal repeat is labeled "3'TR".

The ePiggyBac-MCS (epB-MCS) vector (SEQ ID NO:43) is characterized by the two terminal repeats (TRs), derived from the piggyBac transposable element, flanking a multi-cloning site (MCS: EcoRV-XhoI-BamHI-HindIII-ClaI-NotI) and a poly-adenylation (pA) sequence (FIG. 19). The main advantage of the MCS-pA design is that every insert (promoter+coding sequence) can be easily cloned between the TRs using the restriction sites in the MCS. Addition of a pA signal is not necessary since it is provided in the vector. The pA sequence is the same as in the previous PiggyBac vectors (Lacoste et al., 2009 Cell Stem Cell, September 4; 5(3):332-42; and Cell Stem Cell. 2009 Nov. 6; 5(5):568, each incorporated herein by reference in their entireties). The 5′ terminal repeat (5′TR) contains the two point mutations, described in Lacoste et al., 2009 (Cell Stem Cell), which improve the efficiency of integration. The sequence of the cassette [5′TR-MCS-pA-3′TR] is provided herewith in FIG. 20 and as SEQ ID NO: 44.

Certain biological sequences referenced herein by their "NCBI Accession Number" or common names can be accessed through the National Center of Biotechnology Information on the world wide web at www.ncbi.nlm.nih.gov.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A nucleic acid comprising an enhanced PiggyBac transposon 5'-terminal repeat sequence having at least 98% identity to SEQ ID NO:1, wherein the residue at a position corresponding to residue number 54 of SEQ ID NO:1 is a cytosine and the residue at a position corresponding to residue number 137 of SEQ ID NO:1 is a thymine.

2. The nucleic acid of claim 1 wherein said enhanced PiggyBac transposon 5'-terminal repeat sequence has one or more non-wild-type residue substitutions A51T, C153A, C277T, G201A, G202A, T236A, A103T, A104C, T140C, G138T, T118A, C74T, or A179C in SEQ ID NO:1.

3. A nucleic acid comprising an enhanced PiggyBac transposon 5'-terminal repeat sequence having at least 99% identity to SEQ ID NO:1, wherein the residue at a position corresponding to residue number 54 of SEQ ID NO:1 is a cytosine and the residue at a position corresponding to residue number 137 of SEQ ID NO:1 is a thymine.

4. A recombinant DNA construct comprising an enhanced PiggyBac transposon 5'-terminal repeat sequence having at least 98% identity to SEQ ID NO:1, wherein the residue at a position corresponding to residue number 54 of SEQ ID NO:1 is a cytosine and the residue at a position corresponding to residue number 137 of SEQ ID NO:1 is a thymine.

5. The recombinant DNA construct of claim 4, wherein said recombinant DNA construct further comprises a PiggyBac 3' terminal repeat sequence and an exogenous insertion sequence that is operably linked to said 5'-terminal repeat sequence and to said 3'-terminal repeat sequence.

6. The recombinant DNA construct of claim 4, wherein said 5'-terminal repeat sequence has at least 99% identity to SEQ ID NO:1.

7. The recombinant DNA construct of claim 6, wherein said enhanced PiggyBac transposon 5'-terminal repeat sequence has one or more non-wild-type residue substitutions A51T, C153A, C277T, G201A, G202A, T236A, A103T, A104C, T140C, G138T, T118A, C74T, or A179C in SEQ ID NO:1.

8. The recombinant DNA construct of claim 5, wherein said exogenous insertion sequence comprises at least one of: i) a sequence for operable insertion of a heterologous DNA sequence; ii) a selectable marker; iii) a counter-selectable marker; iv) a gene encoding a regulatory protein; v) a gene encoding an inhibitory RNA, or any combination thereof.

9. The recombinant DNA construct of claim 5, wherein said enhanced PiggyBac transposon 5'-terminal repeat sequence provides for an increased frequency of transposition of an exogenous insertion sequence of greater than 14.4 kB in length.

10. A method for obtaining a cell with a genome comprising a reversibly integrated exogenous DNA insert, said method comprising the steps of:
(a) introducing an enhanced PiggyBac transposon into a cell in the presence of a PiggyBac transposase, wherein said enhanced PiggyBac transposon comprises; i) an operably linked 5'-terminal repeat sequence having at least 98% identity to SEQ ID NO:1 and comprising a cytosine at a position corresponding to residue number 54 of SEQ ID NO:1 and a thymine at a position corresponding to residue number 137 of SEQ ID NO:1; ii) an operably linked exogenous DNA insert; and iii) an operably linked 3' terminal repeat sequence; and,
(b) isolating a cell wherein said enhanced PiggyBac transposon has integrated into a genomic sequence of said cell, thereby obtaining a cell with a genome comprising a reversibly integrated exogenous DNA insert.

11. The method of claim 10, wherein said exogenous DNA insert comprises at least one of: i) a selectable marker; ii) a counter-selectable marker; iv) a gene encoding a regulatory protein; v) a gene encoding an inhibitory RNA, or any combination thereof.

12. The method of claim 10, wherein said PiggyBac transposase is provided by; i) co-introducing said enhanced PiggyBac transposon and a nucleic acid construct that provides for the presence of PiggyBac transposase into said cell; or by ii) introducing said enhanced PiggyBac transposon into a cell comprising a nucleic acid construct that provides for the presence of PiggyBac transposase.

13. The method of claim 10, wherein said exogenous DNA insert is greater than 14.4 kB in length.

14. A method for obtaining a cell that has undergone a reversible genetic modification, said method comprising:
(a) providing a cell with
a genome comprising a reversibly integrated enhanced PiggyBac transposon, wherein said enhanced PiggyBac transposon comprises; i) an operably linked 5'-terminal repeat sequence having at least 98% identity to SEQ ID NO:1 and comprising a cytosine at a position corresponding to residue number 54 of SEQ ID NO: 1 and a thymine at a position corresponding to residue number 137 of SEQ ID NO: 1; ii) an operably linked exogenous DNA insert; and iii) an operably linked 3' terminal repeat sequence,
a PiggyBac transposase, and
a recipient nucleic acid molecule, wherein said recipient nucleic acid molecule can be removed or lost from said cell;
b) culturing said cell under conditions that provide for transposition of said PiggyBac transposon to said recipient nucleic acid molecule and subsequent removal or loss of said recipient nucleic acid molecule; and
c) isolating a cell comprising a genomic sequence wherein said enhanced PiggyBac transposon has been excised, thereby obtaining a cell that has undergone a reversible genetic modification.

15. The method of claim 14, wherein said PiggyBac transposase is operably linked to a DNA binding domain, and wherein said recipient nucleic acid molecule comprises one or more binding site sequences recognized by said DNA binding domain.

16. The method of claim 14, wherein the transposition of the PiggyBac transposon from the genome to the recipient nucleic acid molecule returns the sequence of the genome at an original transposon insertion site to exactly its pre-insertion sequence.

17. The method of claim 14, wherein said operably linked exogenous DNA insert comprises one or more sequences encoding one or more antisense or inhibitory RNAs that inhibit expression of at least one of an Oct4 a Gata6 a Brach a or Cdx2 gene.

* * * * *